(12) United States Patent
Dahmen et al.

(10) Patent No.: US 6,316,386 B1
(45) Date of Patent: *Nov. 13, 2001

(54) SELECTIVE HERBICIDES BASED ON ARYLSULPHONYLAMINOCARBONYLTRIAZOLINONES

(75) Inventors: Peter Dahmen, Leverkusen; Dieter Feucht, Monheim; Klaus-Helmut Müller, Düsseldorf; Hans-Joachim Santel, Leverkusen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 29 days.

(21) Appl. No.: 09/254,942

(22) PCT Filed: Sep. 10, 1997

(86) PCT No.: PCT/EP97/04947

§ 371 Date: Mar. 19, 1999

§ 102(e) Date: Mar. 19, 1999

(87) PCT Pub. No.: WO98/12923

PCT Pub. Date: Apr. 2, 1998

(30) Foreign Application Priority Data

Sep. 23, 1996 (DE) .............................................. 196 38 887

(51) Int. Cl.[7] .................. A01N 43/653; A01N 33/18; A01N 39/02; A01N 47/38; A01N 57/02

(52) U.S. Cl. .................. 504/128; 504/132; 504/134; 504/136; 504/137; 504/139

(58) Field of Search ................... 504/134, 135, 504/139, 128, 132, 136, 137

(56) References Cited

U.S. PATENT DOCUMENTS

| | | | |
|---|---|---|---|
| 5,085,684 | 2/1992 | Muller et al. | 71/92 |
| 5,094,683 | 3/1992 | Daum et al. | 71/94 |
| 5,149,356 | 9/1992 | Muller et al. | 71/90 |
| 5,173,104 | 12/1992 | Feucht | 71/93 |
| 5,238,910 | 8/1993 | Muller et al. | 504/273 |
| 5,241,074 | 8/1993 | Daum et al. | 548/263.8 |
| 5,276,162 | 1/1994 | Muller et al. | 548/263.4 |
| 5,300,480 | 4/1994 | Hass et al. | 504/273 |
| 5,348,933 | 9/1994 | Sakashita et al. | 504/213 |
| 5,380,863 | 1/1995 | Muller et al. | 548/263.6 |
| 5,380,864 | 1/1995 | Muller et al. | 548/263.8 |
| 5,405,970 | 4/1995 | Daum et al. | 548/263.6 |
| 5,457,084 | 10/1995 | Sakashita et al. | 504/215 |
| 5,488,028 | 1/1996 | Haas et al. | 504/193 |
| 5,532,378 | 7/1996 | Daum et al. | 548/263.8 |
| 5,534,486 | 7/1996 | Muller et al. | 504/273 |
| 5,541,337 | 7/1996 | Muller et al. | 548/263.6 |
| 5,554,761 | 9/1996 | Haas et al. | 548/263.6 |
| 5,583,231 | 12/1996 | Sakashita et al. | 546/293 |
| 5,597,939 | 1/1997 | Muller et al. | 558/8 |
| 5,599,944 | 2/1997 | Muller et al. | 548/263.6 |
| 5,625,074 | 4/1997 | Daum et al. | 548/263.8 |
| 5,631,380 | 5/1997 | Hass et al. | 548/263.4 |
| 5,652,372 | 7/1997 | Muller et al. | 548/263.4 |
| 5,750,718 | 5/1998 | Muller et al. | 548/263.6 |

FOREIGN PATENT DOCUMENTS

96/11188 4/1996 (WO) .

OTHER PUBLICATIONS

S.R. Colby, Weeds 15, pp. 20–22 (month unavailable) 1967, Calculating Synergistic and Antagonistic Responses of Herbicide Combinations.

*Primary Examiner*—S. Mark Clardy
(74) *Attorney, Agent, or Firm*—Joseph C. Gil

(57) ABSTRACT

The novel herbicidally active compound combinations comprising (a) an arylsulphonylaminocarbonyltriazolinone of the formula (I)

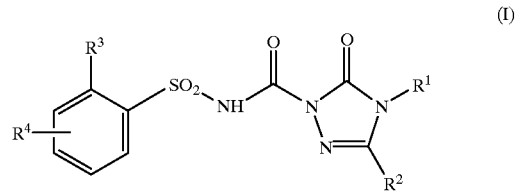

(in which $R^1$, $R^2$, $R^3$ and $R^4$ are each as defined in the description) and/or a salt of a compound of the formula (I) (="active compound of Group 1") and (b) one or more compounds from a second group of certain known herbicides (="active compound of Group 2") exhibit at certain weight ratios synergistic effects and can be employed as selective herbicides in various crops of useful plants;
typical examples are active compound combinations from the Na salts of the compounds of the formula (I) where $R^1=CH_3$, $R^2=OC_3H_7$, $R^3=COOCH_3$ and $R^4=H$ (I-1) or where $R^1=CH_3$, $R^2=OCH_3$, $R^3=OCF_3$ and $R^4=H$ (I-2) as active compound of Group 1 and metribuzin as active compound of Group 2.

7 Claims, No Drawings

SELECTIVE HERBICIDES BASED ON ARYLSULPHONYLAMINOCARBONYLTRIAZOLINONES

This application has been filed under 35 U.S.C. 371 as the national stage of international application PCT/EP97/04947 filed Sep. 10, 1997.

TECHNICAL FIELD OF THE INVENTION

The invention relates to novel herbicidal synergistic active compound combinations comprising, on the one hand, known arylsulphonylaminocarbonyltriazolinones and, on the other hand, known herbicidally active compounds, which can be used particularly successfully for selectively controlling weeds in a variety of crops of useful plants.

BACKGROUND OF THE INVENTION

Sulphonylaminocarbonyltriazolinones, which are herbicides having a broad spectrum of action, are the subject of a series of patent applications (cf. EP 341489, EP 422469, EP 425948, EP 431291, EP 507171, EP 534266, WO 96/11188, DE 19508118). However, the known sulphonylaminocarbonyltriazolinones have a number of gaps in their action.

Surprisingly, it has now been found that a number of known active compounds from the series of the arylsulphonylaminocarbonyltriazolinones, when used together with known herbicidally active compounds from various substance classes, exhibit pronounced synergistic effects with regard to the activity against weeds and can be used particularly advantageously as broad-spectrum combination preparations for the selective control of weeds in crops of useful plants, such as, for example, wheat.

DETAILED DESCRIPTION OF THE INVENTION

The invention accordingly provides selective herbicidal compositions, characterized by an effective content of a combination of active compounds comprising
(a) an arylsulphonylaminocarbonyltriazolinone of the general formula (I)

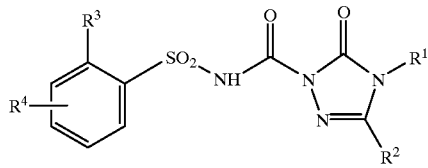

(I)

in which
$R^1$ represents hydrogen, hydroxyl, amino, alkylideneamino or represents alkyl, alkenyl, alkinyl, alkoxy, alkenyloxy, alkylamino, dialkylamino, cycloalkyl, cycloalkylalkyl, cycloalkylamino, aryl or arylalkyl, each of which is optionally substituted,
$R^2$ represents hydrogen, hydroxyl, mercapto, amino, cyano, halogen or represents alkyl, alkoxy, alkylthio, alkylamino, dialkylamino, alkenyl, alkinyl, alkenyloxy, alkinyloxy, alkenylthio, alkinylthio, alkenylamino, alkinylamino, cycloalkyl, cycloalkyloxy, cycloalkylthio, cycloalkylamino, cycloalkylalkyl, aryl, aryloxy, arylthio, arylamino or arylalkyl, each of which is optionally substituted,
$R^3$ represents nitro, cyano, halogen or represents alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy, alkinylthio, cycloalkyl, cycloalkyloxy, cycloalkylthio, cycloalkylamino, aryl, aryloxy, arylthio, arylsulphinyl, arylsulphonyl or arylamino, each of which is optionally substituted, and
$R^4$ represents hydrogen, nitro, cyano, halogen or represents alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy, alkinylthio, cycloalkyl, cycloalkyloxy, cycloalkylthio, cycloalkylamino, aryl, aryloxy, arylthio, arylsulphinyl, arylsulphonyl or arylamino, each of which is optionally substituted, and/or a salt of a compound of the formula (I) ("active compounds of Group I")

and
(b) one or more compounds from a second group of herbicides comprising the active compounds listed below:
2-chloro-N-(ethoxymethyl)-N-(2-ethyl-6-methyl-phenyl)-acetamide (acetochlor), 2-chloro-6-nitro-3-phenoxy-aniline (aclonifen), 2-chloro-N-(methoxymethyl)-N-(2,6-diethyl-phenyl)-acetamide (alachlor), N-(4,6-dimethoxy-pyrimidin-2-yl)-N'-(N-methyl-N-methylsulphonyl-sulphamoyl)-urea (amidosulfuron), 6-chloro4-ethylamino-2-isopropylamino-1,3,5-triazine (atrazine), 4-chloro-2-oxo-3(2H)-benzothiazolylacetic acid (benazolin), ethyl N-benzoyl-N-(3,4-dichloro-phenyl)-DL-alaninate(benzoylprop-ethyl), 3-i-propyl-1H-2,1,3-benzothiadiazin4(3H)-one (bentazon), methyl 5-(2,4-dichloro-phenoxy)-2-nitro-benzoate (bifenox), 2-bromo-3,3-dimethyl-N-(1-methyl-1-phenyl-ethyl)-butanamide (bromobutide), 3,5-dibromo-4-hydroxy-benzaldehyde O-(2,4-dinitr-phenyl)-oxime (bromofenoxim), 3,5-dibromo-4-hydroxy-benzonitrile (bromoxynil), N-butoxymethyl-2-chloro-N-(2,6-diethyl-phenyl)-acetamide (butachlor), S-ethyl bis-(2-methyl-propyl)-thiocarbamate (butylate), 2-(4-chloro-2-fluoro-5-(2-chloro-2-ethoxycarbonyl-ethyl)-phenyl)-4-difluoromethyl-5-2,4-dihydro-3H-1,2,4-triazol-3-one (carfentrazone-ethyl, F-8426), 2,4-dichloro-1-(3-methoxy-4-nitro-phenoxy)-benzene (chlomethoxyfen), 3-amino-2,5-dichloro-benzoic acid (chloramben), 1,3,5-trichloro-2-(4-nitro-phenoxy)-benzene (chlornitrofen), N-(4-methoxy-6-methyl-1,3,5-triazin-2-yl)-N'-(2-chloro-phenylsulphonyl)-urea (chlor-sulfuron), N'-(3-chloro-4-methylphenyl)-N,N-dimethyl-urea (chlortoluron), N-(4,6-dimethoxy-1,3,5-triazin-2-yl)-N'-(2-(2-methoxy-ethoxy)-phenylsulphonyl)-urea (cinosulfuron), (R)-(2-propinyl)-2-[4-(5-chloro-3-fluoro-pyridin-2-yl-oxy)-phenoxy-propanoate (clodinafop-propargyl), 3,6-dichloro-pyridine-2-carboxylic acid (clopyralid), N-(4,6-dimethoxy-pyrimidin-2-yl)-N'-(3-chloro-4-methoxycarbonyl-1-methyl-pyrazol-5-yl-sulphonyl)-urea (clopyrasulfuron, halosulfuron, NC-319), methyl-3-chloro-2-[(5-ethoxy-7-fluoro[1,2,4]triazolo[1,5-c]-pyrimidin-2-yl-sulphonyl)-amino]-benzoate (cloransulam-methyl), 2-chloro-4-ethyl-amino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron, AC-322140), 2,4-dichloro-phenoxyacetic acid (2,4-D), 3,6-dichloro-2-methoxy-benzoic acid (dicamba), (R)-2-(2,4-dichloro-phenoxy)-propionic acid (dichlorprop-P), methyl 2-[4-(2,4-dichloro-phenoxy)-phenoxy]-propate (diclofop-methyl), 1,2-dimethyl-3,5-diphenyl-1H-pyrazolium methyl sulphate (difenzoquat), N-(2,4-difluoro-phenyl)-2-(3-trifluoromethyl-phenoxy)-pyridine-3-carboxamide (diflufenican), 2-chloro-N-(2,4-dimethyl-3-thienyl)-N-(2- methoxy-1-methyl-ethyl)-acetamide (dimethenamide, SAN-582), 2-amino-4-(1-fluoro-1-methyl-ethyl)-6-(1-methyl-2-(3,5-dimethyl-phenoxy)-ethylamino)-1,3,5-triazine (dimexyflam, IDH-1105), N3,N3-diethyl-2,4-dinitro-6-trifluoromethyl-1,3-diamino-benzene (dinitramine), the sodium salt of N-(4,6-dimethoxy-pyrimidin-2-yl)-N'-(3-methoxycarbonyl-6-trifluoromethyl-pyridin-2-yl-sulphonyl)-urea (DPX-KE459), 6,7-dihydro-dipyrido[1,2-a:2',1'-c]pyrazinediium (diquat), S,S-dimethyl 2-difluoromethyl-4-i-butyl-6-trifluoromethyl-pyridine-3,5-dicarbothioate (dithiopyr), the sodium salt of N-(4,6-dimethoxy-pyrimidin-2-yl)-N'-(3-methoxycarbonyl-6-trifluoromethyl-pyrimidin-2-yl-sulphonyl)-urea (DPX-KE-459), S-ethyl dipropylthio-carbamate (EPTC), S-(phenylmethyl) N-ethyl-N-(1,2-dimethyl-propyl)-thiocarbamate (esprocarb), ethyl [2-chloro-5-(4-chloro-5-difluoromethoxy-1-methyl-1H-pyrazol-3-yl)-4-fluoro-phenoxy]-acetate (ET-751), (S)-(2-ethoxy-1-methyl-2-oxoethyl) 2-chloro-5-(2-chloro-4-trifluoromethyl-phenoxy)-benzoate (ethoxyfen), N-(4,6-dimethoxy-pyrimidin- 2-yl)-N'-(2-ethoxy-phenoxysulphonyl)-urea (ethoxysulfuron, HOE-095404), ethyl 2-[4-(6-chloro-benzoxazol-2-yl-oxy)-phenoxy]-propanoate (fenoxaprop-ethyl), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluorophenyl)-5-methyl-1,2,4-triazolo[1,5-a]-pyrimidine-2-sulphonamide (flumetsulam, DE-498), pentyl [2-chloro-4-fluoro-5-(1,3,4,5,6,7-hexahydro-1,3-dioxo-2H-isoindol-2-yl)-phenoxy]-acetate (flumiclorac-pentyl), 2-[4-chloro-2-fluoro-5-[(1-methyl-2-propinyl)-oxy]-phenyl]4,5,6,7-tetrahydro-1H-isoindole-1,3(2H)-dione (flumipropyn), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1(2H)-pyrimidyl)-benzoate (flupropacil), 9-hydroxy-9H-fluorene-9-carboxylic acid (flurenol), 4-amino-3,5-dichloro-6-fluoro-pyridin-2-yl-oxy)-acetic acid (fluroxypyr), 5-methylamin-2-phenyl-4-(3-trifluoromethyl-phenyl)-3(2H)-fuoanone (flurtamone), methyl [(2-chloro-4-fluoro-5-(tetrahydro-3-oxo-1H,3H-[1,3,4]-thiadiazolo[3,4-a]-pyridazin-1-ylidene)-amino-phenyl]-thioacetate (fluthiacet-methyl, KIH-9201), 2-amino-4-(hydroxymethyl-phosphinyl)-butanoic acid (ammonium salt) (glufosinate-(ammonium)), N-phosphonomethyl-glycine (-isopropylammonium), (glyphosate, -isopropylammonium), methyl 2-(4,5-dihydro-4-methyl-4-isopropyl-5-oxo-1H-imidazol-2-yl)-4-methyl-benzoate (imazamethabenz-methyl), 2-(4,5-dihydro-4methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (5-cyclopropyl-isoxazol-4-yl)-(2-methylsulphonyl-4-trifluoromethyl-phenyl)-methanone (isoxaflutole, RPA-201772), 2-[2-[4-[3,5-dichloro-2-pyridinyl)-oxy]-phenoxy]-1-oxo-propyl]-isoxazolidine (isoxapyrifop), N'-(3,4-dichloro-phenyl)-N-methoxy-N-methylurea (linuron), (4-chloro-2-methyl-phenoxy)-acetic acid (MCPA), 2-(4-chloro-2-methyl-phenoxy)-propionic acid (mecoprop), 2-chloro-N-(2,6-dimethylphenyl)-N-(1H-pyrazol-1-yl-methyl)-acetamide (metazachlor), N'-(4-(3, 4-dihydro-2-methoxy- 2,4,4-trimethyl-2H-1-benzopyran-7-yl-oxy)-phenyl)-N-methoxy-N-methylurea (metobenzuron, UMP-488), N'-(4-bromo-phenyl)-N-methoxy-N-methylurea (metobromuron), 2-chloro-N-(2-ethyl-6-methyl-phenyl)-N-(2-methoxy-1-methyl-ethyl)-acetamide (metolachlor), N-(2,6-dichloro-3-methyl-phenyl)-5,7-dimethoxy-1,2,4-triazolo[1,5-a]-pyrimidine-2-sulphonamide (metosulam, DE-511), N'-(3-chloro-4-methoxy-phenyl)-N,N-dimethyl-urea (metoxuron), 4-amino-6-tert-butyl-3-methylthio-1,2,4-triazin-5-(4H)-one (metribuzin), N-(4-methoxy-6-methyl-1,3,5-triazin-2-yl)-N'-(2-methoxycarbonyl-phenylsulphonyl)-urea (metsulfuron-methyl), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), S-(2-chlorobenzyl)-N,N-diethyl-thiocarbamate (orbencarb), N-(4,6-dimethyl-pyrimidin-2-yl)-N'-(2-oxetan-3-yl-oxycarbonyl-phenylsulphonyl)-urea (oxasulfuron), 1,1'-dimethyl-4,4'-bipyridinium (paraquat), 1-amino-N-(1-ethyl-propyl)-3, 4-dimethyl-2,6-dinitro-benzene (pendimethalin), N-(4, 6bis-difluoromethoxy-pyrimidin-2-yl)-N'-(2-methoxycarbonyl-phenylsulphonyl)-urea (prirmisulfuron-methyl), S-phenylmethyl N,N-dipropyl-thiocarbamate (prosulfocarb), N-(4-methoxy-6-methyl-1, 3,5-triazin-2-yl)-N'-(2-(3,3,3-trifluoro-propyl)-phenylsulphonyl)-urea (prosulfuron), 2-chloro-N-(2,6-diethyl-phenyl)-N-(2-propoxy-ethyl)-acetamide (pretilachlor), 2-chloro-N-isopropyl-N-phenyl-acetamide (propachlor), O-(6-chloro-3-phenyl-pyridazin-4-yl) S-octyl thiocarbonate (pyridate), 4-(2,4-dichlorobenzoyl)-1,3-dimethyl-5-(4-methyl-phenylsulphonyloxy)-pyrazole (pyrazolate), 4-(2,4-dichloro-benzoyl-1,3-methyl-5-(phenylcarbonylmethoxy)-pyrazole (pyrazoxyfen), N-(4, 6-dimethoxy-pyrimidin-2-yl)-N'-(4-ethoxycarbonyl-1-methyl-pyrazol-5-yl-sulphonyl)-urea (pyrazosulfuron-ethyl),7-chloro-3-methyl-quinoline-8-carboxylic acid (quinmerac), N-(4,6-dimethoxy-pyrimidin-2-yl)-N'-(3-ethylsulphonyl-pyridin-2-yl-sulphonyl)-urea (rimsulfuron), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone, F-6285), N-phosphonomethyl-glycine-trimethylsulphonium (sulfosate), N-(4,6-dimethoxy-pyrimidin-2-yl)-N'-(2ethylsulphonyl-imidazo[1,2-a]pyridine-3-sulphonamide (sulfosulfuron, MON-37500), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), 6-(6,7-dihydro-6,6-dimethyl-3H,5H-pyrrolo[2,1-c]-1,2,4-thiadiazol-3-ylidenamino)-7-fluoro-4-(2-propinyl)-2H-1,4-benzoxazin-3(4H)-one (thidiazimin), N-(4-methoxy-6-methyl-1,3,5-triazin-2-yl)-N'-( 2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropy-lcarbamothioate (triallate), N-(4-methoxy-6-methyl-1,3, 5-triazin-2-yl)-N'-[2-(2-chloro-ethoxy)- phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), 2-(3,5-dichlorophenyl)-2-(2,2,2-trichloro-ethyl)-oxirane (tridiphane), 1-amino-2,6-dinitro-N,N-dipropyl-4-trifluoromethyl-benzene (trifluralin)-("active compounds of Group 2"),
where generally from 0.01 to 1000 parts by weight of an active compound of Group 2 are used per part by weight of an active compound of Group I (i.e. of the formula (I)).

Of particular interest are selective herbicidal compositions according to the invention which are characterized by a content of an active compound combination comprising
(a) an arylsulphonylaminocarbonyltriazolinone of the general formula (I) in which $R^1$ represents hydrogen, hydroxyl, amino, $C_2$–$C_6$-alkylideneamino, represents in each case optionally cyano-, halogen- or $C_1$–$C_4$-alkoxy-substituted alkyl, alkenyl, alkinyl, alkoxy, alkenyloxy, alkylamino or dialkylamino having in each case up to 6 carbon atoms, represents in each case optionally cyano, halogen- or $C_1$–$C_4$-alkyl-substituted cycloalkyl, cycloalkylalkyl or cycloalkylamino having in each case 3 to 6 carbon atoms in the cycloalkyl groups and, if appropriate, 1 to 4 carbon atoms in the alkyl moiety, or represents in each case optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_4$-alkyl, $R^2$ represents hydrogen, hydroxyl, mercapto, amino, cyano, halogen, represents in each case optionally cyano-, halogen- or $C_1$–$C_4$-alkoxy-substituted alkyl, alkoxy, alkylthio, alkylamino, dialkylamino, alkenyl, alkinyl, alkenyloxy, alkinyloxy, alkenylthio, alkinylthio, alkenylamino or alkinylamino having in each case up to 6 carbon atoms, represents in each case optionally cyano-, halogen- or $C_1$–$C_4$-alkyl-substituted cycloalkyl, cycloalkyloxy, cycloalkylthio, cycloalkylamino or cycloalkylalkyl having in each case 3 to 6 carbon atoms in the cycloalkyl groups and, if appropriate, 1 to 4 carbon atoms in the alkyl moiety, or represents in each case optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy, phenylthio, phenylamino or phenyl-$C_1$–$C_4$-alkyl, $R^3$ represents nitro, cyano, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy, alkinylthio having in each case up to 6 carbon atoms, represents in each case optionally cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl groups, or represents in each case optionally cyano-, nitro-, halogen-, $C_1$–$C_4$-alkyl-, $C_1$–$C_4$halogenoalkyl-, $C_1$–$C_4$-alkoxy- or $C_1$–$C_4$-halogenoalkoxy-substituted phenyl, phenoxy, phenylthio, phenylsulphinyl, phenylsulphonyl or phenylamino and, $R^4$ represents hydrogen, nitro, cyano, halogen, represents in each case optionally cyano-, halogen-, or $C_1$–$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy or alkinylthio having in each case up to 6 carbon atoms, represents in each case optionally cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl groups, or represents in each case optionally cyano-, nitro-, halogen-, $C_1$–$C_4$-alkyl-, $C_1$–$C_4$halogenoalkyl-, $C_1$–$C_4$-alkoxy- or $C_1$–$C_4$-halogenoalkoxy-substituted phenyl, phenoxy, phenylthio, phenylsulphinyl, phenylsulphonyl or phenylamino, and/or a salt of a compound of the formula (I) ("active compounds of Group 1")

and (b) one to three compounds from a second group of herbicides which comprises the active compounds listed below:

2-chloro-N-(ethoxymethyl)-N-(2-ethyl-6-methyl-phenyl)-acetamide (acetochlor), 2-chloro-6-nitro-3-phenoxy-aniline (aclonifen), 2-chloro-N-(methoxymethyl)-N-(2,6-diethyl-phenyl)-acetamide (alachlor), N-(4,6-dimethoxy-pyrimidin-2-yl)-N'-(N-methyl-N-methylsulphonyl-sulphamoyl)-urea (amidosulfuron), 6-chloro-4-ethylamino-2-isopropylamino-1,3,5-triazine (atrazine), ethyl N-benzoyl-N-(3,4-dichloro-phenyl)-DL-alaninate (benzoylprop-ethyl), 3-i-propyl-1H-2,1,3-benzothiadiazin-4(3H)-one (bentazon), methyl 5-(2,4-dichloro-phenoxy)-2-nitro-benzoate (bifenox), 2-bromo-3,3-dimethyl-N-(1-methyl-1-phenyl-ethyl)-butanamide (bromobutide), 3,5-dibromo-4-hydroxy-benzaldehyde O-(2,4-dinitro-phenyl)oxime (bromofenoxim), 3,5-dibromohydroxy-benzonitrile (bromoxynil), N-butoxymethyl-2-chloro-N-(2,6-diethyl-phenyl)-acetamide (butachlor), S-ethyl bis-(2-methyl-propyl)-thiocarbamate (butylate), 2-(4-chloro-2-fluoro-(chloro-ethoxycarbonyl-ethyl)-phenyl)-4-difluoromethyl-methyl-2,4-dihydro-3H-1,2,4-triazol-3-one (carfentrazone-ethyl, F-8426), 2,4-chloro-1-(3-methoxy-4-nitro-phenoxy)-benzene (chlomethoxyfen), 3-amino-2,5-dichloro-benzoic acid (chloramben), 1,3,5-trichloro-2-(4-nitro-phenoxy)-benzene (chlornitrofen), N-(4-methoxy-6-methyl-1,3,5-triazin-2-yl)-N'-(2-chlorophenylsulphonyl)-urea (chlorsulfuron), N'-(3-chloro-4-methylphenyl)-N,N-dimethyl-urea (chlortoluron), N-(4,6-dimethoxy-1,3,5-triazin-2-yl)-N'-(2-(2-methoxy-ethoxy)-phenylsulphonyl)-urea (cinosulfuron), (R)-(2-propinyl)-2-[4-(5-chloro-3-fluoro-pyridin-2-yloxy)-phenoxy-propanoate (clodinafop-propargyl), 3,6-dichloro-pyridine-2-carboxylic acid (clopyralid), N-(4,6-dimethoxy-pyrimidin-2-yl)-N'-(3-chloro-4-methoxycarbonyl-1-methyl-pyrazol-5-yl-sulphonyl)-urea (clopyrasulfuron, halosulfuron, NC-319), methyl-3-chloro-2-[(5-ethoxy-7-fluoro[1,2,4]triazolo[1,5-c]pyrimidin-2-yl-sulphonyl)-amino]-benzoate (cloransulam-methyl), 2-chloro-4-ethylamino-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron, AC-322140), 3,6-dichloro-2-methoxy-benzoic acid (dicamba), (R)-2-(2,4-dichloro-phenoxy)-propionic acid (dichlorprop-P), methyl 2-[4-(2,4-dichlorophenoxy)-phenoxy]-propate (diclofopmethyl), 1,2-dimethyl-3,5-diphenyl-1H-pyrazolium methyl sulphate (difenzoquat), N-(2,4-difluoro-phenyl)-2-(3-trifluoromethyl-phenoxy)-pyridine-3-carboxamide (diflufenican), 2chloro-N-(2,4-dimethyl-3-thienyl)-N-(2-methoxy-1-methyl-ethyl)-acetamide (dimethenamide, SAN-582), 2,4-dichlorophenoxyacetic acid (2,4-D), 2-amino-4-(1-fluoro-1-methyl-ethyl)-6-(1-methyl-2-(3,5-dimethyl-phenoxy)-ethylamino)-1,3,5-triazine (dimexyflam, IDH-1105), the sodium salt of N-(4,6-dimethoxy-pyrimidin-2-yl)-N'-(3-methoxycarbonyl-6-trifluoromethyl-pyridin-2-yl-sulphonyl)-urea (DPX-KE459), 6,7-dihydro-dipyrido[1,2-a:2',1'-c]pyrazinediium (diquat), S,S-dimethyl 2-difluoromethyl- 4-i-butyl-6-trifluoromethyl-pyridine-3, 5-dicarbothioate (dithiopyr), the sodium salt of N-(4,6-dimethoxy-pyrimidin-2-yl)-N'-(3-methoxycarbonyl-6-trifluoromethyl-pyridin-2-yl-sulphonyl)-urea (DPX-KE459), S-ethyl dipropylthiocarbamate (EPTC), S-(phenylmethyl) N-ethyl-N-(1,2-dimethyl-propyl)-thiocarbamate (esprocarb), ethyl [2-chloro-5-(4-chloro-5-difluoromethoxy-1-methyl-1H-pyrazol-3-yl)-4-fluoro-phenoxy]-acetate (ET-751), (S)-(2-ethoxy-1-methyl-2-oxoethyl) 2-chloro-5-(2-chloro-4-trifluoromethyl-phenoxy)-benzoate (ethoxyfen), N-(4,6-dimethoxy-pyrimidin-2-yl)-N'-(2-ethoxy-phenoxysulphonyl)-urea (ethoxysulfuron, HOE-095404), ethyl 2-[4-(6-chloro-benzoxazol-2-yl-oxy)-phenoxy]-propanoate (fenoxaprop-ethyl), isopropyl N-benzoyl-N-(3-chloro-4-fluoro-phenyl)-DL-alaninate (flamprop-isopropyl), isopropyl N-benzoyl-N-(3-chloro-4-fluorophenyl)-L-alaninate (flamprop-isopropyl-L), methyl N-benzoyl-N-(3-chlorofluoro-phenoxy)-DL-alaninate (flamprop-methyl), pentyl [2-chloro-4-fluoro-5-(1,3,4,5,6,7-hexahydro-1,3-dioxo-2H-isoindol-2-yl)-phenoxy]-acetate (flumiclorac-pentyl), ethoxycarbonylmethyl 5-(2-chloro-4-trifluoromethyl-5-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1-(2H)-pyrimidyl)-benzoate (flupropacil), 9-hydroxy-9H-fluorene-9-carboxylic acid (flurenol), (4-amino-3,5-chloro-fluoro-pyridin-2-yl-oxy)-acetic acid (fluroxypyr), N-(2,6-difluoro-phenyl)-5-methyl-1,2,4-triazolo[1,5-a]-pyrimidine-2-sulphonamide (flumetsulam, DE-498), methyl [(2-chloro-fluoro-5-(tetrahydro-3-oxo-1H,3H-[1,3,4]thiadiazolo-[3,4-a]-pyridazin-1-ylidene)-amino-phenyl]-thioacetate (fluthiacet-methyl, KIH-9201), 2-amino-4-(hydroxymethylphosphinyl)-butanoic acid (ammonium salt) (glufosinate-(ammonium)), N-phosphonomethyl-glycine (isopropylammonium), (glyphosate, -isopropylanmmonium), methyl-2-(4,5-dihydro-4-methyl-4-isopropyl-5-oxo-1H-imidazol-2-yl)-4-methyl-benzoate (imazamethabenz-methyl), 2-(4,5-hydromethyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo-[1,2-a]-pyridin-3-yl-sulphonyl)-urea (imazosulfuron), 4-hydroxy-3,5-diiodo-benzonitrile (ioxynil), N,N-dimethyl-N'-(4-isopropyl-phenyl)-urea (isoproturon), N-(3-(1-ethyl-1-methyl-3,5-propyl)-isoxazol-5-yl)-2,6-dimethoxy-benzamide (isoxaben), (5-cyclopropyl-isoxazol-4-yl)-(-methylsulphonyl-4-trifluoromethyl-phenyl)-methanone (isoxaflutole, RPA-201772) N'-(3,4-dichloro-phenyl)-N-methoxy-N-methylurea (linuron), (4-chloro-2-methyl-phenoxy)-acetic acid (MCPA), 2-(4-chloro-2-methyl-phenoxy)-propionic acid (mecoprop), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H-1-benzopyran-7-yl-oxy)-phenyl)-N-methoxy-N-methyl-urea (metobenzuron, UMP-488), N'-(4-bromo-phenyl)-N-methoxy-N-methylurea (metobromuron), 2-chloro-N-(2-ethyl-6-methyl-phenyl)-N-(2-methoxy-1-methyl-ethyl)-acetamide (metolachlor), N-(2,6-dichloro-3-methylphenyl)-5,7-dimethoxy-1,2,4-triazolo[1,5-a]-pyrimidine-2-sulpbonamide (metosulam, DE-511), N'-(3-chloro-4-methoxy-phenyl)-N,N-dimethyl-urea (metoxuron), 4-amino-6-tert-butyl-3-methylthio-1,2,4-triazin-5-(4H)-one (metribuzin), N-(4-methoxy-6-methyl-1,3,5-triazin-2-yl)-N'-(2-methoxycarbonyl-phenylsulphonyl)-urea (metsulfuron-methyl), 2-(2-naphthyloxy)-N-phenyl-propanamide (naproanilide), N-butyl-N'-(3,4-dichlorophenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), N-(4,6-dimethyl-pyrimidin-2-yl)-N'-(2-oxetan-3-yl-oxycarbonyl-phenyl-sulphonyl)-urea (oxasulfuron), 1,1'-dimethyl-4,4'-bipyridinium (paraquat), 1-amino-N-(1-ethyl-propyl)-3,4-dimethyl-2,6-dinitro-benzene (pendimethalin), N-(4,6-bis-difluoromethoxy-pyrimidin-2-yl)-N'-(2-methoxy-carbonyl-phenylphonyl)-urea (primisulfuron-methyl), S-phenylmethyl N,N-dipropyl-thiocarbamate (prosulfocarb), N-(4-methoxy-6-methyl-1,3,5-triazin-2-yl)-N-(2-(3,3,3-trifluoro-propyl)-phenylsulphonyl)-urea (prosulfuron), 2-chloro-N-(2,6-diethyl-phenyl)-N-(2-propoxy-ethyl)-acetamide (pretilachlor), 2-chloro-N-isopropyl-N-phenyl-acetamide (propachlor), O-(6-chloro-3-phenyl-pyridazin-4-yl) S-octyl thiocarbonate (pyridate), 4-(2,4-dichloro-benzoyl)-1,3-dimethyl-5-(4-methyl-phenylsulphonyloxy)-pyrazole (pyrazolate), 4-(2,4-dichloro-benzoyl-1,3-dimethyl-5-(phenylcarbonylmethoxy)-pyrazole (pyrazoxyfen), N-(4,6-dimethoxy-pyrimidin-2-yl)-N'-(4-ethoxycarbonyl-1-methyl-pyrazol-5-yl-sulphonyl)-urea (pyrazosulfuron-ethyl), 7-chloro-3-methyl-quinoline-8-carboxylic acid (quinmerac), N-(4,6-dimethoxypyrimidin-2-yl)-N'-(3-ethylsulphonyl-pyridin-2-yl-sulphonyl)-urea (rimsulfuron), 6-chloro-2,4-bis-ethylamino-1,3,5-triazine (simazin), 2-(2-chloro4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone, F-6285), N-phosphonomethyl-glycine-trimethylsulphonium (sulfosate), N-(4,6-dimethoxy-pyrimidin-2-yl)-N'-(2-ethylsulphonyl-imidazo[1,2-a]pyridine-3-sulphonamide (sulfosulfuron, MON-37500), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), 6-(6,7-dihydro-6,6-dimethyl-3H, 5H-pyrrolo[2,1-c]-1,2,4-thiadiazol-3-ylidenamino)-7-fluoro-4-(2-propinyl)-2H-1,4-benzoxazin-3(4H)-one (thidiazimin), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenyl-sulphonyl)-urea (tribenuron-methyl), 2-(3,5-dichloro-phenyl)-2-(2,2,2-trichloro-ethyl)-oxirane (tridiphane), 1-amino-2,6-dinitro-N,N-dipropyl-4-trifluoromethyl-benzene (trifluralin)-("active compounds of Group 2").

Of very particular interest are the selective herbicidal compositions according to the invention which are characterized by a content of an active compound combination comprising (a) an arylsulphonylaminocarbonyltriazolinone of the general formula (1), in which $R^1$ represents hydrogen, amino, represents in each case optionally cyano-, fluorine-, chlorine-, methoxy- or ethoxy-substituted methyl, ethyl, n- or i-propyl, n-, i-, s- or t-butyl, ethenyl, propenyl, butenyl, ethinyl, propinyl, butinyl, methoxy, ethoxy, n- or i-propoxy, n-, i-, s- or t-butoxy, propenyloxy, butenyloxy, methylamino, ethylamino, n- or i-propylamino, n-, i-, s- or t-butylamino, dimethylamino or diethylamino, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, difluoromethoxy- or trifluoromethoxy-substituted phenyl or benzyl, $R^2$ represents hydrogen, hydroxyl, mercapto, amino, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino, ethenyl, propenyl, butenyl, ethinyl, propinyl, butinyl, propenyloxy, butenyloxy, propinyloxy, butinyloxy, propenylthio, butenylthio, propinylthio, butinylthio, propenylamino, butenylamino, propinylamino or butinylamino, represents in each case optionally cyano-, fluorine-, chorine-, bromine-, methyl-, ethyl-, n- or i-propyl-substituted cyclopropyl, cyclobutyl, cyclopentyl, cycohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, difluoromethoxy- or trifluoromethoxy-substituted phenyl, phenoxy, phenylthio, phenylamino or benzyl, $R^3$ represents nitro, cyano, fluorine, chlorine, bromine, represents in each case optionally cyano, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamidno, n- or i-propylamino, n-, i-, s- or t-butylamino, ethenyl, propenyl, butenyl, propenyloxy, butenyloxy, propenylthio, butenylthio, propenylamino, butenylamino, ethynyl, propynyl, butynyl, propinyloxy, butinyloxy, propinylthio or butinylthio, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclobexyloxy, cyclopropylthio, cyclobutylthio, cyclopentylthio, cyclohexylthio, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy, phenylthio, phenylsulphinyl, phenylsulphonyl or phenylamino, and $R^4$ represents hydrogen, nitro, cyano, fluorine, chlorine, bromine, represents in each case optionally cyano-, fluorine-, chlorine- methoxy- or ethoxy-substituted substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethinyl, propinyl, butinyl, propinyloxy, butinyloxy, propinylthio or butinylthio, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, trifluoromethyl-, methoxy-, ethoxy-, n- or i-propoxy-, n-, i-, s- or t-butoxy-, difluoromethoxy- or trifluoromethoxy-substituted phenyl, phenoxy, phenylthio, phenylsulphinyl, phenylsulphonyl or phenylamino, and/or a salt of a compound of the formula (I) ("active compounds of Group 1") and (b) one or two compounds of a second group of herbicides which comprises the active compounds listed below:

2-chloro-N-(ethoxymethyl)-N-(2-ethyl-6-methyl-phenyl)-acetamide (acetochlor), 2-chloro-6-nitro-3-phenoxy-aniline (aclonifen), 2-chloro-N-(methoxymethyl)-N-( 2,6-diethyl-phenyl)-acetamide (alachlor), N-(4,6-dimethoxy-pyrimidin-2-yl)-N'-(N-methyl-N-methylsulphonyl-sulphamoyl)-urea (amidosulfuron), 6-chloro-4-ethylamino-2-isopropylamino-1,3,5-triazine (atrazine), ethyl N-benzoy-N-(3,4-dichloro-phenyl)-DL-alaninate (benzoylprop-ethyl), 3-i-propyl-1H-2,1,3-benzo-thiadiazin-4(3H)-one (bentazon), methyl 5-(2,4-dichloro-phenoxy)-2-nitro-benzoate (bifenox), 2-bromo-3,3-dimethyl-N-(1-methyl-1-phenyl-ethyl)-butanamide (bromobutide), 3,5-dibromo-4-hydroxy-benzaldehyde O-(2,4-dinitro-phenyl)-oxime (bromofenoxim), 3,5-dibromo-4-hydroxy-benzonitrile (bromoxynil), N-butoxymethyl-2-chloro-N-(2,6-diethyl-phenyl)-acetamide (butachlor), S-ethyl bis-(2-methyl-propyl)-thiocarbamate (butylate), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl, F-8426), 2,4-dichloro-1-(3-methoxy-4-nitro-phenoxy)-benzene (chlomethoxyfen), 3-amino-2,5-dichloro-benzoic acid (chloramben), 1,3,5-trichloro-2-(4-nitro-phenoxy)-benzene (chlomitrofen), N-(4-methoxy-6-methyl-1,3,5-triazin-2-yl)-N'-(2-chloro-phenylsulphonyl)-urea (chlorsulfuron), N'-(3-chloro-4-methylphenyl)-N,N-dimethyl-urea (chlortoluron), N-(4, 6-dimethoxy-1,3,5-triazin-2-yl)-N'-(2-(2-methoxy-ethoxy)-phenyl-sulphonyl)-urea (cinosulfuron), (R)-(2-propinyl)-2-[4-(5-chloro-3-fluoro-pyridin-2-yl-oxy)- phenoxy-propanoate (clodinafop-propargyl), 3,6-dichloro-pyridine-2-carboxylic acid (clopyralid), N-(4,6-dimethoxy-pyrimidin-2-yl)-N'-(3-chloro-4-methoxycarbonyl-1-methyl-pyrazol-5-yl-sulphonyl)-urea (clopyrasulfuron, halosulfuron, NC-319), methyl-3-chloro-2-[(5-ethoxy-7-fluoro[1,2,4]triazolo[1,5-c]pyrimidin-2-yl-sulphonyl)-amino]-3-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron, AC-322140), 3,6-dichloro-2-methoxy-benzoic acid (dicamba), (R)-2-(2,4-dichloro-phenoxy)-propionic acid (dichlorprop-P), methyl-2-[4-(2,4-dichloro-phenoxy)-phenoxy]-propionate (diclofopmethyl), 1,2-dimethyl-3,5-diphenyl-1H-pyrazolium methyl sulphate (difenzoquat), N-(2,4-difluoro-phenyl)-2-(3-trifluoromethyl-phenoxy)-pyridine-3-carboxamide (diflufenican), 2-chloro-N-(2,4-dimethyl-3-thienyl)-N-(2-methoxy-1-methyl-ethyl)-acetamide (dimethenamide, SAN-582), 2,4-dichlorophenoxyacetic acid (2,4-D), 2-amino-4-(1-fluoro-1-methyl-ethyl)-6-(1-methyl-2-(3,5-dimethyl-phenoxy)-ethylamino)-1,3,5-triazine (dimexyflam, IDH-1105), 6,7-dihydro-dipyrido[1,2-a:2',1'-c]pyrazinediium (diquat), S,S-dimethyl 2-difluoromethyl-4-i-butyl-6-trifluoromethyl-pyridine-3,5-dicarbothioate (dithiopyr), the sodium salt of N-(4,6-dimethoxy-pyrimidin-2-yl)-N'-(3-methoxycarbonyl-6-trifluoromethyl-pyridin-2-yl-sulphonyl)-urea (DPX-KE-459), S-ethyl dipropylthiocarbamate (EPTC), S-(phenylmethyl) N-ethyl-N-(1,2-dimethyl-propyl)-thiocarbamate (esprocarb), ethyl [2-chloro-5-(4-chloro-5-difluoromethoxy-1-methyl-1H-pyrazol-3-yl)-4-fluoro-phenoxy]-acetate (ET-751), (S)-(2-ethoxy-1-methyl-2-oxoethyl) 2-chloro-5-(2-chloro-4-trifluoromethyl-phenoxy)-benzoate (ethoxyfen), N-(4,6-dimethoxy-pyrimidin-2-yl)-N'-(2-ethoxy-phenoxysulphonyl)-urea (ethoxysulfuron, HOE-095404), ethyl 2-[4-(6-chloro-benzoxazol-2-yl-oxy)-phenoxy]-propanoate (fenoxaprop-ethyl), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), pentyl[2-chloro-4-fluoro-5-(1,3,4,5,6,7-hexahydro-1,3-dioxo-2H-isoindol-2-yl)-phenoxy]-acetate (flumiclorac-pentyl), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1(2H)-pyrimidyl)-benzoate (flupropacil), 9-hydroxy-9H-fluorene-9-carboxylic acid (flurenol), (4-amino-3,5-dichloro-6-fluoro-pyridin-2-yl-oxy)-acetic acid (fluroxypyr), N-(2,6-fluoro-phenyl)-5-methyl-1,2,4-triazolo[1,5-a]-pyrimidine-2-sulphonamide (flumetsulam, DE-498), methyl[(2-chloro-4-fluoro-5-(tetrahydro-3-oxo-1H,3-H-[1,3,4]-thiadiazolo-[3,4-a]-pyridazin-1-ylidene)-amino-phenyl]-thioacetate (fluthiacet-methyl, KIH-9201), 2-amino-4-(hydroxymethylphosphinyl)-butanoic acid (ammonium salt) (glufosinate-(ammonium)), N-phosphonomethyl-glycine (isopropylammonium), (glyphosate, -isopropylammonium), methyl-2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (5-cyclopropyl-isoxazol-4-yl)-(2-methylsulphonyl-4-trifluoromethyl-phenyl)-methanone (isoxaflutole, RPA-201772), N'-(3,4-dichloro-phenyl)-N-methoxy-N-methylurea (linuron), (4-chloro-2-methyl-phenoxy)-acetic acid (MCPA), 2-(4-chloro-2-methyl-phenoxy)-propionic acid (mecoprop), 2-chloro-N-(2,6-dimethyl-phenyl)-N-(1H-pyrazol-1-yl-methyl)-acetamide (metazachlor), N'-(4-(3,4-dihydro-2-methoxy- 2,4,4-trimethyl-2H-1-benzopyran-7-yl-oxy)-phenyl)-N-methoxy-N-methyl-urea (metobenzuron, UMP-488), N'-(4-bromo-phenyl)-N-methoxy-N-methylurea (metobromuron), 2-chloro-N-(2-ethyl-6-methyl-phenyl)-N-(2-methoxy-1-methyl-ethyl)-acetamide (metolachlor), N-(2,6-dichloro-3-methyl-phenyl)-5,7-dimethoxy-1,2,4-triazolo[1,5-a]-pyrimidine-2-sulphonamide (metosulam, DE-511), N'-(3-chloro-4-methoxy-phenyl)-N,N-dimethyl-urea (metoxuron), 4-amino-6-tert-butyl-3-methylthio-1,2,4-triazin-5-(4H)-one (metribuzin), N-(4-methoxy-6-methyl- 1,3,5-triazin-2-yl)-N'-(2-methoxycarbonyl-phenylsulphonyl)-urea (metsulfuron-methyl), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), N-(4,6-dimethyl-pyrimidin-2-yl)-N'-(2-oxetan-3-yl-oxycarbonyl-phenylsulphonyl)-urea (oxasulfuron), 1,1'-dimethyl-4,4'-bipyridinium (paraquat), 1-amino-N-( 1-ethyl-propyl)-3,4-dimethyl-2,6-dinitro-benzene (pendimethalin), N-(4,6-bis-difuoromethoxy-pyrimidin-2-yl)-N'-(2-methoxycarbonyl-phenylsulphonyl)-urea (primisulfuron-methyl), S-phenylmethyl N,N-dipropyl-thiocarbamate (prosulfocarb), N-(4-methoxy-6-methyl- 1,3,5-triazin-2-yl)-N'-(2-(3,3,3-trifluoro-propyl)-phenylsulphonyl)-urea (prosulfuron), 2-chloro-N-(2,6-diethyl-phenyl)-N-(2-propoxy-ethyl)-acetamide (pretilachlor), 2-chloro-N-isopropyl-N-phenyl-acetamide (propachlor), O-(6-chloro-3-phenyl-pyridazin-4-yl) S-octyl thiocarbonate (pyridate), 4-(2,4-dichloro-benzoyl)- 1,3-dimethyl-5-(4-methyl-phenylsulphonyloxy)-pyrazole (pyrazolate), 4-(2, 4-dichloro-benzoyl- 1,3-dimethyl-5-(phenylcarbonylmethoxy)-pyrazole (pyrazoxyfen), N-(4, 6-dimethoxy-pyrimidin-2-yl)-N'-(4-ethoxycarbonyl-1-methyl-pyrazol-5-yl-sulphonyl)urea (pyrazosulfuron-ethyl), 7-chloro-3-methyl-quinoline-8-carboxylic acid (quinmerac), N-(4,6-dimethoxy-pyridin-2-yl)-N'-(3-ethylsulphonyl-pyridin-2-yl-sulphonyl)-urea (rimsulfuron), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone, F-6285), N-phosphonomethyl-glycine-trimethylsulphonium (sulfosate), N-(4,6-dimethoxy-pyrimidin-2-yl)-N'-(2-ethylsulphonyl-imidazo[1,2-a]

pyridine-3-sulphonamide (sulfosulfuron, MON-37500), 6-chloro-4-ethylamino-2-tert-butylamino- 1,3,5-triazine (terbuthylazine), 2-tert-butylamino-4-ethylamino-6-methylthio- 1,3,5-triazine (terbutryn), 2-chloro-N-(2,6-dimethyl-phenyl)-N-(3-methoxy-2-thienyl-methyl)-acetamide (thenylchlor), 6-(6,7-dihydro-6,6-dimethyl-3H, 5H-pyrrolo[2,1-c]-1,2,4-thiadiazol-3-ylidenamino)-7-fluoro-4-(2-propinyl)-2H-1,4-benzoxazin-3(4H)-one (thidiazimin), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), 2-(3,5-dichloro-phenyl)2-(2,2,-trichloro-ethyl)-oxirane (tridiphane), 1-amino-2,6-dinitro-N,N-dipropyl4-trifluoromethyl-benzene (trifluralin)-("active compounds of Group 2").

Instead of the pure active compounds of the formula (I), it is also possible to employ salts of the compounds of the formula (I) with metals and/or with basic nitrogen compounds in the active compound combinations according to the invention.

Here, preference is given to salts of the compounds of the formula (I) with alkali metals, such as, for example, lithium, sodium, potassium, rubidium or caesium, very particularly with sodium or potassium, with alkaline earth metals, such as, for example, magnesium, calcium or barium, very particularly with calcium, or with earth metals, such as, for example, aluminium Furthermore, preference is given to salts of the compounds of the formula (I) with ammonia, with $C_1$–$C_6$-alkyl-amines, such as, for example, with methylamine, ethylamine, n- or i-propylamine, n-, i-, s- or t-butylamine, n-, i-, s- or t-pentylamine, with di-($C_1$–$C_6$-alkyl)-amines, such as, for example, dimethylamine, diethylamine, dipropylamine, diisopropylamine, dibutylamine, diisobuylamine, di-s-butylamine, diphenylamine, diisopentylamine, di-s-pentylamine and dihexylamine, with tri-($C_1$–$C_4$-alkyl)-amines, such as, for example, trimethylamine, triethylamine, tripropylamine, tributylamine and N-ethyl-diisopropylamine, with $C_3$–$C_6$-cycloalkyl-amines, such as, for example, cyclopentylamine or cyclohexylamine, with di-($C_3$–$C_6$-cycloalkyl)-amines, such as, for example, dicyclopentylamine or dicyclohexylamine, with N-$C_1$–$C_4$-alkyl-$C_3$–$C_6$-cycloalkylamines, such as, for example, N-methyl-cyclopentylamine, N-ethyl-cyclopentylamine, N-methyl-cyclohexylamine or N-ethyl-cyclohexylamine, with N,N-di-($C_1$–$C_4$-alkyl)-$C_3$–$C_6$-cycloalkyl-amines, such as, for example, N,N-dimethyl-cyclopentylamine, N,N-diethyl-cyclopentylamine, N,N-dimethyl-cyclohexylamine or N,N-diethyl-cyclohexylamine, with N-$C_1$–$C_4$-alkyl-di-($C_3$–$C_6$-cycloalkyl)-amines, such as, for example, N-methyl-dicyclopentylamine, N-ethyl-dicyclopentylamine, N-methyl-dicyclohexylamine or N-ethyl-dicyclohexylamine, with phenyl-$C_1$–$C_4$-alkyl-amines, such as, for example, benzylamine, 1-phenyl-ethylamine or 2-phenyl-ethylamine, with N-$C_1$–$C_4$-alkyl-phenyl-$C_1$–$C_4$-alkyl-amines, such as, for example, N-methyl-benzylamine or N-ethyl-benzylamine, or with N,N-di-($C_1$–$C_4$-alkyl)-phenyl-$C_1$–$C_4$-alkyl-amines, such as, for example, N,N-dimethyl-benzylamine or N,N-diethylbenzylamine, or with optionally fused and/or $C_1$–$C_4$-alkyl-substituted azines, such as, for example, pyridine, quinoline, 2-methyl-pyridine, 3-methyl-pyridine, 4-methyl-pyridine, 2,4-dimethyl-pyridine, 2,5-dimethyl-pyridine, 2,6-dimethyl-pyridine or 5-ethyl-2-methyl-pyridine.

Basic compounds which may be employed for preparing the salt of the compounds of the formula (I) which can be employed according to the invention which may be mentioned are:

alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide.

Examples of the compounds of the formula (I) to be used as mixing partners according to the invention which may be mentioned are:

2-(2-chloro-phenylsulphonylaminocarbonyl)-, 2-(2-bromo-phenylsulphonylaminocarbonyl)-, 2-(2-methyl-phenylsulphonylaminocarbonyl)-, 2-(2-ethyl-phenylsulphonyl-aminocarbonyl)-, 2-(2-n-propyl-phenylsulphonylaminocarbonyl), 2-(2-i-propyl-phenylsulphonylaminocarbonyl), 2-(2-trifluoromethyl-phenylsulphonylaminocarbonyl)-, 2-(2-methoxy-phenylsulphonylaminocarbonyl)-, 2-(2-ethoxy-phenylsulphonylaminocarbonyl)-, 2-(2-n-propoxy-phenylsulphonylaminocarbonyl)-, 2-(2-i-propoxy-phenylsulphonylaminocarbonyl)-, 2-(2-difluoromethoxy-phenylsulphonylaminocarbonyl)-, 2-(2-trifluoromethoxy-phenylsulphonylaminocarbonyl)-, 2-(2-methoxycarbonyl-phenylsulphonylaminocarbonyl)-, 2-(2-ethoxycarbonyl-phenylsulphonylaminocarbonyl)-, 2-(2-n-propoxycarbonyl-phenylsulphonylaminocarbonyl)-, 2-(2-i-propoxycarbonyl-phenylsulphonylaminocarbonyl)- and 2-(2-chloro-6-methyl-phenylsulphonylaminocarbonyl)-4-methyl-5-methoxy-2,4-dihydro-3H-1,2,4-triazol-3-one, 4-methyl-5-ethoxy-2,4-dihydro-3H-1,2,4-triazol-3-one, -4-methyl-5-n-propoxy-2,4-dihydro-3H-1,2,4-triazol-3-one, -4-methyl-5-i-propoxy-2,4-dihydro-3H-1,2,4-triazol-3-one, 4-methyl-5-trifluoroethoxy-2,4-dihydro-3H-1,2,4-triazol-3-one, -4-methyl-5-methylthio-2,4-dihydro-3H-1,2,4-triazol-3-one, -4-methyl-5-ethylthio-2,4-dihydro-3H-1,2,4-triazol-3-one, -4-methoxy-5-methyl-2,4-dihydro-3H-1,2,4-triazol-3-one, -4-methoxy-5-ethyl-2,4-dihydro-3H-1,2,4-triazol-3-one, -4-methoxy-5-n-propyl-2,4-dihydro-3H-1,2,4-triazol-3-one, -4-cyclopropyl-5-methoxy-2,4-dihydro-3H-1,2,4-triazol-3-one, -4-cyclopropyl-5-ethoxy-2,4-dihydro-3H-1,2,4-triazol-3-one, -4-cyclopropyl-5-n-propoxy-2,4-dihydro-3H-1,2,4-triazol-3-one, -4-cyclopropyl-5-i-propoxy-2,4-dihydro-3H-1,2,4-triazol-3-one and -4-cyclopropyl-5-trifluoroethoxy-2,4-dihydro-3H-1,2,4-triazol-3-one and also the sodium and potassium salts of these compounds.

Mixing components of the formula (I) which may be particularly emphasized are the compounds 2-(2-methoxycarbonyl-phenylsulphonylaminocarbonyl)-4-methyl-5-n-propoxy-2,4-dihydro-3H-1,2,4-triazol-3-one (I-1) and 2-(2-trifluoromethoxy-phenylsulphonylaminocarbonyl)-4-methyl-5-methoxy-2,4-dihydro-3H-1,2,4-triazol-3-one (I-2) and their sodium salts (I-1, Na salt), (I-2, Na salt).

The compounds of the formula (I) are described in the abovementioned patent applications or patent specifications.

Mixing components from the active compounds of Group 2 which may be particularly emphasized are:

amidosulfuron, bentazon, bromoxynil, carfentrazone(-ethyl), clodinafop(-propargyl), clopyralid, chlorsulfuron, chlortoluron, cyclosulfamuron, 2,4-D, diclofop(-methyl), difenzoquat, diflufenican, DPX-KE459, ET-751, ethoxyfen, fenoxaprop(-ethyl), fluoroglycofen(-ethyl), flupropacil, fluroxypyr, isoproturon, mecoprop, metosulam, metribuzin, metsulfuron(-methyl), pendimethalin, prosulfocarb, pyridate, sulfosulfuron, thifensulfuron(-methyl), tralkoxydim, triasulfuron, tribenuron(-methyl) or trifluralin.

From this group, metribuzin is of very particular interest as a mixing component.

Surprisingly, it has now been found that the above-described active compound combinations of the arylsulphonylaminocarbonyltriaozolinones of the formula (I) and the abovementioned active compounds of Group 2, in addition to being very well tolerated by useful plants, have particularly high herbicidal activity and can be used in a variety of crops, in particular in wheat, but additionally also in maize, barley and rice, for the selective control of weeds.

Surprisingly, the herbicidal activity of the active compound combinations according to the invention of compounds of the abovementioned groups 1 and 2 is considerably higher than the sum of the effects of the individual compounds.

This means that there exists not only a complementary action but also an unforeseeable synergistic effect. The novel active compound combinations are tolerated well by a large number of crops, and the novel active compound combinations also effectively control weeds which are otherwise difficult to control. The novel active compound combinations are therefore a valuable addition to the selective herbicides.

The active compound combinations according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera and Phalaris.

Monocotyledonous crops of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

At specific concentration ratios, the synergistic effect of the active compound combinations according to the invention is particularly pronounced. However, the ratios by weight of the active compounds in the active compound combinations can be varied within relatively wide ranges. In general, 0.01 to 1000 parts by weight, preferably 0.05 to 500 parts by weight and particularly preferably 0.1 to 100 parts by weight of active compound of Group 2 are used per part by weight of active compound of the formula (I).

The active compound combinations can be converted into the customary formulations, such as solutions, emulsions, wettable powders, suspensions, powders, dusts, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water it is also possible to use, for example, organic solvents as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as finely divided silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; as dispersing agents there are suitable: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight, preferably between 0.5 and 90%, of active compounds.

In general, the active compound combinations according to the invention are applied in the form of ready mixes. However, the active compounds which the active compound combinations comprise can also be formulated individually and mixed upon use, i.e. applied in the form of tank mixes.

The novel active compound combinations can be used as such or in the form of their formulations, and furthermore also as mixtures with other known herbicides, ready mixes or tank mixes again being possible. They may also be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium thiocyanate, as further additives.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound combinations according to the invention can be applied before and after the plants have emerged, that is to say pre-emergence and post-emergence. They can also be incorporated into the soil before sowing.

The good herbicidal activity of the novel active compound combinations can be seen from the examples which follow. While the individual active compounds show weak points regarding the herbicidal activity, the combinations, without exception, display a very good activity against weeds, which exceeds a simple additive effect.

A synergistic effect in herbicides is always present when the herbicidal activity of the active compound combination exceeds the activity of the active compounds when applied individually.

The expected activity for a given combination of two herbicides can be calculated as follows (cf. COLBY, S. R.: "Calculating synergistic and antagonistic responses of herbicide combinations", Weeds 15, pages 20–22, 1967):

If X=% damage caused by herbicide A (active compound of the formula I) at application rate of p kg/ha and Y=% damage caused by herbicide B (active compound of the formula II) at application rate of q kg/ha and E=the expected damage of herbicides A and B at application rates of p and q kg/ha, then E=X+Y−(X*Y/100).

If the actual damage exceeds the calculated figure, the activity of the combination is superadditive, i.e. it shows a synergistic effect.

It can be seen from the examples which follow that the observed herbicidal activity of the active compound combinations according to the invention in the weeds exceeds the calculated activity, i.e. that the novel active compound combinations act synergistically.

EXAMPLE A

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular desired amounts of active compound are applied per unit area. The concentration of the spray liquor is chosen such that the particular desired amounts of active compound are applied in 1000 l of water/ha. After three weeks, the degree of damage to the plants is rated visually in % damage in comparison to the development of the untreated control.

The figures denote:

0%=no effect (like untreated control)

100%=total destruction.

Active compounds, application rates, test plants and results are shown in Table A-1 and A-2 below, the abbreviations used in the table having the following meanings:

(I-1, Na salt)=sodium salt of 2-(2-methoxycarbonyl-phenylsulphonylaminocarbonyl)-4-methyl-5-n-propoxy-2,4-dihydro-3H-1,2,4-triazol-3-one (I-1);

(I-2, Na salt)=sodium salt of 2-(2-trifluoromethoxy-phenylsulphonylaminocarbonyl)-4-methyl-5-methoxy-2,4-dihydro-3H-1,2,4-triazol-3-one (I-2);

found=damage or effect (in %) found;

calc.=damage or effect (in %) calculated using Colby's formula.

TABLE A-1

Post-emergence test/greenhouse

| Active compound or active compound combination | Application rate g/ha (active compound) | Test plants damage or effect in % | | | |
|---|---|---|---|---|---|
| | | Aspera spica-Venti | | Bromus secalinus | |
| | | found | calc. | found | calc. |
| metribuzin - known - | 60 | 20 | | 0 | |
| (I-1, Na salt) - known - | 15 | 70 | | 60 | |
| metribuzin + (I-1, Na salt) - according to the invention - | 60 + 15 | 95 | 76 | 80 | 60 |

TABLE A-2

Post-emergence test/greenhouse

| Active compound or active compound combination | Application rate g/ha (active compound) | Test plants damage or effect in % | | | |
|---|---|---|---|---|---|
| | | Aspera spica-Venti | | Bromus secalinus | |
| | | found | calc. | found | calc. |
| metribuzin - known - | 60 | 20 | | 50 | |
| (I-2, Na salt) - known - | 15 | 60 | | 90 | |
| metribuzin + (I-2, Na salt) - according to the invention - | 60 + 15 | 98 | 68 | 100 | 95 |

Appendix I
Declaration and test data,
signed by Dr. Dieter Feucht
and dated 10-09-2000
(94 pages)

Post-emergence/greenhouse

Table B-1:

|  | Applic. rate (g ai./ha) | AVENA FATUA found | AVENA FATUA calc. |
|---|---|---|---|
| (I-1, Na salt) | 60 | 60 |  |
| Imazametabenz | 250 | 70 |  |
| (I-1, Na salt) + Imazametabenz | 60 + 250 | 95 | 88 |

Table B-2:

|  | Applic. rate (g ai./ha) | BROMUS SECALINUS found | BROMUS SECALINUS calc. |
|---|---|---|---|
| (I-1, Na salt) | 60 | 90 |  |
| Imazametabenz | 250<br>125 | 0<br>0 |  |
| (I-1, Na salt) + Imazametabenz | 60 + 250<br>60 + 125 | 95<br>95 | 90<br>90 |

Table B-3:

|  | Applic. rate (g ai./ha) | DIGITARIA SANGUINALIS found | DIGITARIA SANGUINALIS calc. |
|---|---|---|---|
| (I-1, Na salt) | 60 | 30 | |
|  | 30 | 20 | |
| Imazametabenz | 250 | 40 | |
|  | 125 | 30 | |
| (I-1, Na salt) + Imazametabenz | 60 + 250 | 90 | 58 |
|  | 60 + 125 | 80 | 51 |
|  | 30 + 125 | 80 | 44 |

Table B-4:

|  | Applic. rate (g ai./ha) | ERIOCHLOA VILLOSA found | ERIOCHLOA VILLOSA calc. |
|---|---|---|---|
| (I-1, Na salt) | 15 | 0 | |
| Imazametabenz | 125 | 0 | |
| (I-1, Na salt) + Imazametabenz | 15 + 125 | 60 | 0 |

Table B-5:

|  | Applic. rate (g ai./ha) | LOLIUM PERENNE found | LOLIUM PERENNE calc. |
|---|---|---|---|
| (I-1, Na salt) | 60 | 50 | |
|  | 30 | 20 | |
|  | 15 | 0 | |
| Imazametabenz | 250 | 10 | |
|  | 125 | 0 | |
| (I-1, Na salt) + Imazametabenz | 30 + 250 | 60 | 28 |
|  | 60 + 125 | 70 | 50 |
|  | 30 + 125 | 60 | 20 |
|  | 15 + 125 | 40 | 0 |

Table B-6:

|  | Applic. rate (g ai./ha) | ABUTILON THEOPHRASTI found | ABUTILON THEOPHRASTI calc. |
|---|---|---|---|
| (I-1, Na salt) | 60<br>15 | 50<br>20 |  |
| Imazametabenz | 250 | 70 |  |
| (I-1, Na salt) + Imazametabenz | 60 + 250<br>15 + 250 | 95<br>90 | 85<br>76 |

Table B-7:

|  | Applic. rate (g ai./ha) | DATURA STRAMONIUM found | DATURA STRAMONIUM calc. |
|---|---|---|---|
| (I-1, Na salt) | 60<br>30 | 80<br>60 |  |
| Imazametabenz | 250 | 80 |  |
| (I-1, Na salt) + Imazametabenz | 60 + 250<br>30 + 250 | 100<br>100 | 96<br>92 |

Table B-8:

|  | Applic. rate (g ai./ha) | IPOMOEA HEDERACEA found | IPOMOEA HEDERACEA calc. |
|---|---|---|---|
| (I-1, Na salt) | 60<br>30 | 70<br>70 |  |
| Imazametabenz | 125 | 0 |  |
| (I-1, Na salt) + Imazametabenz | 60 + 125<br>30 + 125 | 90<br>90 | 70<br>70 |

Table B-9:

|  | Applic. rate (g ai./ha) | POLYGONUM CONVOLVULUS found | POLYGONUM CONVOLVULUS calc. |
|---|---|---|---|
| (I-1, Na salt) | 60 | 0 | |
|  | 15 | 0 | |
| Imazametabenz | 250 | 80 | |
| (I-1, Na salt) + Imazametabenz | 15 + 250 | 95 | 80 |
|  | 60 + 125 | 90 | 70 |
|  | 30 + 125 | 95 | 70 |
|  | 15 + 125 | 95 | 70 |

Table B-10:

|  | Applic. rate (g ai./ha) | VIOLA ARVENSIS found | VIOLA ARVENSIS calc. |
|---|---|---|---|
| (I-1, Na salt) | 15 | 50 | |
| Imazametabenz | 125 | 0 | |
| (I-1, Na salt) + Imazametabenz | 15 + 125 | 70 | 50 |

Table B-11:

|  | Applic. rate (g ai./ha) | XANTHIUM STRUMARIUM found | XANTHIUM STRUMARIUM calc. |
|---|---|---|---|
| (I-1, Na salt) | 60 | 90 | |
|  | 30 | 80 | |
| Imazametabenz | 250 | 0 | |
|  | 125 | 0 | |
| (I-1, Na salt) + Imazametabenz | 60 + 250 | 95 | 90 |
|  | 30 + 125 | 95 | 80 |

Table B-12:

|  | Applic. rate (g ai./ha) | AVENA FATUA found | AVENA FATUA calc. |
|---|---|---|---|
| (I-1, Na salt) | 30 | 50 |  |
| Sulfosulfuron | 4 | 60 |  |
| (I-1, Na salt) + Sulfosulfuron | 30 + 4 | 95 | 80 |

Table B-13:

|  | Applic. rate (g ai./ha) | DIGITARIA SANGUINALIS found | DIGITARIA SANGUINALIS calc. |
|---|---|---|---|
| (I-1, Na salt) | 60<br>15 | 30<br>0 |  |
| Sulfosulfuron | 4 | 30 |  |
| (I-1, Na salt) + Sulfosulfuron | 60 + 4<br>15 + 4 | 80<br>80 | 51<br>30 |

Table B-14:

|  | Applic. rate (g ai./ha) | LOLIUM PERENNE found | LOLIUM PERENNE calc. |
|---|---|---|---|
| (I-1, Na salt) | 30 | 20 |  |
| Sulfosulfuron | 4 | 40 |  |
| (I-1, Na salt) + Sulfosulfuron | 30 + 4 | 80 | 52 |

Table B-15:

|  | Applic. rate (g ai./ha) | CASSIA TORA found | CASSIA TORA calc. |
|---|---|---|---|
| (I-1, Na salt) | 60 | 30 | |
| Sulfosulfuron | 4 | 70 | |
| (I-1, Na salt) + Sulfosulfuron | 60 + 4 | 95 | 79 |

Table B-16:

|  | Applic. rate (g ai./ha) | POLYGONUM CONVOLVULUS found | POLYGONUM CONVOLVULUS calc. |
|---|---|---|---|
| (I-1, Na salt) | 60 | 0 | |
| Sulfosulfuron | 8 | 90 | |
| (I-1, Na salt) + Sulfosulfuron | 60 + 8 | 95 | 90 |

Table B-17:

|  | Applic. rate (g ai./ha) | AVENA FATUA found | AVENA FATUA calc. |
|---|---|---|---|
| (I-1, Na salt) | 60<br>30 | 60<br>50 | |
| Tribenuron-methyl | 8<br>4 | 0<br>0 | |
| (I-1, Na salt) + Tribenuron-methyl | 60 + 8<br>30 + 8<br>30 + 4 | 90<br>90<br>80 | 60<br>50<br>50 |

Table B-18:

|  | Applic. rate (g ai./ha) | ECHINOCHLOA CRUS-GALLI found | ECHINOCHLOA CRUS-GALLI calc. |
|---|---|---|---|
| (I-1, Na salt) | 30 | 90 |  |
| Tribenuron-methyl | 8 | 60 |  |
| (I-1, Na salt) + Tribenuron-methyl | 30 + 8 | 99 | 96 |

Table B-19:

|  | Applic. rate (g ai./ha) | LOLIUM PERENNE found | LOLIUM PERENNE calc. |
|---|---|---|---|
| (I-1, Na salt) | 60<br>30 | 50<br>20 |  |
| Tribenuron-methyl | 8 | 0 |  |
| (I-1, Na salt) + Tribenuron-methyl | 60 + 8<br>30 + 8 | 70<br>60 | 50<br>20 |

Table B-20:

|  | Applic. rate (g ai./ha) | AVENA FATUA found | AVENA FATUA calc. |
|---|---|---|---|
| (I-1, Na salt) | 60<br>30 | 60<br>50 |  |
| Amidosulfuron | 15<br>8 | 0<br>0 |  |
| (I-1, Na salt) + Amidosulfuron | 60 + 15<br>30 + 15<br>60 + 8<br>30 + 8 | 80<br>70<br>80<br>70 | 60<br>50<br>60<br>50 |

Table B-21:

|  | Applic. rate (g ai./ha) | DIGITARIA SANGUINALIS found | DIGITARIA SANGUINALIS calc. |
|---|---|---|---|
| (I-1, Na salt) | 60 | 30 |  |
| Amidosulfuron | 15 | 0 |  |
| (I-1, Na salt) + Amidosulfuron | 60 + 15 | 70 | 30 |

Table B-22:

|  | Applic. rate (g ai./ha) | CASSIA TORA found | CASSIA TORA calc. |
|---|---|---|---|
| (I-1, Na salt) | 15 | 0 |  |
| Amidosulfuron | 15 | 80 |  |
| (I-1, Na salt) + Amidosulfuron | 15 + 15 | 95 | 80 |

Table B-23:

|  | Applic. rate (g ai./ha) | POLYGONUM CONVOLVULUS found | POLYGONUM CONVOLVULUS calc. |
|---|---|---|---|
| (I-1, Na salt) | 15 | 0 |  |
| Amidosulfuron | 15 | 80 |  |
| (I-1, Na salt) + Amidosulfuron | 15 + 15 | 95 | 80 |

Table B-24:

|  | Applic. rate (g ai./ha) | VIOLA ARVENSIS found | VIOLA ARVENSIS calc. |
|---|---|---|---|
| (I-1, Na salt) | 15 | 50 |  |
| Amidosulfuron | 15 | 0 |  |
| (I-1, Na salt) + Amidosulfuron | 15 + 15 | 80 | 50 |

Table B-25:

|  | Applic. rate (g ai./ha) | ALOPECURUS MYOSUROIDES found | ALOPECURUS MYOSUROIDES calc. |
|---|---|---|---|
| (I-1, Na salt) | 60 | 90 |  |
| Metosulam | 8 | 10 |  |
| (I-1, Na salt) + Metosulam | 60 + 8 | 95 | 91 |

Table B-26:

|  | Applic. rate (g ai./ha) | AVENA FATUA found | AVENA FATUA calc. |
|---|---|---|---|
| (I-1, Na salt) | 60 | 60 |  |
|  | 30 | 50 |  |
|  | 15 | 50 |  |
| Metosulam | 8 | 0 |  |
|  | 4 | 0 |  |
| (I-1, Na salt) + Metosulam | 60 + 8 | 80 | 60 |
|  | 30 + 4 | 70 | 50 |
|  | 15 + 4 | 70 | 50 |

Table B-27:

|  | Applic. rate (g ai./ha) | BROMUS SECALINUS found | BROMUS SECALINUS calc. |
|---|---|---|---|
| (I-1, Na salt) | 60 | 90 |  |
| Metosulam | 8 | 0 |  |
| (I-1, Na salt) + Metosulam | 60 + 8 | 95 | 90 |

Table B-28:

|  | Applic. rate (g ai./ha) | ECHINOCHLOA CRUS-GALLI found | ECHINOCHLOA CRUS-GALLI calc. |
|---|---|---|---|
| (I-1, Na salt) | 60 | 90 |  |
| Metosulam | 8<br>4 | 10<br>0 |  |
| (I-1, Na salt) + Metosulam | 60 + 8<br>60 + 4 | 100<br>95 | 91<br>90 |

Table B-29:

|  | Applic. rate (g ai./ha) | CASSIA TORA found | CASSIA TORA calc. |
|---|---|---|---|
| (I-1, Na salt) | 30<br>15 | 0<br>0 |  |
| Metosulam | 4 | 90 |  |
| (I-1, Na salt) + Metosulam | 30 + 4<br>15 + 4 | 95<br>95 | 90<br>90 |

Table B-30:

|  | Applic. rate (g ai./ha) | DATURA STRAMONIUM found | DATURA STRAMONIUM calc. |
|---|---|---|---|
| (I-1, Na salt) | 30 | 60 |  |
| Metosulam | 4 | 80 |  |
| (I-1, Na salt) + Metosulam | 30 + 4 | 99 | 92 |

Table B-31:

|  | Applic. rate (g ai./ha) | ECHINOCHLOA CRUS-GALLI found | ECHINOCHLOA CRUS-GALLI calc. |
|---|---|---|---|
| (I-1, Na salt) | 60 | 90 |  |
| Flurtamone | 60 | 60 |  |
| (I-1, Na salt) + Flurtamone | 60 + 60 | 99 | 96 |

Table B-32:

|  | Applic. rate (g ai./ha) | AVENA FATUA found | AVENA FATUA calc. |
|---|---|---|---|
| (I-1, Na salt) | 30 | 95 |  |
|  | 15 | 95 |  |
| Butoxyethanolester (2,4-D-Ester; Weedone) | 250 | 0 |  |
|  | 125 | 0 |  |
| (I-1, Na salt) + Butoxyethanolester (2,4-D-Ester; Weedone) | 30 + 250 | 98 | 95 |
|  | 15 + 250 | 98 | 95 |
|  | 30 + 125 | 98 | 95 |
|  | 15 + 125 | 98 | 95 |

Table B-33:

|  | Applic. rate (g ai./ha) | BROMUS SECALINUS found | BROMUS SECALINUS calc. |
|---|---|---|---|
| (I-1, Na salt) | 30 | 95 | |
| | 15 | 95 | |
| Butoxyethanolester (2,4-D-Ester; Weedone) | 250 | 40 10 | |
| (I-1, Na salt) + Butoxyethanolester (2,4-D-Ester; Weedone) | 30 + 250 15 + 250 | 100 100 | 97 97 |

Table B-34:

|  | Applic. rate (g ai./ha) | ABUTILON THEOPHRASTI found | ABUTILON THEOPHRASTI calc. |
|---|---|---|---|
| (I-1, Na salt) | 15 | 0 | |
| Butoxyethanolester (2,4-D-Ester; Weedone) | 250 | 60 | |
| (I-1, Na salt) + Butoxyethanolester (2,4-D-Ester; Weedone) | 15 + 250 | 80 | 60 |

Table B-35:

|  | Applic. rate (g ai./ha) | SOLANUM NIGRUM found | SOLANUM NIGRUM calc. |
|---|---|---|---|
| (I-1, Na salt) | 30 | 50 | |
| | 15 | 50 | |
| Butoxyethanolester (2,4-D-Ester; Weedone) | 250 | 90 | |
| | 125 | 80 | |
| (I-1, Na salt) + Butoxyethanolester (2,4-D-Ester; Weedone) | 30 + 250 15 + 250 30 + 125 15 + 125 | 98 98 98 98 | 95 95 90 90 |

Table B-36:

|  | Applic. rate (g ai./ha) | ALOPECURUS MYOSUROIDES found | ALOPECURUS MYOSUROIDES calc. |
|---|---|---|---|
| (I-2, Na salt) | 30 | 40 | |
| Butoxyethanolester (2,4-D-Ester; Weedone) | 125 | 0 | |
| (I-2, Na salt) + Butoxyethanolester (2,4-D-Ester; Weedone) | 30 + 125 | 70 | 40 |

Table B-37:

|  | Applic. rate (g ai./ha) | AVENA FATUA found | AVENA FATUA calc. |
|---|---|---|---|
| (I-2, Na salt) | 30<br>15 | 60<br>60 | |
| Butoxyethanolester (2,4-D-Ester; Weedone) | 250<br>125 | 0<br>0 | |
| (I-2, Na salt) + Butoxyethanolester (2,4-D-Ester; Weedone) | 30 + 250<br>30 + 125<br>15 + 125 | 90<br>80<br>80 | 60<br>60<br>60 |

Table B-38:

|  | Applic. rate (g ai./ha) | BROMUS SECALINUS found | BROMUS SECALINUS calc. |
|---|---|---|---|
| (I-2, Na salt) | 30<br>15 | 70<br>60 | |
| Butoxyethanolester (2,4-D-Ester; Weedone) | 125 | 0 | |
| (I-2, Na salt) + Butoxyethanolester (2,4-D-Ester; Weedone) | 30 + 125<br>15 + 125 | 95<br>80 | 70<br>60 |

Table B-39:

|  | Applic. rate (g ai./ha) | ERIOCHLOA VILLOSA found | ERIOCHLOA VILLOSA calc. |
|---|---|---|---|
| (I-2, Na salt) | 15 | 40 |  |
| Butoxyethanolester (2,4-D-Ester; Weedone) | 125 | 0 |  |
| (I-2, Na salt) + Butoxyethanolester (2,4-D-Ester; Weedone) | 15 + 125 | 60 | 40 |

Table B-40:

|  | Applic. rate (g ai./ha) | LOLIUM PERENNE found | LOLIUM PERENNE calc. |
|---|---|---|---|
| (I-2, Na salt) | 60 | 70 |  |
|  | 30 | 70 |  |
|  | 15 | 60 |  |
| Butoxyethanolester (2,4-D-Ester; Weedone) | 250 | 0 |  |
|  | 125 | 0 |  |
| (I-2, Na salt) + Butoxyethanolester (2,4-D-Ester; Weedone) | 60 + 250 | 90 | 70 |
|  | 30 + 250 | 90 | 70 |
|  | 60 + 125 | 90 | 70 |
|  | 30 + 125 | 90 | 70 |
|  | 15 + 125 | 80 | 60 |

Table B-41:

|  | Applic. rate (g ai./ha) | SETARIA VIRIDIS found | SETARIA VIRIDIS calc. |
|---|---|---|---|
| (I-2, Na salt) | 60 | 98 |  |
|  | 30 | 98 |  |
|  | 15 | 90 |  |
| Butoxyethanolester (2,4-D-Ester; Weedone) | 250 | 0 |  |
|  | 125 | 0 |  |
| (I-2, Na salt) + Butoxyethanolester (2,4-D-Ester; Weedone) | 60 + 250 | 100 | 98 |
|  | 15 + 250 | 95 | 90 |
|  | 60 + 125 | 100 | 98 |
|  | 30 + 125 | 100 | 98 |

Table B-42:

|  | Applic. rate (g ai./ha) | GALIUM APARINE found | GALIUM APARINE calc. |
|---|---|---|---|
| (I-2, Na salt) | 60 | 30 |  |
| Butoxyethanolester (2,4-D-Ester; Weedone) | 125 | 0 |  |
| (I-2, Na salt) + Butoxyethanolester (2,4-D-Ester; Weedone) | 60 + 125 | 50 | 30 |

Table B-43:

|  | Applic. rate (g ai./ha) | POLYGONUM CONVOLVULUS found | POLYGONUM CONVOLVULUS calc. |
|---|---|---|---|
| (I-2, Na salt) | 15 | 80 |  |
| Butoxyethanolester (2,4-D-Ester; Weedone) | 250 | 95 |  |
| (I-2, Na salt) + Butoxyethanolester (2,4-D-Ester; Weedone) | 15 + 250 | 100 | 99 |

Table B-44:

|  | Applic. rate (g ai./ha) | VERONICA PERSICARIA found | VERONICA PERSICARIA calc. |
|---|---|---|---|
| (I-2, Na salt) | 15 | 10 |  |
| Butoxyethanolester (2,4-D-Ester; Weedone) | 250 | 0 |  |
| (I-2, Na salt) + Butoxyethanolester (2,4-D-Ester; Weedone) | 15 + 250 | 40 | 10 |

Table B-45:

|  | Applic. rate (g ai./ha) | VIOLA ARVENSIS found | VIOLA ARVENSIS calc. |
|---|---|---|---|
| (I-2, Na salt) | 15 | 0 | |
| Butoxyethanolester (2,4-D-Ester; Weedone) | 250 | 0 | |
| (I-2, Na salt) + Butoxyethanolester (2,4-D-Ester; Weedone) | 15 + 250 | 50 | 0 |

Table B-46:

|  | Applic. rate (g ai./ha) | XANTHIUM STRUMARIUM found | XANTHIUM STRUMARIUM calc. |
|---|---|---|---|
| (I-2, Na salt) | 60<br>15 | 70<br>50 | |
| Butoxyethanolester (2,4-D-Ester; Weedone) | 250 | 95 | |
| (I-2, Na salt) + Butoxyethanolester (2,4-D-Ester; Weedone) | 60 + 250<br>15 + 250 | 100<br>100 | 98.5<br>97.5 |

Table B-47:

|  | Applic. rate (g ai./ha) | ALOPECURUS MYOSUROIDES found | ALOPECURUS MYOSUROIDES calc. |
|---|---|---|---|
| (I-2, Na salt) | 30<br>15 | 40<br>10 | |
| Bromoxynil | 125<br>60 | 0<br>0 | |
| (I-2, Na salt) + Bromoxynil | 15 + 125<br>30 + 60 | 50<br>70 | 10<br>40 |

Table B-48:

|  | Applic. rate (g ai./ha) | AVENA FATUA found | AVENA FATUA calc. |
|---|---|---|---|
| (I-2, Na salt) | 60 | 70 | |
|  | 30 | 60 | |
|  | 15 | 60 | |
| Bromoxynil | 125 | 0 | |
|  | 60 | 0 | |
| (I-2, Na salt) + Bromoxynil | 60 + 125 | 90 | 70 |
|  | 30 + 125 | 90 | 60 |
|  | 15 + 125 | 80 | 60 |
|  | 30 + 60 | 80 | 60 |
|  | 15 + 60 | 80 | 60 |

Table B-49:

|  | Applic. rate (g ai./ha) | BROMUS SECALINUS found | BROMUS SECALINUS calc. |
|---|---|---|---|
| (I-2, Na salt) | 30 | 70 | |
|  | 15 | 60 | |
| Bromoxynil | 125 | 0 | |
|  | 60 | 0 | |
| (I-2, Na salt) + Bromoxynil | 30 + 125 | 90 | 70 |
|  | 15 + 60 | 80 | 60 |

Table B-50:

|  | Applic. rate (g ai./ha) | ERIOCHLOA VILLOSA found | ERIOCHLOA VILLOSA calc. |
|---|---|---|---|
| (I-2, Na salt) | 15 | 40 | |
| Bromoxynil | 125 | 0 | |
| (I-2, Na salt) + Bromoxynil | 15 + 125 | 60 | 40 |

Table B-51:

|  | Applic. rate (g ai./ha) | LOLIUM PERENNE found | LOLIUM PERENNE calc. |
|---|---|---|---|
| (I-2, Na salt) | 60 | 70 | |
|  | 30 | 70 | |
|  | 15 | 60 | |
| Bromoxynil | 125 | 0 | |
|  | 60 | 0 | |
| (I-2, Na salt) + Bromoxynil | 60 + 125 | 90 | 70 |
|  | 30 + 125 | 90 | 70 |
|  | 60 + 60 | 90 | 70 |
|  | 15 + 60 | 80 | 60 |

Table B-52:

|  | Applic. rate (g ai./ha) | SETARIA VIRIDIS found | SETARIA VIRIDIS calc. |
|---|---|---|---|
| (I-2, Na salt) | 30 | 98 | |
|  | 15 | 90 | |
| Bromoxynil | 125 | 0 | |
|  | 60 | 0 | |
| (I-2, Na salt) + Bromoxynil | 60 + 125 | 100 | 98 |
|  | 15 + 125 | 98 | 90 |
|  | 15 + 60 | 98 | 90 |

Table B-53:

|  | Applic. rate (g ai./ha) | AMARANTHUS RETROFLEXUS found | AMARANTHUS RETROFLEXUS calc. |
|---|---|---|---|
| (I-2, Na salt) | 15 | 90 | |
| Bromoxynil | 125 | 0 | |
| (I-2, Na salt) + Bromoxynil | 15 + 125 | 100 | 90 |

Table B-54:

|  | Applic. rate (g ai./ha) | CASSIA TORA found | CASSIA TORA calc. |
|---|---|---|---|
| (I-2, Na salt) | 15 | 0 |  |
| Bromoxynil | 125 | 0 |  |
| (I-2, Na salt) + Bromoxynil | 15 + 125 | 60 | 0 |

Table B-55:

|  | Applic. rate (g ai./ha) | CHENOPODIUM ALBUM found | CHENOPODIUM ALBUM calc. |
|---|---|---|---|
| (I-2, Na salt) | 15 | 40 |  |
| Bromoxynil | 125 | 0 |  |
| (I-2, Na salt) + Bromoxynil | 15 + 125 | 98 | 40 |

Table B-56:

|  | Applic. rate (g ai./ha) | DATURA STRAMONIUM found | DATURA STRAMONIUM calc. |
|---|---|---|---|
| (I-2, Na salt) | 15 | 90 |  |
| Bromoxynil | 60 | 0 |  |
| (I-2, Na salt) + Bromoxynil | 15 + 60 | 100 | 90 |

Table B-57:

|  | Applic. rate (g ai./ha) | GALIUM APARINE found | GALIUM APARINE calc. |
|---|---|---|---|
| (I-2, Na salt) | 60 | 30 |  |
|  | 30 | 30 |  |
|  | 15 | 0 |  |
| Bromoxynil | 125 | 0 |  |
|  | 60 | 0 |  |
| (I-2, Na salt) + Bromoxynil | 60 + 125 | 50 | 30 |
|  | 30 + 125 | 50 | 30 |
|  | 15 + 125 | 50 | 0 |
|  | 60 + 60 | 50 | 30 |

Table B-58:

|  | Applic. rate (g ai./ha) | IPOMOEA HEDERACEA found | IPOMOEA HEDERACEA calc. |
|---|---|---|---|
| (I-2, Na salt) | 60 | 80 |  |
|  | 15 | 50 |  |
| Bromoxynil | 125 | 0 |  |
|  | 60 | 0 |  |
| (I-2, Na salt) + Bromoxynil | 60 + 125 | 95 | 80 |
|  | 15 + 125 | 70 | 50 |
|  | 15 + 60 | 80 | 50 |

Table B-59:

|  | Applic. rate (g ai./ha) | MATRICARIA INODORA found | MATRICARIA INODORA calc. |
|---|---|---|---|
| (I-2, Na salt) | 15 | 50 |  |
| Bromoxynil | 125 | 0 |  |
|  | 60 | 0 |  |
| (I-2, Na salt) + Bromoxynil | 15 + 125 | 98 | 50 |
|  | 15 + 60 | 70 | 50 |

Table B-60:

|  | Applic. rate (g ai./ha) | POLYGONUM CONVOLVULUS found | POLYGONUM CONVOLVULUS calc. |
|---|---|---|---|
| (I-2, Na salt) | 15 | 80 |  |
| Bromoxynil | 125<br>60 | 0<br>0 |  |
| (I-2, Na salt)<br>+<br>Bromoxynil | 15 + 125<br>15 + 60 | 100<br>98 | 80<br>80 |

Table B-61:

|  | Applic. rate (g ai./ha) | SOLANUM NIGRUM found | SOLANUM NIGRUM calc. |
|---|---|---|---|
| (I-2, Na salt) | 15 | 90 |  |
| Bromoxynil | 125<br>60 | 0<br>0 |  |
| (I-2, Na salt)<br>+<br>Bromoxynil | 15 + 125<br>15 + 60 | 100<br>98 | 90<br>90 |

Table B-62:

|  | Applic. rate (g ai./ha) | VIOLA ARVENSIS found | VIOLA ARVENSIS calc. |
|---|---|---|---|
| (I-2, Na salt) | 15 | 0 |  |
| Bromoxynil | 125 | 0 |  |
| (I-2, Na salt)<br>+<br>Bromoxynil | 15 + 125 | 80 | 0 |

Table B-63:

|  | Applic. rate (g ai./ha) | XANTHIUM STRUMARIUM found | XANTHIUM STRUMARIUM calc. |
|---|---|---|---|
| (I-2, Na salt) | 60 | 70 | |
|  | 30 | 50 | |
|  | 15 | 50 | |
| Bromoxynil | 125 | 20 | |
| (I-2, Na salt) + Bromoxynil | 60 + 125 | 100 | 76 |
|  | 30 + 125 | 98 | 60 |
|  | 15 + 125 | 90 | 60 |

Table B-64:

|  | Applic. rate (g ai./ha) | ALOPECURUS MYOSUROIDES found | ALOPECURUS MYOSUROIDES calc. |
|---|---|---|---|
| (I-2, Na salt) | 30 | 40 | |
|  | 15 | 10 | |
| Dichlorprop-P | 250 | 0 | |
|  | 125 | 0 | |
| (I-2, Na salt) + Dichlorprop-P | 30 + 250 | 80 | 40 |
|  | 30 + 125 | 60 | 40 |
|  | 15 + 125 | 60 | 10 |

Table B-65:

|  | Applic. rate (g ai./ha) | AVENA FATUA found | AVENA FATUA calc. |
|---|---|---|---|
| (I-2, Na salt) | 60 | 70 | |
|  | 30 | 60 | |
|  | 15 | 60 | |
| Dichlorprop-P | 250 | 0 | |
|  | 125 | 0 | |
| (I-2, Na salt) + Dichlorprop-P | 60 + 250 | 95 | 70 |
|  | 30 + 250 | 80 | 60 |
|  | 60 + 125 | 98 | 70 |
|  | 30 + 125 | 80 | 60 |
|  | 15 + 125 | 80 | 60 |

Table B-66:

|  | Applic. rate (g ai./ha) | BROMUS SECALINUS found | BROMUS SECALINUS calc. |
|---|---|---|---|
| (I-2, Na salt) | 15 | 60 |  |
| Dichlorprop-P | 250 | 20 |  |
| (I-2, Na salt) + Dichlorprop-P | 15 + 250 | 90 | 68 |

Table B-67:

|  | Applic. rate (g ai./ha) | ERIOCHLOA VILLOSA found | ERIOCHLOA VILLOSA calc. |
|---|---|---|---|
| (I-2, Na salt) | 15 | 40 |  |
| Dichlorprop-P | 125 | 0 |  |
| (I-2, Na salt) + Dichlorprop-P | 15 + 125 | 60 | 40 |

Table B-68:

|  | Applic. rate (g ai./ha) | LOLIUM PERENNE found | LOLIUM PERENNE calc. |
|---|---|---|---|
| (I-2, Na salt) | 60 | 70 |  |
|  | 30 | 70 |  |
|  | 15 | 60 |  |
| Dichlorprop-P | 250 | 0 |  |
|  | 125 | 0 |  |
| (I-2, Na salt) + Dichlorprop-P | 60 + 250 | 90 | 70 |
|  | 30 + 250 | 90 | 70 |
|  | 60 + 125 | 100 | 70 |
|  | 15 + 125 | 80 | 60 |

Table B-69:

|  | Applic. rate (g ai./ha) | SETARIA VIRIDIS found | SETARIA VIRIDIS calc. |
|---|---|---|---|
| (I-2, Na salt) | 60 | 98 | |
| | 30 | 98 | |
| | 15 | 90 | |
| Dichlorprop-P | 250 | 0 | |
| | 125 | 0 | |
| (I-2, Na salt) + Dichlorprop-P | 30 + 250 | 100 | 98 |
| | 15 + 250 | 98 | 90 |
| | 60 + 125 | 100 | 98 |
| | 15 + 125 | 98 | 90 |

Table B-70:

|  | Applic. rate (g ai./ha) | AMARANTHUS RETROFLEXUS found | AMARANTHUS RETROFLEXUS calc. |
|---|---|---|---|
| (I-2, Na salt) | 15 | 90 | |
| Dichlorprop-P | 250 | 30 | |
| | 125 | 0 | |
| (I-2, Na salt) + Dichlorprop-P | 15 + 250 | 98 | 93 |
| | 15 + 125 | 98 | 90 |

Table B-71:

|  | Applic. rate (g ai./ha) | SOLANUM NIGRUM found | SOLANUM NIGRUM calc. |
|---|---|---|---|
| (I-2, Na salt) | 15 | 90 | |
| Dichlorprop-P | 125 | 90 | |
| (I-2, Na salt) + Dichlorprop-P | 15 + 125 | 100 | 99 |

Table B-72:

|  | Applic. rate (g ai./ha) | VIOLA ARVENSIS found | VIOLA ARVENSIS calc. |
|---|---|---|---|
| (I-2, Na salt) | 15 | 0 |  |
| Dichlorprop-P | 250 | 20 |  |
| (I-2, Na salt) + Dichlorprop-P | 15 + 250 | 50 | 20 |

Table B-73:

|  | Applic. rate (g ai./ha) | ALOPECURUS MYOSUROIDES found | ALOPECURUS MYOSUROIDES calc. |
|---|---|---|---|
| (I-2, Na salt) | 30 | 40 |  |
|  | 15 | 10 |  |
| Tribenuron-methyl | 8 | 0 |  |
|  | 4 | 0 |  |
| (I-2, Na salt) + Tribenuron-methyl | 30 + 8 | 60 | 40 |
|  | 15 + 8 | 50 | 10 |
|  | 30 + 4 | 70 | 40 |

Table B-74:

|  | Applic. rate (g ai./ha) | AVENA FATUA found | AVENA FATUA calc. |
|---|---|---|---|
| (I-2, Na salt) | 60 | 70 |  |
| Tribenuron-methyl | 4 | 80 |  |
| (I-2, Na salt) + Tribenuron-methyl | 60 + 4 | 98 | 94 |
|  | 30 + 4 | 95 | 92 |

Table B-75:

|  | Applic. rate (g ai./ha) | BROMUS SECALINUS found | BROMUS SECALINUS calc. |
|---|---|---|---|
| (I-2, Na salt) | 60 | 90 | |
|  | 30 | 70 | |
| Tribenuron-methyl | 4 | 20 | |
| (I-2, Na salt) + Tribenuron-methyl | 60 + 4 | 98 | 92 |
|  | 30 + 4 | 95 | 76 |

Table B-76:

|  | Applic. rate (g ai./ha) | LOLIUM PERENNE found | LOLIUM PERENNE calc. |
|---|---|---|---|
| (I-2, Na salt) | 30 | 70 | |
|  | 15 | 60 | |
| Tribenuron-methyl | 8 | 30 | |
|  | 4 | 30 | |
| (I-2, Na salt) + Tribenuron-methyl | 60 + 8 | 95 | 79 |
|  | 30 + 8 | 98 | 79 |
|  | 15 + 8 | 90 | 72 |
|  | 60 + 4 | 98 | 79 |
|  | 30 + 4 | 95 | 79 |
|  | 15 + 4 | 90 | 72 |

Table B-77:

|  | Applic. rate (g ai./ha) | SETARIA VIRIDIS found | SETARIA VIRIDIS calc. |
|---|---|---|---|
| (I-2, Na salt) | 60 | 98 | |
|  | 30 | 98 | |
|  | 15 | 90 | |
| Tribenuron-methyl | 8 | 0 | |
|  | 4 | 0 | |
| (I-2, Na salt) + Tribenuron-methyl | 15 + 8 | 100 | 90 |
|  | 60 + 4 | 100 | 98 |
|  | 30 + 4 | 100 | 98 |
|  | 15 + 4 | 95 | 90 |

Table B-78:

|  | Applic. rate (g ai./ha) | ABUTILON THEOPHRASTI found | ABUTILON THEOPHRASTI calc. |
|---|---|---|---|
| (I-2, Na salt) | 15 | 10 | |
| Tribenuron-methyl | 4 | 50 | |
| (I-2, Na salt) + Tribenuron-methyl | 15 + 4 | 90 | 55 |

Table B-79:

|  | Applic. rate (g ai./ha) | AMARANTHUS RETROFLEXUS found | AMARANTHUS RETROFLEXUS calc. |
|---|---|---|---|
| (I-2, Na salt) | 15 | 90 | |
| Tribenuron-methyl | 4 | 0 | |
| (I-2, Na salt) + Tribenuron-methyl | 15 + 4 | 95 | 90 |

Table B-80:

|  | Applic. rate (g ai./ha) | CASSIA TORA found | CASSIA TORA calc. |
|---|---|---|---|
| (I-2, Na salt) | 15 | 0 | |
| Tribenuron-methyl | 4 | 0 | |
| (I-2, Na salt) + Tribenuron-methyl | 15 + 4 | 30 | 0 |

Table B-81:

|  | Applic. rate (g ai./ha) | CHENOPODIUM ALBUM found | CHENOPODIUM ALBUM calc. |
|---|---|---|---|
| (I-2, Na salt) | 15 | 40 |  |
| Tribenuron-methyl | 4 | 60 |  |
| (I-2, Na salt) + Tribenuron-methyl | 15 + 4 | 100 | 76 |

Table B-82:

|  | Applic. rate (g ai./ha) | GALIUM APARINE found | GALIUM APARINE calc. |
|---|---|---|---|
| (I-2, Na salt) | 15 | 0 |  |
| Tribenuron-methyl | 4 | 20 |  |
| (I-2, Na salt) + Tribenuron-methyl | 15 + 4 | 50 | 20 |

Table B-83:

|  | Applic. rate (g ai./ha) | MATRICARIA INODORA found | MATRICARIA INODORA calc. |
|---|---|---|---|
| (I-2, Na salt) | 15 | 50 |  |
| Tribenuron-methyl | 4 | 0 |  |
| (I-2, Na salt) + Tribenuron-methyl | 15 + 4 | 95 | 50 |

Table B-84:

|  | Applic. rate (g ai./ha) | STELLARIA MEDIA found | STELLARIA MEDIA calc. |
|---|---|---|---|
| (I-2, Na salt) | 15 | 40 |  |
| Tribenuron-methyl | 4 | 80 |  |
| (I-2, Na salt) + Tribenuron-methyl | 15 + 4 | 100 | 88 |

Table B-85:

|  | Applic. rate (g ai./ha) | VERONICA PERSICARIA found | VERONICA PERSICARIA calc. |
|---|---|---|---|
| (I-2, Na salt) | 15 | 10 |  |
| Tribenuron-methyl | 8<br>4 | 80<br>0 |  |
| (I-2, Na salt) + Tribenuron-methyl | 15 + 8<br>15 + 4 | 100<br>40 | 82<br>10 |

Table B-86:

|  | Applic. rate (g ai./ha) | VIOLA ARVENSIS found | VIOLA ARVENSIS calc. |
|---|---|---|---|
| (I-2, Na salt) | 15 | 0 |  |
| Tribenuron-methyl | 8 | 98 |  |
| (I-2, Na salt) + Tribenuron-methyl | 15 + 8 | 100 | 98 |

Table B-87:

|  | Applic. rate (g ai./ha) | XANTHIUM STRUMARIUM found | XANTHIUM STRUMARIUM calc. |
|---|---|---|---|
| (I-2, Na salt) | 30<br>15 | 50<br>50 |  |
| Tribenuron-methyl | 4 | 20 |  |
| (I-2, Na salt)<br>+<br>Tribenuron-methyl | 30 + 4<br>15 + 4 | 80<br>80 | 60<br>60 |

Table B-88:

|  | Applic. rate (g ai./ha) | BROMUS SECALINUS found | BROMUS SECALINUS calc. |
|---|---|---|---|
| (I-2, Na salt) | 60<br>15 | 90<br>70 |  |
| Imazametabenz | 125<br>60 | 0<br>0 |  |
| (I-2, Na salt)<br>+<br>Imazametabenz | 15 + 125<br>60 + 60<br>15 + 60 | 90<br>98<br>90 | 70<br>90<br>70 |

Table B-89:

|  | Applic. rate (g ai./ha) | DIGITARIA SANGUINALIS found | DIGITARIA SANGUINALIS calc. |
|---|---|---|---|
| (I-2, Na salt) | 60 | 20 |  |
| Imazametabenz | 60 | 0 |  |
| (I-2, Na salt)<br>+<br>Imazametabenz | 60 + 60 | 60 | 20 |

Table B-90:

|  | Applic. rate (g ai./ha) | ECHINOCHLOA CRUS-GALLI found | ECHINOCHLOA CRUS-GALLI calc. |
|---|---|---|---|
| (I-2, Na salt) | 60 | 90 | |
|  | 15 | 50 | |
| Imazametabenz | 125 | 0 | |
|  | 60 | 0 | |
| (I-2, Na salt) + Imazametabenz | 60 + 125 | 98 | 90 |
|  | 15 + 125 | 90 | 50 |
|  | 60 + 60 | 98 | 90 |
|  | 15 + 60 | 90 | 50 |

Table B-91:

|  | Applic. rate (g ai./ha) | LOLIUM PERENNE found | LOLIUM PERENNE calc. |
|---|---|---|---|
| (I-2, Na salt) | 60 | 90 | |
|  | 30 | 90 | |
| Imazametabenz | 125 | 0 | |
|  | 60 | 0 | |
| (I-2, Na salt) + Imazametabenz | 60 + 125 | 98 | 90 |
|  | 30 + 125 | 98 | 90 |
|  | 60 + 60 | 98 | 90 |

Table B-92:

|  | Applic. rate (g ai./ha) | AMARANTHUS RETROFLEXUS found | AMARANTHUS RETROFLEXUS calc. |
|---|---|---|---|
| (I-2, Na salt) | 60 | 90 | |
|  | 30 | 90 | |
|  | 15 | 90 | |
| Imazametabenz | 125 | 0 | |
|  | 60 | 0 | |
| (I-2, Na salt) + Imazametabenz | 60 + 125 | 98 | 90 |
|  | 30 + 125 | 95 | 90 |
|  | 60 + 60 | 100 | 90 |
|  | 30 + 60 | 98 | 90 |
|  | 15 + 60 | 98 | 90 |

Table B-93:

|  | Applic. rate (g ai./ha) | CASSIA TORA found | CASSIA TORA calc. |
|---|---|---|---|
| (I-2, Na salt) | 60 | 0 |  |
| Imazametabenz | 125 | 30 |  |
| (I-2, Na salt) + Imazametabenz | 60 + 125 | 60 | 30 |

Table B-94:

|  | Applic. rate (g ai./ha) | GALIUM APARINE found | GALIUM APARINE calc. |
|---|---|---|---|
| (I-2, Na salt) | 60 | 0 |  |
|  | 30 | 0 |  |
|  | 15 | 0 |  |
| Imazametabenz | 60 | 0 |  |
| (I-2, Na salt) + Imazametabenz | 60 + 60 | 30 | 0 |
|  | 30 + 60 | 30 | 0 |
|  | 15 + 60 | 30 | 0 |

Table B-95:

|  | Applic. rate (g ai./ha) | MATRICARIA INODORA found | MATRICARIA INODORA calc. |
|---|---|---|---|
| (I-2, Na salt) | 60 | 20 |  |
| Imazametabenz | 60 | 0 |  |
| (I-2, Na salt) + Imazametabenz | 60 + 60 | 50 | 20 |

Table B-96:

|  | Applic. rate (g ai./ha) | STELLARIA MEDIA found | STELLARIA MEDIA calc. |
|---|---|---|---|
| (I-2, Na salt) | 60 | 80 |  |
| Imazametabenz | 125 | 0 |  |
|  | 60 | 0 |  |
| (I-2, Na salt) + Imazametabenz | 60 + 125 | 100 | 80 |
|  | 60 + 60 | 100 | 80 |

Table B-97:

|  | Applic. rate (g ai./ha) | VERONICA PERSICARIA found | VERONICA PERSICARIA calc. |
|---|---|---|---|
| (I-2, Na salt) | 60 | 0 |  |
| Imazametabenz | 125 | 0 |  |
|  | 60 | 0 |  |
| (I-2, Na salt) + Imazametabenz | 60 + 125 | 30 | 0 |
|  | 60 + 60 | 30 | 0 |

Table B-98:

|  | Applic. rate (g ai./ha) | VIOLA ARVENSIS found | VIOLA ARVENSIS calc. |
|---|---|---|---|
| (I-2, Na salt) | 60 | 50 |  |
|  | 30 | 50 |  |
|  | 15 | 50 |  |
| Imazametabenz | 125 | 0 |  |
|  | 60 | 0 |  |
| (I-2, Na salt) + Imazametabenz | 60 + 125 | 98 | 50 |
|  | 30 + 60 | 70 | 50 |
|  | 15 + 60 | 70 | 50 |

Table B-99:

|  | applic. rate (g ai./ha) | AVENA FATUA found | AVENA FATUA calc. |
|---|---|---|---|
| (I-1, Na salt) | 30<br>15 | 90<br>70 |  |
| Diflufenican 40WP | 30 | 10 |  |
| (I-1, Na salt)<br>+<br>Diflufenican 40WP | 30 + 30<br>15 + 30 | 95<br>90 | 91<br>73 |

Table B-100:

|  | applic. rate (g ai./ha) | ECHINOCHLOA CRUS-GALLI found | ECHINOCHLOA CRUS-GALLI calc. |
|---|---|---|---|
| (I-1, Na salt) | 60 | 98 |  |
| Diflufenican 40WP | 30 | 50 |  |
| (I-1, Na salt)<br>+<br>Diflufenican 40WP | 60 + 30 | 100 | 99 |

Table B-101:

|  | applic. rate (g ai./ha) | ERIOCHLOA VILLOSA found | ERIOCHLOA VILLOSA calc. |
|---|---|---|---|
| (I-1, Na salt) | 30<br>15 | 98<br>60 |  |
| Diflufenican 40WP | 30 | 10 |  |
| (I-1, Na salt)<br>+<br>Diflufenican 40WP | 30 + 30<br>15 + 30 | 100<br>100 | 98,2<br>64 |

Table B-102:

|  | applic. rate (g ai./ha) | SETARIA VIRIDIS found | SETARIA VIRIDIS calc. |
|---|---|---|---|
| (I-1, Na salt) | 15 | 20 |  |
| Diflufenican 40WP | 60 | 80 |  |
| (I-1, Na salt) + Diflufenican 40WP | 15 + 60 | 95 | 84 |

Table B-103:

|  | applic. rate (g ai./ha) | ABUTILON THEOPHRASTI found | ABUTILON THEOPHRASTI calc. |
|---|---|---|---|
| (I-1, Na salt) | 15 | 0 |  |
| Diflufenican 40WP | 30 | 80 |  |
| (I-1, Na salt) + Diflufenican 40WP | 15 + 30 | 95 | 80 |

Table B-104:

|  | applic. rate (g ai./ha) | CASSIA TORA found | CASSIA TORA calc. |
|---|---|---|---|
| (I-1, Na salt) | 15 | 0 |  |
| Diflufenican 40WP | 30 | 50 |  |
| (I-1, Na salt) + Diflufenican 40WP | 15 + 30 | 100 | 50 |

Table B-105:

|  | applic. rate (g ai./ha) | DATURA STRAMONIUM found | DATURA STRAMONIUM calc. |
|---|---|---|---|
| (I-1, Na salt) | 60 | 70 | |
|  | 30 | 50 | |
|  | 15 | 10 | |
| Diflufenican 40WP | 60 | 90 | |
| (I-1, Na salt) + Diflufenican 40WP | 60 + 60 | 100 | 97 |
|  | 30 + 60 | 100 | 95 |
|  | 15 + 60 | 98 | 91 |

Table B-106:

|  | applic. rate (g ai./ha) | POLYGONUM CONVOLVULUS found | POLYGONUM CONVOLVULUS calc. |
|---|---|---|---|
| (I-1, Na salt) | 60 | 0 | |
|  | 30 | 0 | |
|  | 15 | 0 | |
| Diflufenican 40WP | 60 | 98 | |
|  | 30 | 90 | |
| (I-1, Na salt) + Diflufenican 40WP | 60 + 60 | 100 | 98 |
|  | 30 + 60 | 100 | 98 |
|  | 15 + 60 | 100 | 98 |
|  | 15 + 30 | 98 | 90 |

Table B-107:

|  | applic. rate (g ai./ha) | STELLARIA MEDIA found | STELLARIA MEDIA calc. |
|---|---|---|---|
| (I-1, Na salt) | 15 | 40 | |
| Diflufenican 40WP | 30 | 80 | |
| (I-1, Na salt) + Diflufenican 40WP | 15 + 30 | 98 | 88 |

Table B-108:

|  | applic. rate (g ai./ha) | VERONICA PERSICARIA found | VERONICA PERSICARIA calc. |
|---|---|---|---|
| (I-1, Na salt) | 30 | 0 | |
|  | 15 | 0 | |
| Diflufenican 40WP | 60 | 95 | |
|  | 30 | 95 | |
| (I-1, Na salt) + Diflufenican 40WP | 30 + 60 | 100 | 95 |
|  | 15 + 60 | 98 | 95 |
|  | 15 + 30 | 100 | 95 |

Table B-109:

|  | applic. rate (g ai./ha) | AVENA FATUA found | AVENA FATUA calc. |
|---|---|---|---|
| (I-1, Na salt) | 30 | 90 | |
|  | 15 | 70 | |
| Glyphosate | 250 | 0 | |
|  | 125 | 0 | |
| (I-1, Na salt) + Glyphosate | 30 + 250 | 98 | 90 |
|  | 15 + 125 | 95 | 70 |

Table B-110:

|  | applic. rate (g ai./ha) | BROMUS SECALINUS found | BROMUS SECALINUS calc. |
|---|---|---|---|
| (I-1, Na salt) | 30 | 95 | |
|  | 15 | 95 | |
| Glyphosate | 250 | 0 | |
|  | 125 | 0 | |
| (I-1, Na salt) + Glyphosate | 30 + 250 | 100 | 95 |
|  | 15 + 125 | 100 | 95 |

Table B-111:

|  | applic. rate (g ai./ha) | ECHINOCHLOA CRUS-GALLI found | ECHINOCHLOA CRUS-GALLI calc. |
|---|---|---|---|
| (I-1, Na salt) | 60 | 98 | |
|  | 30 | 98 | |
|  | 15 | 98 | |
| Glyphosate | 125 | 0 | |
| (I-1, Na salt) + Glyphosate | 60 + 125 | 100 | 98 |
|  | 30 + 125 | 100 | 98 |
|  | 15 + 125 | 100 | 98 |

Table B-112:

|  | applic. rate (g ai./ha) | ERIOCHLOA VILLOSA found | ERIOCHLOA VILLOSA calc. |
|---|---|---|---|
| (I-1, Na salt) | 30 | 98 | |
|  | 15 | 60 | |
| Glyphosate | 250 | 0 | |
|  | 125 | 0 | |
| (I-1, Na salt) + Glyphosate | 15 + 250 | 90 | 60 |
|  | 30 + 125 | 100 | 98 |

Table B-113:

|  | applic. rate (g ai./ha) | ABUTILON THEOPHRASTI found | ABUTILON THEOPHRASTI calc. |
|---|---|---|---|
| (I-1, Na salt) | 60 | 0 | |
| Glyphosate | 250 | 40 | |
|  | 125 | 0 | |
| (I-1, Na salt) + Glyphosate | 60 + 250 | 60 | 40 |
|  | 60 + 125 | 30 | 0 |

Table B-114:

|  | applic. rate (g ai./ha) | AMARANTHUS RETROFLEXUS found | AMARANTHUS RETROFLEXUS calc. |
|---|---|---|---|
| (I-1, Na salt) | 60 | 98 | |
|  | 30 | 98 | |
|  | 15 | 98 | |
| Glyphosate | 250 | 0 | |
|  | 125 | 0 | |
| (I-1, Na salt) + Glyphosate | 60 + 250 | 100 | 98 |
|  | 30 + 250 | 100 | 98 |
|  | 15 + 250 | 100 | 98 |
|  | 60 + 125 | 100 | 98 |
|  | 30 + 125 | 100 | 98 |
|  | 15 + 125 | 100 | 98 |

Table B-115:

|  | applic. rate (g ai./ha) | CASSIA TORA found | CASSIA TORA calc. |
|---|---|---|---|
| (I-1, Na salt) | 60 | 0 | |
| Glyphosate | 125 | 0 | |
| (I-1, Na salt) + Glyphosate | 60 + 125 | 40 | 0 |

Table B-116:

|  | applic. rate (g ai./ha) | CHENOPODIUM ALBUM found | CHENOPODIUM ALBUM calc. |
|---|---|---|---|
| (I-1, Na salt) | 60 | 90 | |
|  | 30 | 80 | |
| Glyphosate | 250 | 0 | |
| (I-1, Na salt) + Glyphosate | 60 + 250 | 95 | 90 |
|  | 30 + 250 | 100 | 80 |

Table B-117:

|  | applic. rate (g ai./ha) | DATURA STRAMONIUM found | DATURA STRAMONIUM calc. |
|---|---|---|---|
| (I-1, Na salt) | 60<br>15 | 70<br>10 |  |
| Glyphosate | 250<br>125 | 30<br>0 |  |
| (I-1, Na salt) + Glyphosate | 15 + 250<br>60 + 125 | 70<br>90 | 37<br>70 |

Table B-118:

|  | applic. rate (g ai./ha) | GALIUM APARINE found | GALIUM APARINE calc. |
|---|---|---|---|
| (I-1, Na salt) | 60 | 30 |  |
| Glyphosate | 250 | 0 |  |
| (I-1, Na salt) + Glyphosate | 60 + 250 | 60 | 30 |

Table B-119:

|  | applic. rate (g ai./ha) | IPOMOEA HEDERACEA found | IPOMOEA HEDERACEA calc. |
|---|---|---|---|
| (I-1, Na salt) | 15 | 70 |  |
| Glyphosate | 250 | 0 |  |
| (I-1, Na salt) + Glyphosate | 15 + 250 | 90 | 70 |

Table B-120:

|  | applic. rate (g ai./ha) | MATRICARIA INODORA found | MATRICARIA INODORA calc. |
|---|---|---|---|
| (I-1, Na salt) | 60 | 90 |  |
| Glyphosate | 250 | 0 |  |
| (I-1, Na salt) + Glyphosate | 60 + 250 | 95 | 90 |

Table B-121:

|  | applic. rate (g ai./ha) | POLYGONUM CONVOLVULUS found | POLYGONUM CONVOLVULUS calc. |
|---|---|---|---|
| (I-1, Na salt) | 60 | 0 |  |
| Glyphosate | 125 | 0 |  |
| (I-1, Na salt) + Glyphosate | 60 + 125 | 80 | 0 |

Table B-122:

|  | applic. rate (g ai./ha) | STELLARIA MEDIA found | STELLARIA MEDIA calc. |
|---|---|---|---|
| (I-1, Na salt) | 30 | 70 |  |
|  | 15 | 40 |  |
| Glyphosate | 250 | 0 |  |
|  | 125 | 0 |  |
| (I-1, Na salt) + Glyphosate | 30 + 250 | 95 | 70 |
|  | 15 + 250 | 80 | 40 |
|  | 30 + 125 | 90 | 70 |
|  | 15 + 125 | 95 | 40 |

Table B-123:

|  | applic. rate (g ai./ha) | VERONICA PERSICARIA found | VERONICA PERSICARIA calc. |
|---|---|---|---|
| (I-1, Na salt) | 60 | 30 | |
|  | 30 | 0 | |
|  | 15 | 0 | |
| Glyphosate | 250 | 0 | |
|  | 125 | 0 | |
| (I-1, Na salt) + Glyphosate | 60 + 250 | 100 | 30 |
|  | 30 + 250 | 70 | 0 |
|  | 15 + 250 | 60 | 0 |
|  | 60 + 125 | 60 | 30 |
|  | 30 + 125 | 30 | 0 |

Table B-124:

|  | applic. rate (g ai./ha) | VIOLA ARVENSIS found | VIOLA ARVENSIS calc. |
|---|---|---|---|
| (I-1, Na salt) | 60 | 0 | |
|  | 30 | 0 | |
|  | 15 | 0 | |
| Glyphosate | 250 | 0 | |
|  | 125 | 0 | |
| (I-1, Na salt) + Glyphosate | 60 + 250 | 70 | 0 |
|  | 30 + 250 | 30 | 0 |
|  | 15 + 250 | 20 | 0 |
|  | 60 + 125 | 60 | 0 |
|  | 30 + 125 | 50 | 0 |

Table B-125:

|  | applic. rate (g ai./ha) | AVENA FATUA found | AVENA FATUA calc. |
|---|---|---|---|
| (I-1, Na salt) | 30 | 90 | |
|  | 15 | 70 | |
| Fluthiacet-methyl (FOE 5043) | 125 | 70 | |
| (I-1, Na salt) + Fluthiacet-methyl (FOE 5043) | 30 + 125 | 100 | 97 |
|  | 15 + 125 | 100 | 91 |

Table B-126:

|  | applic. rate (g ai./ha) | AMARANTHUS RETROFLEXUS found | AMARANTHUS RETROFLEXUS calc. |
|---|---|---|---|
| (I-1, Na salt) | 60 | 98 | |
|  | 30 | 98 | |
|  | 15 | 98 | |
| Fluthiacet-methyl (FOE 5043) | 125 | 0 | |
|  | 60 | 0 | |
| (I-1, Na salt) + Fluthiacet-methyl (FOE 5043) | 60 + 125 | 100 | 98 |
|  | 30 + 125 | 100 | 98 |
|  | 60 + 60 | 100 | 98 |
|  | 30 + 60 | 100 | 98 |
|  | 15 + 60 | 100 | 98 |

Table B-127:

|  | applic. rate (g ai./ha) | POLYGONUM CONVOLVULUS found | POLYGONUM CONVOLVULUS calc. |
|---|---|---|---|
| (I-1, Na salt) | 60 | 0 | |
| Fluthiacet-methyl (FOE 5043) | 125 | 0 | |
| (I-1, Na salt) + Fluthiacet-methyl (FOE 5043) | 60 + 125 | 40 | 0 |

Table B-128:

|  | applic. rate (g ai./ha) | ALOPECURUS MYOSUROIDES found | ALOPECURUS MYOSUROIDES calc. |
|---|---|---|---|
| (I-1, Na salt) | 30 | 95 | |
| Metsulfuron-methyl | 4 | 60 | |
| (I-1, Na salt) + Metsulfuron-methyl | 30 + 4 | 100 | 98 |

Table B-129:

|  | applic. rate (g ai./ha) | AVENA FATUA found | AVENA FATUA calc. |
|---|---|---|---|
| (I-1, Na salt) | 60 | 98 |  |
| Metsulfuron-methyl | 4 | 30 |  |
| (I-1, Na salt) + Metsulfuron-methyl | 60 + 4 | 100 | 98.6 |

Table B-130:

|  | applic. rate (g ai./ha) | CYPERUS ESCULENTUS found | CYPERUS ESCULENTUS calc. |
|---|---|---|---|
| (I-1, Na salt) | 60<br>30 | 60<br>60 |  |
| Metsulfuron-methyl | 2 | 0 |  |
| (I-1, Na salt) + Metsulfuron-methyl | 60 + 2<br>30 + 2 | 80<br>80 | 60<br>60 |

Table B-131:

|  | applic. rate (g ai./ha) | DIGITARIA SANGUINALIS found | DIGITARIA SANGUINALIS calc. |
|---|---|---|---|
| (I-1, Na salt) | 60<br>30<br>15 | 0<br>0<br>0 |  |
| Metsulfuron-methyl | 4<br>2 | 20<br>10 |  |
| (I-1, Na salt) + Metsulfuron-methyl | 60 + 4<br>30 + 4<br>15 + 4<br>60 + 2 | 60<br>60<br>60<br>40 | 20<br>20<br>20<br>10 |

Table B-132:

|  | applic. rate (g ai./ha) | ECHINOCHLOA CRUS-GALLI found | ECHINOCHLOA CRUS-GALLI calc. |
|---|---|---|---|
| (I-1, Na salt) | 15 | 98 |  |
| Metsulfuron-methyl | 2 | 50 |  |
| (I-1, Na salt) + Metsulfuron-methyl | 15 + 2 | 100 | 99 |

Table B-133:

|  | applic. rate (g ai./ha) | ERIOCHLOA VILLOSA found | ERIOCHLOA VILLOSA calc. |
|---|---|---|---|
| (I-1, Na salt) | 15 | 60 |  |
| Metsulfuron-methyl | 2 | 0 |  |
| (I-1, Na salt) + Metsulfuron-methyl | 15 + 2 | 80 | 60 |

Table B-134:

|  | applic. rate (g ai./ha) | SETARIA VIRIDIS found | SETARIA VIRIDIS calc. |
|---|---|---|---|
| (I-1, Na salt) | 15 | 20 |  |
| Metsulfuron-methyl | 4<br>2 | 40<br>10 |  |
| (I-1, Na salt) + Metsulfuron-methyl | 15 + 4<br>15 + 2 | 70<br>50 | 52<br>28 |

Table B-135:

|  | applic. rate (g ai./ha) | ABUTILON THEOPHRASTI found | ABUTILON THEOPHRASTI calc. |
|---|---|---|---|
| (I-1, Na salt) | 60 | 0 | |
| | 30 | 0 | |
| | 15 | 0 | |
| Metsulfuron-methyl | 4 | 90 | |
| | 2 | 80 | |
| (I-1, Na salt) + Metsulfuron-methyl | 60 + 4 | 98 | 90 |
| | 30 + 4 | 100 | 90 |
| | 15 + 4 | 100 | 90 |
| | 15 + 2 | 98 | 80 |

Table B-136:

|  | applic. rate (g ai./ha) | POLYGONUM CONVOLVULUS found | POLYGONUM CONVOLVULUS calc. |
|---|---|---|---|
| (I-1, Na salt) | 60 | 0 | |
| | 30 | 0 | |
| | 15 | 0 | |
| Metsulfuron-methyl | 4 | 90 | |
| | 2 | 90 | |
| (I-1, Na salt) + Metsulfuron-methyl | 60 + 4 | 98 | 90 |
| | 30 + 4 | 95 | 90 |
| | 15 + 4 | 95 | 90 |
| | 60 + 2 | 100 | 90 |
| | 15 + 2 | 98 | 90 |

Table B-137:

|  | applic. rate (g ai./ha) | VIOLA ARVENSIS found | VIOLA ARVENSIS calc. |
|---|---|---|---|
| (I-1, Na salt) | 60 | 0 | |
| | 30 | 0 | |
| | 15 | 0 | |
| Metsulfuron-methyl | 4 | 98 | |
| | 2 | 90 | |
| (I-1, Na salt) + Metsulfuron-methyl | 60 + 4 | 100 | 98 |
| | 15 + 4 | 100 | 98 |
| | 60 + 2 | 100 | 90 |
| | 30 + 2 | 100 | 90 |
| | 15 + 2 | 98 | 90 |

Table B-138:

|  | applic. rate (g ai./ha) | AVENA FATUA found | AVENA FATUA calc. |
|---|---|---|---|
| (I-1, Na salt) | 60 | 70 |  |
|  | 30 | 70 |  |
| Fluroxypyr-meptyl | 30 | 0 |  |
| (I-1, Na salt) + Fluroxypyr-meptyl | 60 + 30 | 98 | 70 |
|  | 30 + 30 | 90 | 70 |

Table B-139:

|  | applic. rate (g ai./ha) | ECHINOCHLOA CRUS-GALLI found | ECHINOCHLOA CRUS-GALLI calc. |
|---|---|---|---|
| (I-1, Na salt) | 60 | 98 |  |
|  | 30 | 95 |  |
|  | 15 | 95 |  |
| Fluroxypyr-meptyl | 60 | 40 |  |
| (I-1, Na salt) + Fluroxypyr-meptyl | 60 + 60 | 100 | 98,8 |
|  | 30 + 60 | 100 | 97 |
|  | 15 + 60 | 100 | 97 |

Table B-140:

|  | applic. rate (g ai./ha) | LOLIUM PERENNE found | LOLIUM PERENNE calc. |
|---|---|---|---|
| (I-1, Na salt) | 60 | 50 |  |
|  | 30 | 40 |  |
| Fluroxypyr-meptyl | 30 | 0 |  |
| (I-1, Na salt) + Fluroxypyr-meptyl | 60 + 30 | 80 | 50 |
|  | 30 + 30 | 80 | 40 |

Table B-141:

|  | applic. rate (g ai./ha) | ABUTILON THEOPHRASTI found | ABUTILON THEOPHRASTI calc. |
|---|---|---|---|
| (I-1, Na salt) | 60 | 0 | |
|  | 30 | 0 | |
| Fluroxypyr-meptyl | 60 | 60 | |
| (I-1, Na salt) + Fluroxypyr-meptyl | 60 + 60 | 80 | 60 |
|  | 30 + 60 | 80 | 60 |

Table B-142:

|  | applic. rate (g ai./ha) | CASSIA TORA found | CASSIA TORA calc. |
|---|---|---|---|
| (I-1, Na salt) | 60 | 20 | |
| Fluroxypyr-meptyl | 30 | 0 | |
| (I-1, Na salt) + Fluroxypyr-meptyl | 60 + 30 | 70 | 20 |

Table B-143:

|  | applic. rate (g ai./ha) | POLYGONUM CONVOLVULUS found | POLYGONUM CONVOLVULUS calc. |
|---|---|---|---|
| (I-1, Na salt) | 60 | 10 | |
| Fluroxypyr-meptyl | 60 | 98 | |
| (I-1, Na salt) + Fluroxypyr-meptyl | 60 + 60 | 100 | 98,2 |

Table B-144:

|  | applic. rate (g ai./ha) | STELLARIA MEDIA found | STELLARIA MEDIA calc. |
|---|---|---|---|
| (I-1, Na salt) | 60 | 70 | |
|  | 30 | 50 | |
| Fluroxypyr-meptyl | 60 | 90 | |
|  | 30 | 90 | |
| (I-1, Na salt) + Fluroxypyr-meptyl | 60 + 60 | 100 | 97 |
|  | 30 + 60 | 100 | 95 |
|  | 60 + 30 | 100 | 97 |

Table B-145:

|  | applic. rate (g ai./ha) | ALOPECURUS MYOSUROIDES found | ALOPECURUS MYOSUROIDES calc. |
|---|---|---|---|
| (I-1, Na salt) | 60 | 90 | |
|  | 30 | 80 | |
|  | 15 | 80 | |
| Isoproturon | 250 | 90 | |
| (I-1, Na salt) + Isoproturon | 60 + 250 | 100 | 99 |
|  | 30 + 250 | 100 | 98 |
|  | 15 + 250 | 100 | 98 |

Table B-146:

|  | applic. rate (g ai./ha) | AVENA FATUA found | AVENA FATUA calc. |
|---|---|---|---|
| (I-1, Na salt) | 60 | 70 | |
|  | 30 | 70 | |
|  | 15 | 70 | |
| Isoproturon | 250 | 95 | |
| (I-1, Na salt) + Isoproturon | 60 + 250 | 100 | 98.5 |
|  | 30 + 250 | 100 | 98.5 |
|  | 15 + 250 | 100 | 98.5 |

Table B-147:

|  | applic. rate (g ai./ha) | CYPERUS ESCULENTUS found | CYPERUS ESCULENTUS calc. |
|---|---|---|---|
| (I-1, Na salt) | 60 | 70 | |
|  | 30 | 70 | |
| Isoproturon | 250 | 0 | |
| (I-1, Na salt) + Isoproturon | 60 + 250 | 90 | 70 |
|  | 30 + 250 | 90 | 70 |

Table B-148:

|  | applic. rate (g ai./ha) | DIGITARIA SANGUINALIS found | DIGITARIA SANGUINALIS calc. |
|---|---|---|---|
| (I-1, Na salt) | 60 | 20 | |
|  | 30 | 20 | |
|  | 15 | 0 | |
| Isoproturon | 500 | 70 | |
|  | 250 | 50 | |
| (I-1, Na salt) + Isoproturon | 60 + 500 | 98 | 76 |
|  | 15 + 500 | 90 | 70 |
|  | 60 + 250 | 100 | 60 |
|  | 30 + 250 | 95 | 60 |
|  | 15 + 250 | 95 | 50 |

Table B-149:

|  | applic. rate (g ai./ha) | ERIOCHLOA VILLOSA found | ERIOCHLOA VILLOSA calc. |
|---|---|---|---|
| (I-1, Na salt) | 60 | 70 | |
|  | 30 | 20 | |
|  | 15 | 20 | |
| Isoproturon | 500 | 90 | |
|  | 250 | 60 | |
| (I-1, Na salt) + Isoproturon | 60 + 500 | 100 | 97 |
|  | 30 + 500 | 100 | 92 |
|  | 15 + 500 | 100 | 92 |
|  | 60 + 250 | 100 | 88 |
|  | 30 + 250 | 100 | 68 |
|  | 15 + 250 | 100 | 68 |

Table B-150:

|  | applic. rate (g ai./ha) | LOLIUM PERENNE found | LOLIUM PERENNE calc. |
|---|---|---|---|
| (I-1, Na salt) | 60 | 50 |  |
|  | 30 | 40 |  |
|  | 15 | 20 |  |
| Isoproturon | 250 | 90 |  |
| (I-1, Na salt) + Isoproturon | 60 + 250 | 100 | 95 |
|  | 30 + 250 | 100 | 94 |
|  | 15 + 250 | 100 | 92 |

Table B-151:

|  | applic. rate (g ai./ha) | IPOMOEA HEDERACEA found | IPOMOEA HEDERACEA calc. |
|---|---|---|---|
| (I-1, Na salt) | 60 | 90 |  |
|  | 30 | 80 |  |
|  | 15 | 70 |  |
| Isoproturon | 250 | 70 |  |
| (I-1, Na salt) + Isoproturon | 60 + 250 | 100 | 97 |
|  | 30 + 250 | 100 | 94 |
|  | 15 + 250 | 100 | 91 |

Table B-152:

|  | applic. rate (g ai./ha) | POLYGONUM CONVOLVULUS found | POLYGONUM CONVOLVULUS calc. |
|---|---|---|---|
| (I-1, Na salt) | 60 | 10 |  |
|  | 30 | 0 |  |
|  | 15 | 0 |  |
| Isoproturon | 250 | 80 |  |
| (I-1, Na salt) + Isoproturon | 60 + 250 | 100 | 82 |
|  | 30 + 250 | 100 | 80 |
|  | 15 + 250 | 100 | 80 |

Table B-153:

|  | applic. rate (g ai./ha) | VIOLA ARVENSIS found | VIOLA ARVENSIS calc. |
|---|---|---|---|
| (I-1, Na salt) | 60 | 30 | |
| | 15 | 0 | |
| Isoproturon | 250 | 20 | |
| (I-1, Na salt) + Isoproturon | 60 + 250 | 90 | 44 |
| | 15 + 250 | 90 | 20 |

Table B-154:

|  | applic. rate (g ai./ha) | BROMUS SECALINUS found | BROMUS SECALINUS calc. |
|---|---|---|---|
| (I-1, Na salt) | 60 | 90 | |
| | 30 | 70 | |
| | 15 | 70 | |
| Imazamox | 15 | 30 | |
| | 8 | 0 | |
| (I-1, Na salt) + Imazamox | 60 + 15 | 100 | 93 |
| | 30 + 8 | 90 | 70 |
| | 15 + 8 | 90 | 70 |

Table B-155:

|  | applic. rate (g ai./ha) | ECHINOCHLOA CRUS-GALLI found | ECHINOCHLOA CRUS-GALLI calc. |
|---|---|---|---|
| (I-1, Na salt) | 60 | 98 | |
| | 30 | 95 | |
| | 15 | 95 | |
| Imazamox | 15 | 30 | |
| (I-1, Na salt) + Imazamox | 60 + 15 | 100 | 98.6 |
| | 30 + 15 | 100 | 96.5 |
| | 15 + 15 | 100 | 96.5 |

Table B-156:

|  | applic. rate (g ai./ha) | ABUTILON THEOPHRASTI found | ABUTILON THEOPHRASTI calc. |
|---|---|---|---|
| (I-1, Na salt) | 60 | 0 | |
|  | 30 | 0 | |
|  | 15 | 0 | |
| Imazamox | 15 | 60 | |
|  | 8 | 30 | |
| (I-1, Na salt) + Imazamox | 60 + 15 | 90 | 60 |
|  | 30 + 15 | 80 | 60 |
|  | 15 + 15 | 80 | 60 |
|  | 60 + 8 | 80 | 30 |
|  | 30 + 8 | 60 | 30 |
|  | 15 + 8 | 60 | 30 |

Table B-157:

|  | applic. rate (g ai./ha) | CASSIA TORA found | CASSIA TORA calc. |
|---|---|---|---|
| (I-1, Na salt) | 60 | 20 | |
|  | 30 | 20 | |
|  | 15 | 20 | |
| Imazamox | 15 | 0 | |
|  | 8 | 0 | |
| (I-1, Na salt) + Imazamox | 60 + 15 | 70 | 20 |
|  | 30 + 15 | 50 | 20 |
|  | 60 + 8 | 50 | 20 |
|  | 30 + 8 | 50 | 20 |
|  | 15 + 8 | 50 | 20 |

Table B-158:

|  | applic. rate (g ai./ha) | DATURA STRAMONIUM found | DATURA STRAMONIUM calc. |
|---|---|---|---|
| (I-1, Na salt) | 30 | 0 | |
|  | 15 | 0 | |
| Imazamox | 8 | 60 | |
| (I-1, Na salt) + Imazamox | 30 + 8 | 90 | 60 |
|  | 15 + 8 | 80 | 60 |

Table B-159:

|  | applic. rate (g ai./ha) | GALIUM APARINE found | GALIUM APARINE calc. |
|---|---|---|---|
| (I-1, Na salt) | 60 | 40 | |
|  | 15 | 30 | |
| Imazamox | 8 | 0 | |
| (I-1, Na salt) + Imazamox | 60 + 8 | 70 | 40 |
|  | 15 + 8 | 50 | 30 |

Table B-160:

|  | applic. rate (g ai./ha) | MATRICARIA INODORA found | MATRICARIA INODORA calc. |
|---|---|---|---|
| (I-1, Na salt) | 15 | 40 | |
| Imazamox | 15 | 0 | |
|  | 8 | 0 | |
| (I-1, Na salt) + Imazamox | 15 + 15 | 60 | 40 |
|  | 15 + 8 | 60 | 40 |

Table B-161:

|  | applic. rate (g ai./ha) | POLYGONUM CONVOLVULUS found | POLYGONUM CONVOLVULUS calc. |
|---|---|---|---|
| (I-1, Na salt) | 60 | 10 | |
|  | 30 | 0 | |
|  | 15 | 0 | |
| Imazamox | 15 | 60 | |
|  | 8 | 20 | |
| (I-1, Na salt) + Imazamox | 30 + 15 | 70 | 60 |
|  | 15 + 15 | 70 | 60 |
|  | 60 + 8 | 70 | 28 |
|  | 30 + 8 | 60 | 20 |
|  | 15 + 8 | 60 | 20 |

Table B-162:

|  | applic. rate (g ai./ha) | STELLARIA MEDIA found | STELLARIA MEDIA calc. |
|---|---|---|---|
| (I-1, Na salt) | 60 | 70 | |
|  | 30 | 50 | |
|  | 15 | 30 | |
| Imazamox | 15 | 80 | |
|  | 8 | 10 | |
| (I-1, Na salt) + Imazamox | 60 + 15 | 98 | 94 |
|  | 30 + 15 | 98 | 90 |
|  | 30 + 8 | 80 | 55 |
|  | 15 + 8 | 70 | 37 |

Table B-163:

|  | applic. rate (g ai./ha) | CYPERUS ESCULENTUS found | CYPERUS ESCULENTUS calc. |
|---|---|---|---|
| (I-2, Na salt) | 60 | 0 | |
| Diclofop-methyl | 125 | 0 | |
| MKH6562 + Diclofop-methyl | 60 + 125 | 30 | 0 |

Table B-164:

|  | applic. rate (g ai./ha) | ABUTILON THEOPHRASTI found | ABUTILON THEOPHRASTI calc. |
|---|---|---|---|
| (I-2, Na salt) | 60 | 50 | |
| Diclofop-methyl | 250 | 0 | |
| MKH6562 + Diclofop-methyl | 60 + 250 | 80 | 50 |

Table B-165:

|  | applic. rate (g ai./ha) | AMARANTHUS RETROFLEXUS found | AMARANTHUS RETROFLEXUS calc. |
|---|---|---|---|
| (I-2, Na salt) | 15 | 95 |  |
| Diclofop-methyl | 250<br>125 | 0<br>0 |  |
| MKH6562 + Diclofop-methyl | 15 + 250<br>15 + 125 | 100<br>100 | 95<br>95 |

Table B-166:

|  | applic. rate (g ai./ha) | GALIUM APARINE found | GALIUM APARINE calc. |
|---|---|---|---|
| (I-2, Na salt) | 60<br>30<br>15 | 20<br>20<br>0 |  |
| Diclofop-methyl | 250<br>125 | 0<br>0 |  |
| MKH6562 + Diclofop-methyl | 60 + 250<br>30 + 250<br>15 + 250<br>60 + 125<br>30 + 125<br>15 + 125 | 70<br>50<br>40<br>50<br>50<br>40 | 20<br>20<br>0<br>20<br>20<br>0 |

Table B-167:

|  | applic. rate (g ai./ha) | IPOMOEA HEDERACEA found | IPOMOEA HEDERACEA calc. |
|---|---|---|---|
| (I-2, Na salt) | 60 | 80 |  |
| Diclofop-methyl | 250 | 20 |  |
| MKH6562 + Diclofop-methyl | 60 + 250 | 95 | 84 |

Table B-168:

|  | applic. rate (g ai./ha) | SOLANUM NIGRUM found | SOLANUM NIGRUM calc. |
|---|---|---|---|
| (I-2, Na salt) | 30 | 95 | |
| | 15 | 95 | |
| Diclofop-methyl | 250 | 0 | |
| | 125 | 0 | |
| MKH6562 + Diclofop-methyl | 30 + 250 | 100 | 95 |
| | 15 + 250 | 100 | 95 |
| | 30 + 125 | 100 | 95 |
| | 15 + 125 | 100 | 95 |

Table B-169:

|  | applic. rate (g ai./ha) | VIOLA ARVENSIS found | VIOLA ARVENSIS calc. |
|---|---|---|---|
| (I-2, Na salt) | 30 | 60 | |
| | 15 | 20 | |
| Diclofop-methyl | 250 | 0 | |
| | 125 | 0 | |
| MKH6562 + Diclofop-methyl | 30 + 250 | 80 | 60 |
| | 15 + 250 | 80 | 20 |
| | 15 + 125 | 70 | 20 |

Table B-170:

|  | applic. rate (g ai./ha) | XANTHIUM STRUMARIUM found | XANTHIUM STRUMARIUM calc. |
|---|---|---|---|
| (I-2, Na salt) | 15 | 30 | |
| Diclofop-methyl | 250 | 0 | |
| | 125 | 0 | |
| MKH6562 + Diclofop-methyl | 15 + 250 | 50 | 30 |
| | 15 + 125 | 50 | 30 |

Table B-171:

|  | applic. rate (g ai./ha) | BROMUS SECALINUS found | BROMUS SECALINUS calc. |
|---|---|---|---|
| (I-2, Na salt) | 60<br>15 | 70<br>60 |  |
| Fluroxypyr-meptyl | 60 | 0 |  |
| MKH6562 + Fluroxypyr-meptyl | 60 + 60<br>15 + 60 | 90<br>80 | 70<br>60 |

Table B-172:

|  | applic. rate (g ai./ha) | LOLIUM PERENNE found | LOLIUM PERENNE calc. |
|---|---|---|---|
| (I-2, Na salt) | 60 | 80 |  |
| Fluroxypyr-meptyl | 60 | 0 |  |
| MKH6562 + Fluroxypyr-meptyl | 60 + 60 | 95 | 80 |

Table B-173:

|  | applic. rate (g ai./ha) | SETARIA VIRIDIS found | SETARIA VIRIDIS calc. |
|---|---|---|---|
| (I-2, Na salt) | 15 | 90 |  |
| Fluroxypyr-meptyl | 30 | 30 |  |
| MKH6562 + Fluroxypyr-meptyl | 15 + 30 | 95 | 93 |

Table B-174:

|  | applic. rate (g ai./ha) | ABUTILON THEOPHRASTI found | ABUTILON THEOPHRASTI calc. |
|---|---|---|---|
| (I-2, Na salt) | 15 | 0 |  |
| Fluroxypyr-meptyl | 30 | 0 |  |
| MKH6562 + Fluroxypyr-meptyl | 15 + 30 | 40 | 0 |

Table B-175:

|  | applic. rate (g ai./ha) | AMARANTHUS RETROFLEXUS found | AMARANTHUS RETROFLEXUS calc. |
|---|---|---|---|
| (I-2, Na salt) | 15 | 95 |  |
| Fluroxypyr-meptyl | 60<br>30 | 30<br>30 |  |
| MKH6562 + Fluroxypyr-meptyl | 15 + 60<br>15 + 30 | 100<br>100 | 96.5<br>96.5 |

Table B-176:

|  | applic. rate (g ai./ha) | CASSIA TORA found | CASSIA TORA calc. |
|---|---|---|---|
| (I-2, Na salt) | 60 | 20 |  |
| Fluroxypyr-meptyl | 30 | 0 |  |
| MKH6562 + Fluroxypyr-meptyl | 60 + 30 | 50 | 20 |

Table B-177:

|  | applic. rate (g ai./ha) | BROMUS SECALINUS found | BROMUS SECALINUS calc. |
|---|---|---|---|
| (I-2, Na salt) | 60 | 80 | |
| | 30 | 70 | |
| | 15 | 70 | |
| Carfentrazone-ethyl | 8 | 0 | |
| | 4 | 0 | |
| (I-2, Na salt) + Carfentrazone-ethyl | 60 + 8 | 98 | 80 |
| | 30 + 8 | 98 | 70 |
| | 15 + 8 | 98 | 70 |
| | 60 + 4 | 98 | 80 |
| | 30 + 4 | 98 | 70 |
| | 15 + 4 | 90 | 70 |

Table B-178:

|  | applic. rate (g ai./ha) | ECHINOCHLOA CRUS-GALLI found | ECHINOCHLOA CRUS-GALLI calc. |
|---|---|---|---|
| (I-2, Na salt) | 60 | 70 | |
| | 30 | 50 | |
| Carfentrazone-ethyl | 8 | 70 | |
| | 4 | 40 | |
| (I-2, Na salt) + Carfentrazone-ethyl | 60 + 8 | 98 | 91 |
| | 60 + 4 | 98 | 82 |
| | 30 + 4 | 90 | 70 |

Table B-179:

|  | applic. rate (g ai./ha) | LOLIUM PERENNE found | LOLIUM PERENNE calc. |
|---|---|---|---|
| (I-2, Na salt) | 60 | 90 | |
| Carfentrazone-ethyl | 8 | 0 | |
| | 4 | 0 | |
| (I-2, Na salt) + Carfentrazone-ethyl | 60 + 8 | 98 | 90 |
| | 60 + 4 | 98 | 90 |

Table B-180:

|  | applic. rate (g ai./ha) | MATRICARIA INODORA found | MATRICARIA INODORA calc. |
|---|---|---|---|
| (I-2, Na salt) | 60 | 70 | |
|  | 15 | 0 | |
| Carfentrazone-ethyl | 8 | 0 | |
|  | 4 | 0 | |
| (I-2, Na salt) + Carfentrazone-ethyl | 60 + 8 | 100 | 70 |
|  | 15 + 4 | 30 | 0 |

Table B-181:

|  | applic. rate (g ai./ha) | POLYGONUM CONVOLVULUS found | POLYGONUM CONVOLVULUS calc. |
|---|---|---|---|
| (I-2, Na salt) | 60 | 70 | |
|  | 30 | 70 | |
| Carfentrazone-ethyl | 4 | 90 | |
| (I-2, Na salt) + Carfentrazone-ethyl | 60 + 4 | 100 | 97 |
|  | 30 + 4 | 100 | 97 |

Table B-182:

|  | applic. rate (g ai./ha) | STELLARIA MEDIA found | STELLARIA MEDIA calc. |
|---|---|---|---|
| (I-2, Na salt) | 30 | 60 | |
|  | 15 | 0 | |
| Carfentrazone-ethyl | 8 | 30 | |
|  | 4 | 0 | |
| (I-2, Na salt) + Carfentrazone-ethyl | 15 + 8 | 80 | 30 |
|  | 30 + 4 | 80 | 60 |

Table B-183:

|  | applic. rate (g ai./ha) | VERONICA PERSICARIA found | VERONICA PERSICARIA calc. |
|---|---|---|---|
| (I-2, Na salt) | 30 | 10 |  |
| Carfentrazone-ethyl | 8 | 95 |  |
| (I-2, Na salt) + Carfentrazone-ethyl | 30 + 8 | 98 | 95.5 |

Table B-184:

|  | applic. rate (g ai./ha) | VIOLA ARVENSIS found | VIOLA ARVENSIS calc. |
|---|---|---|---|
| (I-2, Na salt) | 60 | 70 |  |
| Carfentrazone-ethyl | 4 | 70 |  |
| (I-2, Na salt) + Carfentrazone-ethyl | 60 + 4 | 98 | 91 |

Table B-185:

|  | applic. rate (g ai./ha) | XANTHIUM STRUMARIUM found | XANTHIUM STRUMARIUM calc. |
|---|---|---|---|
| (I-2, Na salt) | 30 | 50 |  |
|  | 15 | 40 |  |
| Carfentrazone-ethyl | 8 | 98 |  |
|  | 4 | 98 |  |
| (I-2, Na salt) + Carfentrazone-ethyl | 30 + 8 | 100 | 99 |
|  | 15 + 8 | 100 | 98.8 |
|  | 30 + 4 | 100 | 99 |
|  | 15 + 4 | 100 | 98.8 |

Table B-186:

|  | applic. rate (g ai./ha) | BROMUS SECALINUS found | BROMUS SECALINUS calc. |
|---|---|---|---|
| (I-2, Na salt) | 60 | 80 | |
| | 30 | 70 | |
| | 15 | 70 | |
| Clodinafop-propargyl (80g/l) + Cloquintocet-mexyl (20g/l) | 30 | 0 | |
| | 15 | 0 | |
| (I-2, Na salt) + Clodinafop-propargyl (80g/l) + Cloquintocet-mexyl (20g/l) | 60 + 30 | 98 | 80 |
| | 60 + 15 | 98 | 80 |
| | 30 + 15 | 90 | 70 |
| | 15 + 15 | 90 | 70 |

Table B-187:

|  | applic. rate (g ai./ha) | ABUTILON THEOPHRASTI found | ABUTILON THEOPHRASTI calc. |
|---|---|---|---|
| (I-2, Na salt) | 60 | 0 | |
| Clodinafop-propargyl (80g/l) + Cloquintocet-mexyl (20g/l) | 30 | 0 | |
| (I-2, Na salt) + Clodinafop-propargyl (80g/l) + Cloquintocet-mexyl (20g/l) | 60 + 30 | 40 | 0 |

Table B-188:

|  | applic. rate (g ai./ha) | AMARANTHUS RETROFLEXUS found | AMARANTHUS RETROFLEXUS calc. |
|---|---|---|---|
| (I-2, Na salt) | 30 | 90 | |
| | 15 | 90 | |
| Clodinafop-propargyl (80g/l) + Cloquintocet-mexyl (20g/l) | 30 | 0 | |
| | 15 | 0 | |
| (I-2, Na salt) + Clodinafop-propargyl (80g/l) + Cloquintocet-mexyl (20g/l) | 30 + 30 | 100 | 90 |
| | 15 + 30 | 100 | 90 |
| | 30 + 15 | 100 | 90 |
| | 15 + 15 | 100 | 90 |

Table B-189:

|  | applic. rate (g ai./ha) | CHENOPODIUM ALBUM found | CHENOPODIUM ALBUM calc. |
|---|---|---|---|
| (I-2, Na salt) | 30 | 50 | |
|  | 15 | 50 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 30 + 30 | 70 | 50 |
|  | 30 + 15 | 80 | 50 |
|  | 15 + 15 | 70 | 50 |

Table B-190:

|  | applic. rate (g ai./ha) | GALIUM APARINE found | GALIUM APARINE calc. |
|---|---|---|---|
| (I-2, Na salt) | 60 | 0 | |
|  | 30 | 0 | |
|  | 15 | 0 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 60 + 30 | 40 | 0 |
|  | 30 + 30 | 40 | 0 |
|  | 15 + 30 | 40 | 0 |
|  | 60 + 15 | 50 | 0 |
|  | 30 + 15 | 40 | 0 |
|  | 15 + 15 | 40 | 0 |

Table B-191:

|  | applic. rate (g ai./ha) | MATRICARIA INODORA found | MATRICARIA INODORA calc. |
|---|---|---|---|
| (I-2, Na salt) | 15 | 0 | |
| Clodinafop-propargyl (80g/l) + Cloquintocet-mexyl (20g/l) | 15 | 0 | |
| (I-2, Na salt) + Clodinafop-propargyl (80g/l) + Cloquintocet-mexyl (20g/l) | 15 + 15 | 30 | 0 |

Table B-192:

|  | applic. rate (g ai./ha) | POLYGONUM CONVOLVULUS found | POLYGONUM CONVOLVULUS calc. |
|---|---|---|---|
| (I-2, Na salt) | 60 | 70 | |
|  | 30 | 70 | |
|  | 15 | 60 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 60 + 30 | 95 | 70 |
|  | 30 + 30 | 90 | 70 |
|  | 15 + 30 | 90 | 60 |
|  | 60 + 15 | 90 | 70 |
|  | 30 + 15 | 90 | 70 |
|  | 15 + 15 | 80 | 60 |

Table B-193:

|  | applic. rate (g ai./ha) | VIOLA ARVENSIS found | VIOLA ARVENSIS calc. |
|---|---|---|---|
| (I-2, Na salt) | 60 | 70 | |
|  | 30 | 70 | |
|  | 15 | 60 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 60 + 30 | 90 | 70 |
|  | 30 + 30 | 90 | 70 |
|  | 60 + 15 | 90 | 70 |
|  | 30 + 15 | 90 | 70 |
|  | 15 + 15 | 80 | 60 |

Table B-194:

|  | applic. rate (g ai./ha) | BROMUS SECALINUS found | BROMUS SECALINUS calc. |
|---|---|---|---|
| (I-2, Na salt) | 60 | 80 |  |
|  | 30 | 70 |  |
|  | 15 | 70 |  |
| Carfentrazone-ethyl | 8 | 0 |  |
|  | 4 | 0 |  |
| (I-2, Na salt) + Carfentrazone-ethyl | 60 + 8 | 98 | 80 |
|  | 30 + 8 | 98 | 70 |
|  | 15 + 8 | 98 | 70 |
|  | 60 + 4 | 98 | 80 |
|  | 30 + 4 | 98 | 70 |
|  | 15 + 4 | 90 | 70 |

Table B-195:

|  | applic. rate (g ai./ha) | ECHINOCHLOA CRUS-GALLI found | ECHINOCHLOA CRUS-GALLI calc. |
|---|---|---|---|
| (I-2, Na salt) | 60 | 70 |  |
|  | 30 | 50 |  |
| Carfentrazone-ethyl | 8 | 70 |  |
|  | 4 | 40 |  |
| (I-2, Na salt) + Carfentrazone-ethyl | 60 + 8 | 98 | 91 |
|  | 60 + 4 | 98 | 82 |
|  | 30 + 4 | 90 | 70 |

Table B-196:

|  | applic. rate (g ai./ha) | LOLIUM PERENNE found | LOLIUM PERENNE calc. |
|---|---|---|---|
| (I-2, Na salt) | 60 | 90 |  |
| Carfentrazone-ethyl | 8 | 0 |  |
|  | 4 | 0 |  |
| (I-2, Na salt) + Carfentrazone-ethyl | 60 + 8 | 98 | 90 |
|  | 60 + 4 | 98 | 90 |

Table B-197:

|  | applic. rate (g ai./ha) | VERONICA PERSICARIA found | VERONICA PERSICARIA calc. |
|---|---|---|---|
| (I-2, Na salt) | 30 | 10 |  |
| Carfentrazone-ethyl | 8 | 95 |  |
| (I-2, Na salt) + Carfentrazone-ethyl | 30 + 8 | 98 | 95.5 |

Table B-198:

|  | applic. rate (g ai./ha) | VIOLA ARVENSIS found | VIOLA ARVENSIS calc. |
|---|---|---|---|
| (I-2, Na salt) | 60 | 70 |  |
| Carfentrazone-ethyl | 4 | 70 |  |
| (I-2, Na salt) + Carfentrazone-ethyl | 60 + 4 | 98 | 91 |

Table B-199:

|  | applic. rate (g ai./ha) | XANTHIUM STRUMARIUM found | XANTHIUM STRUMARIUM calc. |
|---|---|---|---|
| (I-2, Na salt) | 30 | 50 |  |
|  | 15 | 40 |  |
| Carfentrazone-ethyl | 8 | 98 |  |
|  | 4 | 98 |  |
| (I-2, Na salt) + Carfentrazone-ethyl | 30 + 8 | 100 | 99 |
|  | 15 + 8 | 100 | 98.8 |
|  | 30 + 4 | 100 | 99 |
|  | 15 + 4 | 100 | 98.8 |

Table B-200:

|  | applic. rate (g ai./ha) | VERONICA PERSICARIA found | VERONICA PERSICARIA calc. |
|---|---|---|---|
| (I-2, Na salt) | 30 | 10 |  |
| Carfentrazone-ethyl | 8 | 95 |  |
| (I-2, Na salt) + Carfentrazone-ethyl | 30 + 8 | 98 | 95.5 |

Table B-201:

|  | applic. rate (g ai./ha) | VIOLA ARVENSIS found | VIOLA ARVENSIS calc. |
|---|---|---|---|
| (I-2, Na salt) | 60 | 70 |  |
| Carfentrazone-ethyl | 4 | 70 |  |
| (I-2, Na salt) + Carfentrazone-ethyl | 60 + 4 | 98 | 91 |

Table B-202:

|  | applic. rate (g ai./ha) | XANTHIUM STRUMARIUM found | XANTHIUM STRUMARIUM calc. |
|---|---|---|---|
| (I-2, Na salt) | 30 | 50 |  |
|  | 15 | 40 |  |
| Carfentrazone-ethyl | 8 | 98 |  |
|  | 4 | 98 |  |
| (I-2, Na salt) + Carfentrazone-ethyl | 30 + 8 | 100 | 99 |
|  | 15 + 8 | 100 | 98.8 |
|  | 30 + 4 | 100 | 99 |
|  | 15 + 4 | 100 | 98.8 |

Table B-203:

|  | applic. rate (g ai./ha) | BROMUS SECALINUS found | BROMUS SECALINUS calc. |
|---|---|---|---|
| (I-2, Na salt) | 60 | 80 |  |
|  | 30 | 70 |  |
|  | 15 | 70 |  |
| Clodinafop-propargyl (80g/l) + Cloquintocet-mexyl (20g/l) | 30 | 0 |  |
|  | 15 | 0 |  |
| (I-2, Na salt) + Clodinafop-propargyl (80g/l) + Cloquintocet-mexyl (20g/l) | 60 + 30 | 98 | 80 |
|  | 60 + 15 | 98 | 80 |
|  | 30 + 15 | 90 | 70 |
|  | 15 + 15 | 90 | 70 |

Table B-204:

|  | applic. rate (g ai./ha) | ABUTILON THEOPHRASTI found | ABUTILON THEOPHRASTI calc. |
|---|---|---|---|
| (I-2, Na salt) | 60 | 0 |  |
| Clodinafop-propargyl (80g/l) + Cloquintocet-mexyl (20g/l) | 30 | 0 |  |
| (I-2, Na salt) + Clodinafop-propargyl (80g/l) + Cloquintocet-mexyl (20g/l) | 60 + 30 | 40 | 0 |

Table B-205:

|  | applic. rate (g ai./ha) | AMARANTHUS RETROFLEXUS found | AMARANTHUS RETROFLEXUS calc. |
|---|---|---|---|
| (I-2, Na salt) | 30 | 90 |  |
|  | 15 | 90 |  |
| Clodinafop-propargyl (80g/l) + Cloquintocet-mexyl (20g/l) | 30 | 0 |  |
|  | 15 | 0 |  |
| (I-2, Na salt) + Clodinafop-propargyl (80g/l) + Cloquintocet-mexyl (20g/l) | 30 + 30 | 100 | 90 |
|  | 15 + 30 | 100 | 90 |
|  | 30 + 15 | 100 | 90 |
|  | 15 + 15 | 100 | 90 |

Table B-206:

|  | applic. rate (g ai./ha) | CHENOPODIUM ALBUM found | CHENOPODIUM ALBUM calc. |
|---|---|---|---|
| (I-2, Na salt) | 30 | 50 | |
|  | 15 | 50 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 30 + 30 | 70 | 50 |
|  | 30 + 15 | 80 | 50 |
|  | 15 + 15 | 70 | 50 |

Table B-207:

|  | applic. rate (g ai./ha) | GALIUM APARINE found | GALIUM APARINE calc. |
|---|---|---|---|
| (I-2, Na salt) | 60 | 0 | |
|  | 30 | 0 | |
|  | 15 | 0 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 60 + 30 | 40 | 0 |
|  | 30 + 30 | 40 | 0 |
|  | 15 + 30 | 40 | 0 |
|  | 60 + 15 | 50 | 0 |
|  | 30 + 15 | 40 | 0 |
|  | 15 + 15 | 40 | 0 |

Table B-208:

|  | applic. rate (g ai./ha) | MATRICARIA INODORA found | MATRICARIA INODORA calc. |
|---|---|---|---|
| (I-2, Na salt) | 15 | 0 | |
| Clodinafop-propargyl (80g/l) + Cloquintocet-mexyl (20g/l) | 15 | 0 | |
| (I-2, Na salt) + Clodinafop-propargyl (80g/l) + Cloquintocet-mexyl (20g/l) | 15 + 15 | 30 | 0 |

Table B-209:

|  | applic. rate (g ai./ha) | POLYGONUM CONVOLVULUS found | POLYGONUM CONVOLVULUS calc. |
|---|---|---|---|
| (I-2, Na salt) | 60 | 70 | |
|  | 30 | 70 | |
|  | 15 | 60 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 60 + 30 | 95 | 70 |
|  | 30 + 30 | 90 | 70 |
|  | 15 + 30 | 90 | 60 |
|  | 60 + 15 | 90 | 70 |
|  | 30 + 15 | 90 | 70 |
|  | 15 + 15 | 80 | 60 |

Table B-210:

|  | applic. rate (g ai./ha) | VIOLA ARVENSIS found | VIOLA ARVENSIS calc. |
|---|---|---|---|
| (I-2, Na salt) | 60 | 70 | |
|  | 30 | 70 | |
|  | 15 | 60 | |
| Clodinafop-propargyl (80g/l) + Cloquintocet-mexyl (20g/l) | 30 | 0 | |
|  | 15 | 0 | |
| (I-2, Na salt) + Clodinafop-propargyl (80g/l) + Cloquintocet-mexyl (20g/l) | 60 + 30 | 90 | 70 |
|  | 30 + 30 | 90 | 70 |
|  | 60 + 15 | 90 | 70 |
|  | 30 + 15 | 90 | 70 |
|  | 15 + 15 | 80 | 60 |

Table B-211:

|  | applic. rate (g ai./ha) | ALOPECURUS MYOSUROIDES found | ALOPECURUS MYOSUROIDES calc. |
|---|---|---|---|
| (I-2, Na salt) | 60 | 90 | |
|  | 30 | 90 | |
| Imazamox | 15 | 0 | |
| (I-2, Na salt) + Imazamox | 60 + 15 | 100 | 90 |
|  | 30 + 15 | 98 | 90 |

Table B-212:

|  | applic. rate (g ai./ha) | BROMUS SECALINUS found | BROMUS SECALINUS calc. |
|---|---|---|---|
| (I-2, Na salt) | 60 | 70 |  |
|  | 30 | 60 |  |
|  | 15 | 60 |  |
| Imazamox | 15 | 0 |  |
|  | 8 | 0 |  |
| (I-2, Na salt) + Imazamox | 60 + 15 | 98 | 70 |
|  | 30 + 15 | 90 | 60 |
|  | 15 + 15 | 80 | 60 |
|  | 30 + 8 | 80 | 60 |

Table B-213:

|  | applic. rate (g ai./ha) | ERIOCHLOA VILLOSA found | ERIOCHLOA VILLOSA calc. |
|---|---|---|---|
| (I-2, Na salt) | 60 | 90 |  |
|  | 30 | 90 |  |
|  | 15 | 90 |  |
| Imazamox | 15 | 70 |  |
|  | 8 | 0 |  |
| (I-2, Na salt) + Imazamox | 60 + 15 | 100 | 97 |
|  | 30 + 15 | 100 | 97 |
|  | 15 + 15 | 100 | 97 |
|  | 60 + 8 | 98 | 90 |
|  | 30 + 8 | 98 | 90 |
|  | 15 + 8 | 98 | 90 |

Table B-214:

|  | applic. rate (g ai./ha) | ABUTILON THEOPHRASTI found | ABUTILON THEOPHRASTI calc. |
|---|---|---|---|
| (I-2, Na salt) | 60 | 0 | |
|  | 30 | 0 | |
|  | 15 | 0 | |
| Imazamox | 15 | 40 | |
| (I-2, Na salt) + Imazamox | 60 + 15 | 60 | 40 |
|  | 30 + 15 | 60 | 40 |
|  | 15 + 15 | 60 | 40 |

Table B-215:

|  | applic. rate (g ai./ha) | AMARANTHUS RETROFLEXUS found | AMARANTHUS RETROFLEXUS calc. |
|---|---|---|---|
| (I-2, Na salt) | 15 | 95 | |
| Imazamox | 8 | 70 | |
| (I-2, Na salt) + Imazamox | 15 + 8 | 100 | 98.5 |

Table B-216:

|  | applic. rate (g ai./ha) | STELLARIA MEDIA found | STELLARIA MEDIA calc. |
|---|---|---|---|
| (I-2, Na salt) | 60 | 98 | |
|  | 30 | 50 | |
|  | 15 | 50 | |
| Imazamox | 15 | 98 | |
|  | 8 | 0 | |
| (I-2, Na salt) + Imazamox | 30 + 15 | 100 | 99 |
|  | 15 + 15 | 100 | 99 |
|  | 60 + 8 | 100 | 98 |
|  | 30 + 8 | 100 | 50 |
|  | 15 + 8 | 100 | 50 |

Table B-217:

|  | applic. rate (g ai./ha) | XANTHIUM STRUMARIUM found | XANTHIUM STRUMARIUM calc. |
|---|---|---|---|
| (I-2, Na salt) | 60 | 90 | |
| Imazamox | 8 | 70 | |
| (I-2, Na salt) + Imazamox | 60 + 8 | 100 | 97 |

Table B-218:

|  | applic. rate (g ai./ha) | BROMUS SECALINUS found | BROMUS SECALINUS calc. |
|---|---|---|---|
| (I-2, Na salt) | 30 | 60 | |
|  | 15 | 60 | |
| Glyphosate | 250 | 0 | |
|  | 125 | 0 | |
| (I-2, Na salt) + Glyphosate | 30 + 250 | 80 | 60 |
|  | 15 + 250 | 80 | 60 |
|  | 30 + 125 | 80 | 60 |

Table B-219:

|  | applic. rate (g ai./ha) | ERIOCHLOA VILLOSA found | ERIOCHLOA VILLOSA calc. |
|---|---|---|---|
| (I-2, Na salt) | 60 | 90 | |
| Glyphosate | 250 | 60 | |
|  | 125 | 60 | |
| (I-2, Na salt) + Glyphosate | 60 + 250 | 98 | 96 |
|  | 60 + 125 | 98 | 96 |

Table B-220:

|  | applic. rate (g ai./ha) | SETARIA VIRIDIS found | SETARIA VIRIDIS calc. |
|---|---|---|---|
| (I-2, Na salt) | 30 | 90 |  |
| Glyphosate | 250 | 70 |  |
|  | 125 | 60 |  |
| (I-2, Na salt) + Glyphosate | 30 + 250 | 100 | 97 |
|  | 30 + 125 | 98 | 96 |

Table B-221:

|  | applic. rate (g ai./ha) | ABUTILON THEOPHRASTI found | ABUTILON THEOPHRASTI calc. |
|---|---|---|---|
| (I-2, Na salt) | 60 | 0 |  |
|  | 30 | 0 |  |
|  | 15 | 0 |  |
| Glyphosate | 250 | 0 |  |
| (I-2, Na salt) + Glyphosate | 60 + 250 | 30 | 0 |
|  | 30 + 250 | 30 | 0 |
|  | 15 + 250 | 30 | 0 |

Table B-222:

|  | applic. rate (g ai./ha) | AMARANTHUS RETROFLEXUS found | AMARANTHUS RETROFLEXUS calc. |
|---|---|---|---|
| (I-2, Na salt) | 60 | 98 |  |
|  | 30 | 98 |  |
|  | 15 | 95 |  |
| Glyphosate | 250 | 0 |  |
| (I-2, Na salt) + Glyphosate | 60 + 250 | 100 | 98 |
|  | 30 + 250 | 100 | 98 |
|  | 15 + 250 | 98 | 95 |

Table B-223:

|  | applic. rate (g ai./ha) | IPOMOEA HEDERACEA found | IPOMOEA HEDERACEA calc. |
|---|---|---|---|
| (I-2, Na salt) | 60 | 70 | |
|  | 30 | 70 | |
|  | 15 | 70 | |
| Glyphosate | 250 | 0 | |
|  | 125 | 0 | |
| (I-2, Na salt) + Glyphosate | 60 + 250 | 90 | 70 |
|  | 30 + 250 | 90 | 70 |
|  | 15 + 250 | 90 | 70 |
|  | 60 + 125 | 90 | 70 |

Table B-224:

|  | applic. rate (g ai./ha) | POLYGONUM CONVOLVULUS found | POLYGONUM CONVOLVULUS calc. |
|---|---|---|---|
| (I-2, Na salt) | 60 | 80 | |
| Glyphosate | 250 | 0 | |
| (I-2, Na salt) + Glyphosate | 60 + 250 | 95 | 80 |

Table B-225:

|  | applic. rate (g ai./ha) | SOLANUM NIGRUM found | SOLANUM NIGRUM calc. |
|---|---|---|---|
| (I-2, Na salt) | 60 | 98 | |
|  | 30 | 98 | |
|  | 15 | 98 | |
| Glyphosate | 250 | 0 | |
|  | 125 | 0 | |
| (I-2, Na salt) + Glyphosate | 60 + 250 | 100 | 98 |
|  | 30 + 250 | 100 | 98 |
|  | 30 + 125 | 100 | 98 |
|  | 15 + 125 | 100 | 98 |

Table B-226:

|  | applic. rate (g ai./ha) | STELLARIA MEDIA found | STELLARIA MEDIA calc. |
|---|---|---|---|
| (I-2, Na salt) | 60 | 98 |  |
|  | 30 | 50 |  |
|  | 15 | 50 |  |
| Glyphosate | 250 | 20 |  |
|  | 125 | 0 |  |
| (I-2, Na salt) + Glyphosate | 60 + 250 | 100 | 98.4 |
|  | 30 + 250 | 98 | 60 |
|  | 15 + 250 | 90 | 60 |
|  | 30 + 125 | 90 | 50 |
|  | 15 + 125 | 90 | 50 |

Table B-227:

|  | applic. rate (g ai./ha) | VIOLA ARVENSIS found | VIOLA ARVENSIS calc. |
|---|---|---|---|
| (I-2, Na salt) | 60 | 70 |  |
|  | 30 | 40 |  |
|  | 15 | 40 |  |
| Glyphosate | 250 | 0 |  |
|  | 125 | 0 |  |
| (I-2, Na salt) + Glyphosate | 60 + 250 | 98 | 70 |
|  | 30 + 250 | 98 | 40 |
|  | 15 + 250 | 90 | 40 |
|  | 60 + 125 | 95 | 70 |

Table B-228:

|  | applic. rate (g ai./ha) | LOLIUM PERENNE found | LOLIUM PERENNE calc. |
|---|---|---|---|
| (I-2, Na salt) | 15 | 60 |  |
| Sulfosulfuron | 8 | 0 |  |
| (I-2, Na salt) + Sulfosulfuron | 15 + 8 | 80 | 60 |

US 09/254,942     81     Le A 31 939-PUS

Table B-229:

|  | applic. rate (g ai./ha) | CHENOPODIUM ALBUM found | CHENOPODIUM ALBUM calc. |
|---|---|---|---|
| (I-2, Na salt) | 60 | 70 |  |
| Sulfosulfuron | 8 | 80 |  |
| (I-2, Na salt) + Sulfosulfuron | 60 + 8 | 100 | 94 |

Table B-230:

|  | applic. rate (g ai./ha) | VERONICA PERSICARIA found | VERONICA PERSICARIA calc. |
|---|---|---|---|
| (I-2, Na salt) | 30 | 20 |  |
|  | 15 | 0 |  |
| Sulfosulfuron | 8 | 0 |  |
|  | 4 | 0 |  |
| (I-2, Na salt) + Sulfosulfuron | 30 + 8 | 40 | 20 |
|  | 15 + 8 | 30 | 0 |
|  | 30 + 4 | 40 | 20 |

Table B-231:

|  | applic. rate (g ai./ha) | VIOLA ARVENSIS found | VIOLA ARVENSIS calc. |
|---|---|---|---|
| (I-2, Na salt) | 60 | 70 |  |
|  | 30 | 40 |  |
|  | 15 | 40 |  |
| Sulfosulfuron | 8 | 30 |  |
| (I-2, Na salt) + Sulfosulfuron | 60 + 8 | 95 | 79 |
|  | 30 + 8 | 90 | 58 |
|  | 15 + 8 | 90 | 58 |

Table B-232:

|  | applic. rate (g ai./ha) | XANTHIUM STRUMARIUM found | XANTHIUM STRUMARIUM calc. |
|---|---|---|---|
| (I-2, Na salt) | 60 | 90 |  |
|  | 30 | 70 |  |
| Sulfosulfuron | 8 | 60 |  |
|  | 4 | 60 |  |
| (I-2, Na salt) + Sulfosulfuron | 30 + 8 | 95 | 88 |
|  | 60 + 4 | 100 | 96 |

Table B-233:

|  | applic. rate (g ai./ha) | BROMUS SECALINUS found | BROMUS SECALINUS calc. |
|---|---|---|---|
| (I-2, Na salt) | 60 | 70 |  |
|  | 30 | 60 |  |
|  | 15 | 60 |  |
| Thifensulfuron-methyl | 8 | 0 |  |
|  | 4 | 0 |  |
| (I-2, Na salt) + Thifensulfuron-methyl | 60 + 8 | 90 | 70 |
|  | 30 + 8 | 80 | 60 |
|  | 30 + 4 | 80 | 60 |
|  | 15 + 4 | 80 | 60 |

Table B-234:

|  | applic. rate (g ai./ha) | ERIOCHLOA VILLOSA found | ERIOCHLOA VILLOSA calc. |
|---|---|---|---|
| (I-2, Na salt) | 60 | 90 |  |
|  | 30 | 90 |  |
|  | 15 | 90 |  |
| Thifensulfuron-methyl | 8 | 70 |  |
| (I-2, Na salt) + Thifensulfuron-methyl | 60 + 8 | 100 | 97 |
|  | 30 + 8 | 100 | 97 |
|  | 15 + 8 | 100 | 97 |

Table B-235:

|  | applic. rate (g ai./ha) | SETARIA VIRIDIS found | SETARIA VIRIDIS calc. |
|---|---|---|---|
| (I-2, Na salt) | 60 | 98 | |
|  | 30 | 90 | |
|  | 15 | 90 | |
| Thifensulfuron-methyl | 8 | 0 | |
|  | 4 | 0 | |
| (I-2, Na salt) + Thifensulfuron-methyl | 60 + 8 | 100 | 98 |
|  | 30 + 8 | 98 | 90 |
|  | 15 + 8 | 98 | 90 |
|  | 30 + 4 | 95 | 90 |
|  | 15 + 4 | 95 | 90 |

Table B-236:

|  | applic. rate (g ai./ha) | CHENOPODIUM ALBUM found | CHENOPODIUM ALBUM calc. |
|---|---|---|---|
| (I-2, Na salt) | 60 | 70 | |
| Thifensulfuron-methyl | 8 | 95 | |
| (I-2, Na salt) + Thifensulfuron-methyl | 60 + 8 | 100 | 98.5 |

Table B-237:

|  | applic. rate (g ai./ha) | IPOMOEA HEDERACEA found | IPOMOEA HEDERACEA calc. |
|---|---|---|---|
| (I-2, Na salt) | 60 | 70 | |
| Thifensulfuron-methyl | 4 | 70 | |
| (I-2, Na salt) + Thifensulfuron-methyl | 60 + 4 | 95 | 91 |

Table B-238:

|  | applic. rate (g ai./ha) | POLYGONUM CONVOLVULUS found | POLYGONUM CONVOLVULUS calc. |
|---|---|---|---|
| (I-2, Na salt) | 60 | 80 | |
|  | 30 | 80 | |
| Thifensulfuron-methyl | 8 | 95 | |
|  | 4 | 70 | |
| (I-2, Na salt) + Thifensulfuron-methyl | 60 + 8 | 100 | 99 |
|  | 30 + 8 | 100 | 99 |
|  | 60 + 4 | 98 | 94 |
|  | 30 + 4 | 98 | 94 |

Table B-239:

|  | applic. rate (g ai./ha) | SOLANUM NIGRUM found | SOLANUM NIGRUM calc. |
|---|---|---|---|
| (I-2, Na salt) | 60 | 98 | |
|  | 15 | 98 | |
| Thifensulfuron-methyl | 8 | 0 | |
|  | 4 | 0 | |
| (I-2, Na salt) + Thifensulfuron-methyl | 30 + 8 | 100 | 98 |
|  | 15 + 8 | 100 | 98 |
|  | 60 + 4 | 100 | 98 |

Table B-240:

|  | applic. rate (g ai./ha) | STELLARIA MEDIA found | STELLARIA MEDIA calc. |
|---|---|---|---|
| (I-2, Na salt) | 30 | 50 | |
|  | 15 | 50 | |
| Thifensulfuron-methyl | 4 | 80 | |
| (I-2, Na salt) + Thifensulfuron-methyl | 30 + 4 | 98 | 90 |
|  | 15 + 4 | 98 | 90 |

Table B-241:

|  | applic. rate (g ai./ha) | VERONICA PERSICARIA found | VERONICA PERSICARIA calc. |
|---|---|---|---|
| (I-2, Na salt) | 60 | 50 | |
| | 30 | 20 | |
| | 15 | 0 | |
| Thifensulfuron-methyl | 8 | 60 | |
| | 4 | 40 | |
| (I-2, Na salt) + Thifensulfuron-methyl | 60 + 8 | 100 | 80 |
| | 30 + 8 | 100 | 68 |
| | 60 + 4 | 100 | 70 |
| | 15 + 4 | 60 | 40 |

Table B-242:

|  | applic. rate (g ai./ha) | VIOLA ARVENSIS found | VIOLA ARVENSIS calc. |
|---|---|---|---|
| (I-2, Na salt) | 60 | 70 | |
| | 30 | 40 | |
| | 15 | 40 | |
| Thifensulfuron-methyl | 4 | 20 | |
| (I-2, Na salt) + Thifensulfuron-methyl | 60 + 4 | 100 | 76 |
| | 30 + 4 | 98 | 52 |
| | 15 + 4 | 98 | 52 |

Table B-243

|  | applic. rate (g ai./ha) | XANTHIUM STRUMARIUM found | XANTHIUM STRUMARIUM calc. |
|---|---|---|---|
| (I-2, Na salt) | 60 | 90 | |
| | 30 | 70 | |
| Thifensulfuron-methyl | 8 | 40 | |
| | 4 | 0 | |
| (I-2, Na salt) + Thifensulfuron-methyl | 60 + 8 | 100 | 94 |
| | 60 + 4 | 95 | 90 |
| | 30 + 4 | 95 | 70 |

Table B-244

|  | applic. rate (g ai./ha) | ALOPECURUS MYOSUROIDES found | ALOPECURUS MYOSUROIDES calc. |
|---|---|---|---|
| (I-1, Na salt) | 60 | 80 | |
| | 30 | 80 | |
| | 15 | 80 | |
| Carfentrazone-ethyl | 8 | 0 | |
| | 4 | 0 | |
| (I-1, Na salt) + Carfentrazone-ethyl | 60 + 8 | 98 | 80 |
| | 60 + 4 | 98 | 80 |
| | 30 + 8 | 98 | 80 |
| | 30 + 4 | 98 | 80 |
| | 15+8 | 98 | 80 |
| | 15+4 | 98 | 80 |

Table B-245

|  | applic. rate (g ai./ha) | BROMUS SECALINUS found | BROMUS SECALINUS calc. |
|---|---|---|---|
| (I-1, Na salt) | 15 | 90 | |
| Carfentrazone-ethyl | 15 | 30 | |
| | 8 | 30 | |
| | 4 | 20 | |
| (I-1, Na salt) + Carfentrazone-ethyl | 15 + 15 | 98 | 93 |
| | 15 + 8 | 98 | 93 |
| | 15 + 4 | 98 | 92 |

Table B-246

|  | applic. rate (g ai./ha) | CYPERUS ESCULENTUS found | CYPERUS ESCULENTUS calc. |
|---|---|---|---|
| (I-1, Na salt) | 60 | 70 | |
| | 30 | 70 | |
| | 15 | 70 | |
| Carfentrazone-ethyl | 8 | 30 | |
| (I-1, Na salt) + Carfentrazone-ethyl | 60 + 8 | 98 | 79 |
| | 30 + 8 | 98 | 79 |
| | 15 + 8 | 98 | 79 |

Table B-247

|  | applic. rate (g ai./ha) | DIGITARIA SANGUINALIS found | DIGITARIA SANGUINALIS calc. |
|---|---|---|---|
| (I-1, Na salt) | 60 | 50 |  |
| Carfentrazone-ethyl | 8 | 0 |  |
| (I-1, Na salt) + Carfentrazone-ethyl | 60 + 8 | 80 | 50 |

Table B-248

|  | applic. rate (g ai./ha) | ECHINOCHLOA CRUS-GALLI found | ECHINOCHLOA CRUS-GALLI calc. |
|---|---|---|---|
| (I-1, Na salt) | 60<br>30 | 90<br>90 |  |
| Carfentrazone-ethyl | 8 | 90 |  |
| (I-1, Na salt) + Carfentrazone-ethyl | 60 + 8<br>30 + 8 | 100<br>100 | 99<br>99 |

Table B-249

|  | applic. rate (g ai./ha) | ERIOCHLOA VILLOSA found | ERIOCHLOA VILLOSA calc. |
|---|---|---|---|
| (I-1, Na salt) | 60<br>30<br>15 | 20<br>20<br>0 |  |
| Carfentrazone-ethyl | 15<br>4 | 30<br>10 |  |
| (I-1, Na salt) + Carfentrazone-ethyl | 60 + 15<br>60 + 4<br>30 + 15<br>15 + 15 | 80<br>50<br>70<br>60 | 40<br>28<br>44<br>30 |

Table B-250

|  | applic. rate (g ai./ha) | LOLIUM PERENNE found | LOLIUM PERENNE calc. |
|---|---|---|---|
| (I-1, Na salt) | 60 | 70 | |
|  | 30 | 60 | |
|  | 15 | 30 | |
| Carfentrazone-ethyl | 15 | 30 | |
|  | 8 | 0 | |
|  | 4 | 0 | |
| (I-1, Na salt) + Carfentrazone-ethyl | 60 +15 | 98 | 79 |
|  | 60 + 8 | 98 | 70 |
|  | 60 + 4 | 98 | 70 |
|  | 30 + 15 | 98 | 72 |
|  | 30 + 8 | 98 | 60 |
|  | 15 + 15 | 90 | 51 |
|  | 15 +8 | 70 | 30 |
|  | 15 + 4 | 70 | 30 |

Table B-251

|  | applic. rate (g ai./ha) | SETARIA VIRIDIS found | SETARIA VIRIDIS calc. |
|---|---|---|---|
| (I-1, Na salt) | 60 | 70 | |
|  | 30 | 20 | |
|  | 15 | 20 | |
| Carfentrazone-ethyl | 15 | 30 | |
|  | 8 | 30 | |
|  | 4 | 20 | |
| (I-1, Na salt) + Carfentrazone-ethyl | 60 +15 | 95 | 79 |
|  | 30 + 15 | 90 | 44 |
|  | 30 + 8 | 80 | 44 |
|  | 30 + 4 | 70 | 36 |
|  | 15 + 15 | 70 | 44 |
|  | 15 +8 | 70 | 44 |
|  | 15 + 4 | 70 | 36 |

Table B-252

|  | applic. rate (g ai./ha) | CHENOPODIUM ALBUM found | CHENOPODIUM ALBUM calc. |
|---|---|---|---|
| (I-1, Na salt) | 30 | 60 |  |
| Carfentrazone-ethyl | 4 | 70 |  |
| (I-1, Na salt) + Carfentrazone-ethyl | 30 + 4 | 95 | 88 |

Table B-253

|  | applic. rate (g ai./ha) | GALIUM APARINE found | GALIUM APARINE calc. |
|---|---|---|---|
| (I-1, Na salt) | 60 | 70 |  |
|  | 30 | 50 |  |
|  | 15 | 30 |  |
| Carfentrazone-ethyl | 8 | 70 |  |
|  | 4 | 70 |  |
| (I-1, Na salt) + Carfentrazone-ethyl | 60 + 8 | 100 | 91 |
|  | 60 + 4 | 98 | 91 |
|  | 30 + 8 | 100 | 85 |
|  | 15 + 8 | 100 | 79 |

Table B-254

|  | applic. rate (g ai./ha) | POLYGONUM CONVOLVULUS found | POLYGONUM CONVOLVULUS calc. |
|---|---|---|---|
| (I-1, Na salt) | 60 | 70 |  |
|  | 30 | 50 |  |
|  | 15 | 0 |  |
| Carfentrazone-ethyl | 8 | 90 |  |
|  | 4 | 70 |  |
| (I-1, Na salt) + Carfentrazone-ethyl | 60 + 4 | 100 | 91 |
|  | 30 + 8 | 98 | 95 |
|  | 15 + 8 | 100 | 90 |

Table B-255

|  | applic. rate (g ai./ha) | STELLARIA MEDIA found | STELLARIA MEDIA calc. |
|---|---|---|---|
| (I-1, Na salt) | 60<br>30<br>15 | 80<br>50<br>0 |  |
| Carfentrazone-ethyl | 15 | 90 |  |
| (I-1, Na salt) +<br>Carfentrazone-ethyl | 60 + 15<br>30 + 15<br>15 + 15 | 100<br>100<br>100 | 98<br>95<br>90 |

Table B-256

|  | applic. rate (g ai./ha) | VERONICA PERSICARIA found | VERONICA PERSICARIA calc. |
|---|---|---|---|
| (I-1, Na salt) | 60<br>30<br>15 | 10<br>0<br>0 |  |
| Carfentrazone-ethyl | 4 | 98 |  |
| (I-1, Na salt) +<br>Carfentrazone-ethyl | 60 + 4<br>30 + 4<br>15 + 4 | 100<br>100<br>100 | 98.2<br>98<br>98 |

Table B-257

|  | applic. rate (g ai./ha) | VIOLA ARVENSIS found | VIOLA ARVENSIS calc. |
|---|---|---|---|
| (I-1, Na salt) | 60 | 98 |  |
| Carfentrazone-ethyl | 4 | 30 |  |
| (I-1, Na salt) +<br>Carfentrazone-ethyl | 60 + 4 | 100 | 98.6 |

US 09/254,942

Le A 31 939-PUS

Table B-258

|  | applic. rate (g ai./ha) | AVENA FATUA found | AVENA FATUA calc. |
|---|---|---|---|
| (I-1, Na salt) | 60 | 70 |  |
| Clodinafop-propargyl (80g/l) + Cloquintocet (20g/l) | 30 | 95 |  |
| (I-1, Na salt) + Clodinafop-propargyl (80g/l) + Cloquintocet (20g/l) | 60 + 30 | 100 | 98.5 |

Table B-259

|  | applic. rate (g ai./ha) | BROMUS SECALINUS found | BROMUS SECALINUS calc. |
|---|---|---|---|
| (I-1, Na salt) | 60<br>30<br>15 | 90<br>70<br>70 |  |
| Clodinafop-propargyl (80g/l) + Cloquintocet (20g/l) | 30 | 0 |  |
| (I-1, Na salt) + Clodinafop-propargyl (80g/l) + Cloquintocet (20g/l) | 60 + 30<br>30 + 30<br>15 + 30 | 98<br>98<br>98 | 90<br>70<br>70 |

Table B-260

|  | applic. rate (g ai./ha) | AMARANTHUS RETROFLEXUS found | AMARANTHUS RETROFLEXUS calc. |
|---|---|---|---|
| (I-1, Na salt) | 60 | 90 |  |
| Clodinafop-propargyl (80g/l) + Cloquintocet (20g/l) | 30<br>15 | 0<br>0 |  |
| (I-1, Na salt) + Clodinafop-propargyl (80g/l) + Cloquintocet (20g/l) | 60 + 30<br>60 + 15 | 100<br>95 | 90<br>90 |

Table B-261

|  | applic. rate (g ai./ha) | CHENOPODIUM ALBUM found | CHENOPODIUM ALBUM calc. |
|---|---|---|---|
| (I-1, Na salt) | 60 | 70 | |
| Clodinafop-propargyl (80g/l) + Cloquintocet (20g/l) | 30 | 0 | |
| (I-1, Na salt) + Clodinafop-propargyl (80g/l) + Cloquintocet (20g/l) | 60 + 30 | 90 | 70 |

Table B-262

|  | applic. rate (g ai./ha) | DATURA STRAMONIUM found | DATURA STRAMONIUM calc. |
|---|---|---|---|
| (I-1, Na salt) | 60<br>30<br>15 | 30<br>0<br>0 | |
| Clodinafop-propargyl (80g/l) + Cloquintocet (20g/l) | 30 | 0 | |
| (I-1, Na salt) + Clodinafop-propargyl (80g/l) + Cloquintocet (20g/l) | 60 + 30<br>30 + 30<br>15 + 30 | 70<br>60<br>40 | 30<br>0<br>0 |

Table B-263

|  | applic. rate (g ai./ha) | GALIUM APARINE found | GALIUM APARINE calc. |
|---|---|---|---|
| (I-1, Na salt) | 60<br>30 | 40<br>40 | |
| Clodinafop-propargyl (80g/l) + Cloquintocet (20g/l) | 30<br>15 | 0<br>0 | |
| (I-1, Na salt) + Clodinafop-propargyl (80g/l) + Cloquintocet (20g/l) | 60 + 30<br>30 + 30<br>60 + 15 | 60<br>50<br>50 | 40<br>40<br>40 |

Table B-264

|  | applic. rate (g ai./ha) | STELLARIA MEDIA found | STELLARIA MEDIA calc. |
|---|---|---|---|
| (I-1, Na salt) | 30 | 50 |  |
| Clodinafop-propargyl (80g/l) + Cloquintocet (20g/l) | 30 | 20 |  |
| (I-1, Na salt) + Clodinafop-propargyl (80g/l) + Cloquintocet (20g/l) | 30 + 30 | 80 | 60 |

Table B-265

|  | applic. rate (g ai./ha) | VIOLA ARVENSIS found | VIOLA ARVENSIS calc. |
|---|---|---|---|
| (I-1, Na salt) | 60 | 30 |  |
| Clodinafop-propargyl (80g/l) + Cloquintocet (20g/l) | 30 | 0 |  |
| (I-1, Na salt) + Clodinafop-propargyl (80g/l) + Cloquintocet (20g/l) | 60 + 30 | 70 | 30 |

US 09/254,942                               94                              Le A 31 939-PUS

The undersigned declarant hereby declares further that all statements made herein of his own knowledge are true and that all statements made on information and belief are believed to be true; and further that these statements were made with the knowledge that willful false statements and the like so made are punishable by fine or imprisonment, or both, under Section 1001 of Title 18 of the United States Code and that such willful false statements may jeopardize the validity of the application or any patent issued thereon.

2000-10-09
Date

Dr. Dieter Feucht

Appendix II

The Pesticide Manual, Eleventh Edition
Editor: C.D.S. Tomlin
The British Crop Protection Council
Cover page plus pages 323, 325, 597 and 598.
(5 pages)

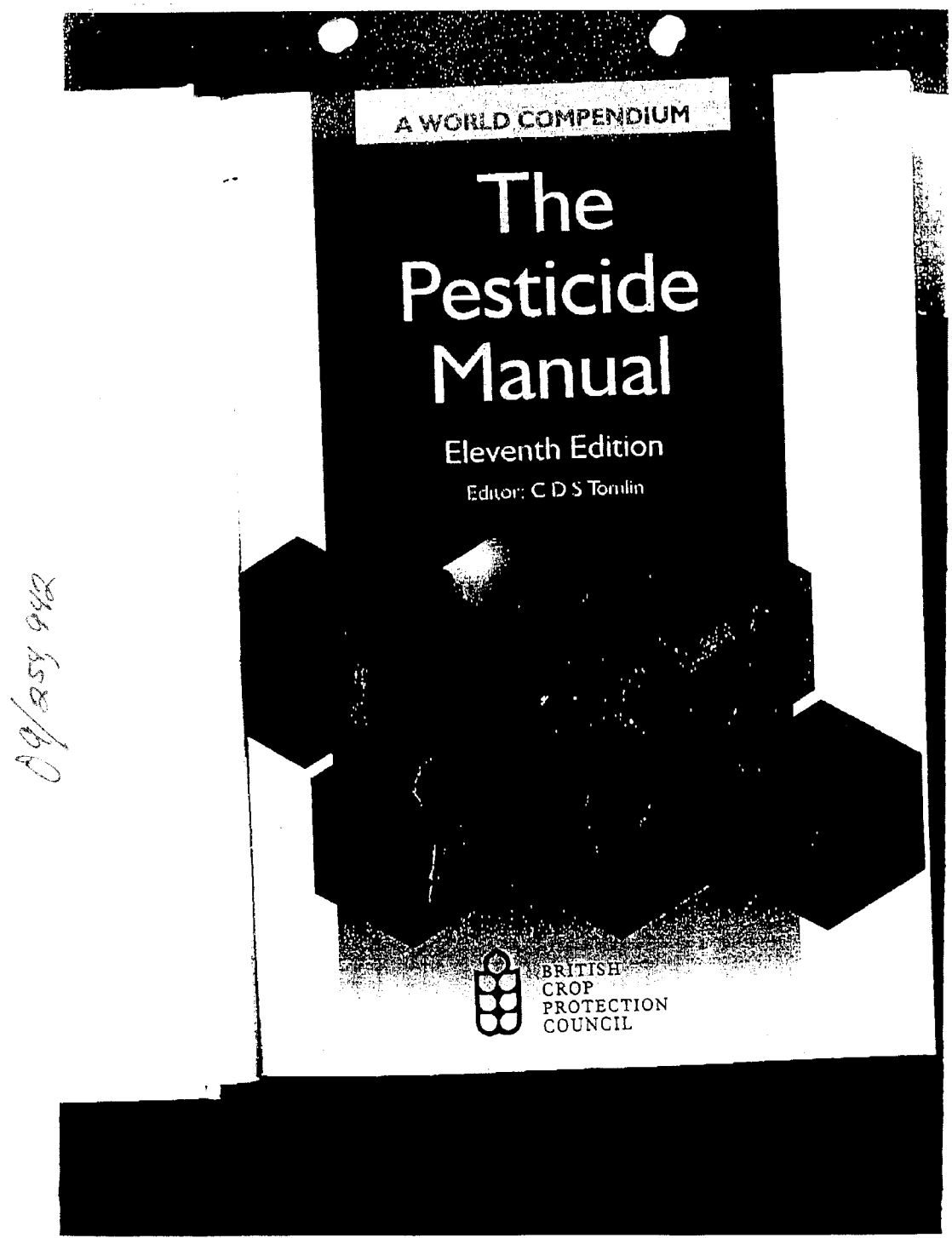

192 2,4-D — *Herbicide* aryloxyalkanoic acid

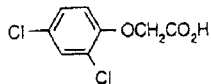

NOMENCLATURE
2,4-D
Common name 2,4-D (BSI, E-ISO, (m) F-ISO, WSSA); 2,4-PA (JMAF)
IUPAC name (2,4-dichlorophenoxy)acetic acid
Chemical Abstracts name (2,4-dichlorophenoxy)acetic acid
CAS RN [94-75-7]   EEC no. 202-361-1

*2,4-D-butotyl (2,4-D butoxyethyl ester)*
CAS RN [1929-73-3]

*2,4-D-butyl*
CAS RN [94-80-4]

*2,4-D-dimethylammonium*
CAS RN [2008-39-1]

*2,4-D-diolamine*
CAS RN [5742-19-8]

*2,4-D-2-ethylhexyl*
CAS RN [1928-43-4]

*2,4-D-isoctyl*
CAS RN [25168-26-7] (formerly [1320-20-2])

*2,4-D-isopropyl*
CAS RN [94-11-1]

*2,4-D-trolamine*
CAS RN [2569-01-9]

PHYSICAL CHEMISTRY
2,4-D
Composition Tech. is ≥96% pure.   Mol. wt. 221.0   M.f. $C_9H_6Cl_2O_3$
Form Colourless powder.   M.p. 140.5 °C   V.p. $1.1 \times 10^{-2}$ mPa (20 °C)
$K_{ow}$ logP = 2.58–2.83 (pH 1)   S.g./density 0.7–0.8   Solubility in water 311 mg/l 2,4-D   323 and its early history is covered in *The Hormone Weedkillers*, C. Kirby (1980).
Manufacturers Aimco; Amvac; Ancom; Atul; Crystal; Defensa; Krishi Rasayan; Marks; Nissan; Nitrokémia; Nufarm Ltd; Rhône-Poulenc; Sanachem; SDS Biotech; Shenzhen Jiangshan; Uniroyal; United Phosphorus Ltd APPLICATIONS
Mode of action Selective systemic herbicide. Salts are readily absorbed by the roots, whilst esters are readily absorbed by the foliage. Translocation occurs, with accumulation principally at the meristematic regions of shoots and roots. Acts as a growth inhibitor. Uses Post-emergence control of annual and perennial broad-leaved weeds in cereals, maize, sorghum, grassland, established turf, grass seed crops, orchards (pome fruit and stone fruit), cranberries, asparagus, sugar cane, rice, forestry, and on non-crop land (including areas adjacent to water) at 0.28–2.3 kg/ha. Control of broad-leaved aquatic weeds. The isopropyl ester can be also be used as a plant growth regulator to prevent premature fruit fall in citrus fruit. Phytotoxicity Phytotoxic to most broad-leaved crops, especially cotton, vines, tomatoes, ornamentals, fruit trees, oilseed rape and beet.

2,4-D
Formulation types EC; SL; SP; GR; SL. Mixtures (2,4-D +) amitrole; 2,4-DB; dichlorprop; MCPA; diuron; mecoprop; dalapon-sodium; simazine; ioxynil; bromoxynil; and many other herbicides. Compatibility Compatibility depends upon the particular formulation. Selected tradenames 'Agricorn D' (FCC); 'Capri' (Defensa); 'Dacamine' (ISK Biosciences); 'Damine' (Agriphar); 'Ded-Weed' (Uniroyal); 'Deferon' (Defensa); 'Desormone' (Rhône-Poulenc); 'Dikamin' (Nitrokémia); 'Dioweed' (United Phosphorus Ltd); 'Dymec' (PBI/Gordon); 'For-ester' (Vitax); 'Kay-D' (Krishi Rasayan); 'Novermone' (CFPI); 'Palormone' (Unicrop); 'Spritz-Hormin' (Nufarm B.V.); 'U 46 D' (BASF); 'Weedtox' (Aimco)

*2,4-D-butotyl (2,4-D butoxyethyl ester)*
Selected tradenames 'Erbitox LV-4' (Siapa)

*2,4-D-dimethylammonium*
Selected tradenames 'Erbitox Combi' (Siapa); 'Sanaphen D' (SL) (Sanachem); 'Staff' (Headland)

*2,4-D-isoctyl*
Formulation types EC. Selected tradenames 'Dicotox Extra' (Rhône-Poulenc); 'Supramone' (Rhône-Poulenc); 'Sanaphen D' (EC) (Sanachem)

ANALYSIS
Product analysis of 2,4-D, salts, esters and mixed combination products by acid-base titration, by glc (*CIPAC Handbook*, 1970, 1, 241; 1980, 1A, 1194; 1985, 1C, 2060; 1994, F, 292–319; *Herbicides 1977*, pp. 6–21) or by hplc (*AOAC Methods*, 2,4-D 325 formed which were readily degraded further. In aerobic sediment, flurochloridone degraded with $DT_{50}$ 3–18 d (2 soils). In the field, $DT_{50}$ 9–70 d. $K_{oc}$ 680–1300. $K_d$ 8–19, indicating low potential mobility on the McCall classification scale; flurochloridone does not leach because it is adsorbed and readily degraded in soil. For water, see Stability.

354 fluroxypyr — Herbicide aryloxyalkanoic acid

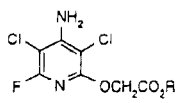

2-butoxy-1-methylethyl   $R = CH_3(CH_2)_3OCH_2CH(CH_3)$- meptyl (1-methylheptyl)   $R = CH_3(CH_2)_5CH(CH_3)$-

NOMENCLATURE
*fluroxypyr*
Common name fluroxypyr (BSI, draft E-ISO, (m) draft F-ISO)
IUPAC name 4-amino-3,5-dichloro-6-fluoro-2-pyridyloxyacetic acid
Chemical Abstracts name [(4-amino-3,5-dichloro-6-fluoro-2-pyridinyl)oxy]acetic acid
CAS RN [69377-81-7]   Development codes Dowco 433

*fluroxypyr-meptyl*
Other names fluroxypyr MHE   CAS RN [81406-37-3]   EEC no. 279-752-9
Development codes Dowco 433 MHE; XRD-433 1MHE; DOW-43300-H

*fluroxypyr-2-butoxy-1-methylethyl*
Other names fluroxypyr BPE   CAS RN [154486-27-8]
Development codes DOW-43304-H; DOE-81680-H

PHYSICAL CHEMISTRY
*fluroxypyr*
Mol. wt. 255.0  M.f. $C_7H_5Cl_2FN_2O_3$  Form White crystalline solid.
M.p. 232–233 °C  V.p. $3.784 \times 10^{-6}$ mPa (20 °C, Knudsen effusion)
$K_{ow}$ logP = –1.24 (unstated pH)  S.g./density 1.09 (24 °C)  Solubility In water 91 mg/l (20 °C). In acetone 51.0, methanol 34.6, ethyl acetate 10.6, isopropanol 9.2, dichloromethane 0.1, toluene 0.9, xylene 0.3 (all in g/l, 20 °C).
Stability Stable in acidic media. Fluroxypyr is acidic, and reacts with alkalis to form salts. $DT_{50}$ in water 185 d (pH 9, 20 °C). Stable at temperatures up to melting point. Stable in visible light.  pKa 2.94

*fluroxypyr 597*

*fluroxypyr-meptyl*
Mol. wt. 367.2   M.f. $C_{15}H_{21}Cl_2FN_2O_3$   Form Off-white solid.   M.p. 58.2–60 °C   V.p. $1.349 \times 10^{-3}$ mPa (20 °C, Knudsen effusion); $1 \times 10^{-2}$ mPa (20 °C, method unspecified)   $K_{ow}$ logP = 4.53   S.g./density 1.322   Solubility In water 0.09 mg/l. In acetone 867, methanol 469, ethyl acetate 792, dichloromethane 896, toluene 735, xylene 642, hexane 45 (all in g/l, 20 °C).   Stability Stable under normal storage conditions; decomposes above m.p. Stable in visible light. Hydrolytic $DT_{50}$ 454 d (pH 7), 3.2 d (pH 9); stable at pH 5. In natural waters, $DT_{50}$ 1–3 d.

*fluroxypyr-2-butoxy-1-methylethyl*
Mol. wt. 369.2   M.f. $C_{14}H_{19}Cl_2FN_2O_4$   Form Viscous dark brown liquid. B.p. decomp. 280 °C   V.p. $6 \times 10^{-3}$ mPa (20 °C)   $K_{ow}$ logP = 4.17   Henry (calc.) $1.8 \times 10^{-4}$ Pa m$^3$ mol$^{-1}$   S.g./density 1.294 (22 °C)   Solubility In water 12.6 (purified water), 10.8 (pH 5), 11.7 (pH 7), 11.5 (pH 9) mg/l (20 °C). In toluene, methanol, acetone, ethyl acetate >4000, hexane 68 g/l (20 °C).   F.p. 195.5 °C (Pensky Marten closed cup)

COMMERCIALISATION
History Herbicide reported by O. Visbecq *et al.* (COLUMA Conf., 1983, p. 257). Fluroxypyr-meptyl (the 1-methylheptyl ester) introduced in UK (1985) by Dow Chemical Co. (now DowElanco).   Manufacturers DowElanco

APPLICATIONS
Mode of action Fluroxypyr is applied as fluroxypyr-meptyl. After predominantly foliar uptake, the ester is hydrolysed to the parent acid, which is the herbicidally active form, and translocated rapidly to other parts of the plants. Acts by inducing characteristic auxin-type responses, e.g. leaf curling.   Uses Fluroxypyr is readily translocated, effective by post-emergence foliar application, controlling a range of economically important broad-leaved weeds (Including *Galium aparine*) in all small grain crops, and *Rumex* spp. and *Urtica dioica* in pastures. Directed applications are used against herbaceous and woody broad-leaved weeds in orchards (apple only) and plantation crops (rubber and oilpalm), and broad-leaved brush spp. in conifer forests. Post-emergence, broadcast applications of fluroxypyr in maize up to the 6-leaf stage of the crop are used for control of *Calystegia sepium*, *Convolvulus arvensis* and *Solanum nigrum*. The meptyl and 2-butoxy-1-methyl ethyl esters have similar activity, the advantage of the latter being the wider range of formulation options that are available.   Phytotoxicity Non-phytotoxic to the crops for which its use is recommended.

*fluroxypyr-meptyl*
Formulation types EC.   Mixtures *(fluroxypyr-meptyl +)* bromoxynil; isoproturon; bromoxynil + ioxynil; clopyralid + MCPA; dichlorprop + MCPA; clopyralid + ioxynil; glyphosate; bromoxynil + ioxynil + clopyralid; metosulam. Selected tradenames 'Starane' (DowElanco); 'Hurler' (Barclay)

and its early history is covered in The Hormone Weedkillers, C. Kirby (1980).
Manufacturers Aimco; Amvac; Ancom; Atul; Crystal; Defensa; Krishi Rasayan; Marks; Nissan; Nitrokémia; Nufarm Ltd; Rhône-Poulenc; Sanachem; SDS Biotech; Shenzhen Jiangshan; Uniroyal; United Phosphorus Ltd APPLICATIONS
Mode of action Selective systemic herbicide. Salts are readily absorbed by the roots, whilst esters are readily absorbed by the foliage. Translocation occurs, with accumulation principally at the meristematic regions of shoots and roots. Acts as a growth inhibitor. Uses Post-emergence control of annual and perennial broad-leaved weeds in cereals, maize, sorghum, grassland, established turf, grass seed crops, orchards (pome fruit and stone fruit), cranberries, asparagus, sugar cane, rice, forestry, and on non-crop land (including areas adjacent to water) at 0.28–2.3 kg/ha. Control of broad-leaved aquatic weeds. The isopropyl ester can be also be used as a plant growth regulator to prevent premature fruit fall in citrus fruit. Phytotoxicity Phytotoxic to most broad-leaved crops, especially cotton, vines, tomatoes, ornamentals, fruit trees, oilseed rape and beet.

2,4-D
Formulation types EC; SL; SP; GR; SL. Mixtures (2,4-D +) amitrole; 2,4-DB; dichlorprop; MCPA; diuron; mecoprop; dalapon-sodium; simazine; ioxynil; bromoxynil; and many other herbicides. Compatibility Compatibility depends upon the particular formulation. Selected tradenames 'Agricorn D' (FCC); 'Capri' (Defensa); 'Dacamine' (ISK Biosciences); 'Damine' (Agriphar); 'Ded-Weed' (Uniroyal); 'Deferon' (Defensa); 'Desormone' (Rhône-Poulenc); 'Dikamin' (Nitrokémia); 'Dioweed' (United Phosphorus Ltd); 'Dymec' (PBI/Gordon); 'For-ester' (Vitax); 'Kay-D' (Krishi Rasayan); 'Novermone' (CFPI); 'Palormone' (Unicrop); 'Spritz-Hormin' (Nufarm B.V.); 'U 46 D' (BASF); 'Weedtox' (Aimco)

*2,4-D-butotyl (2,4-D butoxyethyl ester)*
Selected tradenames 'Erbitox LV-4' (Siapa)

*2,4-D-dimethylammonium*
Selected tradenames 'Erbitox Combi' (Siapa); 'Sanaphen D' (SL) (Sanachem); 'Staff' (Headland)

*2,4-D-isoctyl*
Formulation types EC. Selected tradenames 'Dicotox Extra' (Rhône-Poulenc); 'Supramone' (Rhône-Poulenc); 'Sanaphen D' (EC) (Sanachem)

ANALYSIS
Product analysis of 2,4-D, salts, esters and mixed combination products by acid-base titration, by glc (*CIPAC Handbook*, 1970, 1, 241; 1980, 1A, 1194; 1985, 1C, 2060; 1994, F, 292–319; *Herbicides 1977*, pp. 6–21) or by hplc (*AOAC Methods*, 2,4-D 325 formed which were readily degraded further. In aerobic sediment, flurochloridone degraded with $DT_{50}$ 3–18 d (2 soils). In the field, $DT_{50}$ 9–70 d. $K_{oc}$ 680–1300. $K_d$ 8–19, indicating low potential mobility on the McCall classification scale; flurochloridone does not leach because it is adsorbed and readily degraded in soil. For water, see Stability.

354 fluroxypyr — Herbicide aryloxyalkanoic acid

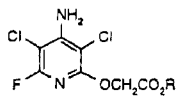

2-butoxy-1-methylethyl    $R = CH_3(CH_2)_3OCH_2CH(CH_3)$- meptyl (1-methylheptyl)    $R = CH_3(CH_2)_5CH(CH_3)$-

NOMENCLATURE
*fluroxypyr*
Common name fluroxypyr (BSI, draft E-ISO, (m) draft F-ISO)
IUPAC name 4-amino-3,5-dichloro-6-fluoro-2-pyridyloxyacetic acid
Chemical Abstracts name [(4-amino-3,5-dichloro-6-fluoro-2-pyridinyl)oxy]acetic acid
CAS RN [69377-81-7]    Development codes Dowco 433

*fluroxypyr-meptyl*
Other names fluroxypyr MHE    CAS RN [81406-37-3]    EEC no. 279-752-9
Development codes Dowco 433 MHE; XRD-433 1MHE; DOW-43300-H

*fluroxypyr-2-butoxy-1-methylethyl*
Other names fluroxypyr BPE    CAS RN [154486-27-8]
Development codes DOW-43304-H; DOE-81680-H

PHYSICAL CHEMISTRY
*fluroxypyr*
Mol. wt. 255.0    M.f. $C_7H_5Cl_2FN_2O_3$    Form White crystalline solid.
M.p. 232–233 °C    V.p. $3.784 \times 10^{-6}$ mPa (20 °C, Knudsen effusion)
$K_{ow}$ logP = –1.24 (unstated pH)    S.g./density 1.09 (24 °C)    Solubility In water 91 mg/l (20 °C). In acetone 51.0, methanol 34.6, ethyl acetate 10.6, isopropanol 9.2, dichloromethane 0.1, toluene 0.8, xylene 0.3 (all in g/l, 20 °C). Stability Stable in acidic media. Fluroxypyr is acidic, and reacts with alkalis to form salts. $DT_{50}$ in water 185 d (pH 9, 20 °C). Stable at temperatures up to melting point. Stable in visible light.    pKa 2.94

*fluroxypyr-meptyl*
Mol. wt. 367.2  M.f. $C_{15}H_{21}Cl_2FN_2O_3$  Form Off-white solid.  M.p. 58.2–60 °C
V.p. $1.349 \times 10^{-3}$ mPa (20 °C, Knudsen effusion); $1 \times 10^{-2}$ mPa (20 °C, method unspecified)  $K_{ow}$ logP = 4.53  S.g./density 1.322  Solubility In water 0.09 mg/l. In acetone 867, methanol 469, ethyl acetate 792, dichloromethane 896, toluene 735, xylene 642, hexane 45 (all in g/l, 20 °C).  Stability Stable under normal storage conditions; decomposes above m.p. Stable in visible light. Hydrolytic $DT_{50}$ 454 d (pH 7), 3.2 d (pH 9); stable at pH 5. In natural waters, $DT_{50}$ 1–3 d.

*fluroxypyr-2-butoxy-1-methylethyl*
Mol. wt. 369.2  M.f. $C_{14}H_{19}Cl_2FN_2O_4$  Form Viscous dark brown liquid.
B.p. decomp. 280 °C  V.p. $6 \times 10^{-3}$ mPa (20 °C)  $K_{ow}$ logP = 4.17  Henry (calc.) $1.8 \times 10^{-4}$ Pa m$^3$ mol$^{-1}$  S.g./density 1.294 (22 °C)  Solubility In water 12.6 (purified water), 10.8 (pH 5), 11.7 (pH 7), 11.5 (pH 9) mg/l (20 °C). In toluene, methanol, acetone, ethyl acetate >4000, hexane 68 g/l (20 °C).  F.p. 195.5 °C (Pensky Marten closed cup)

COMMERCIALISATION
History Herbicide reported by O. Visbecq et al. (COLUMA Conf., 1983, p. 257). Fluroxypyr-meptyl (the 1-methylheptyl ester) introduced In UK (1985) by Dow Chemical Co. (now DowElanco).  Manufacturers DowElanco APPLICATIONS
Mode of action Fluroxypyr is applied as fluroxypyr-meptyl. After predominantly foliar uptake, the ester is hydrolysed to the parent acid, which is the herbicidally active form, and translocated rapidly to other parts of the plants. Acts by inducing characteristic auxin-type responses, e.g. leaf curling.  Uses Fluroxypyr is readily translocated, effective by post-emergence foliar application, controlling a range of economically important broad-leaved weeds (Including *Galium aparine*) in all small grain crops, and *Rumex* spp. and *Urtica dioica* in pastures. Directed applications are used against herbaceous and woody broad-leaved weeds in orchards (apple only) and plantation crops (rubber and oilpalm), and broad-leaved brush spp. in conifer forests. Post-emergence, broadcast applications of fluroxypyr in maize up to the 6-leaf stage of the crop are used for control of *Calystegia sepium*, *Convolvulus arvensis* and *Solanum nigrum*. The meptyl and 2-butoxy-1-methyl ethyl esters have similar activity, the advantage of the latter being the wider range of formulation options that are available.  Phytotoxicity Non-phytotoxic to the crops for which its use is recommended.

*fluroxypyr-meptyl*
Formulation types EC.  Mixtures *(fluroxypyr-meptyl +)* bromoxynil; isoproturon; bromoxynil + ioxynil; clopyralid + MCPA; dichlorprop + MCPA; clopyralid + ioxynil; glyphosate; bromoxynil + ioxynil + clopyralid; metosulam.
Selected tradenames 'Starane' (DowElanco); 'Hurler' (Barclay)

What is claimed is:

1. A herbicidal composition comprising an effective content of a combination of:
   (a) an arylsulphonylaminocarbonyltriazolinone selected from the group consisting of 2-(2-methoxycarbonylphenylsulphonylaminocarbonyl)-4-methyl-5-n-propoxy-2,4-dihydro-3H-1,2,4-trizol-3-one (I-1), 2-(2-trifluoromethoxy-phenylsulphonylaminocarbonyl)-4-methyl-5-methoxy-2,4-dihydro-3H-1,2,4-triazol-3-one (I-2), a sodium salt of 2-(2-methoxycarbonylphenylsulphonylaminocarbonyl)-4-methyl-5-n-propoxy-2,4-dihydro-3H-1,2,4-trizol-3-one (I-1), a sodium salt of 2-(2-trifluoromethoxy-phenyl-sulphonylaminocarbonyl)-4-methyl-5-methoxy-2,4-dihydro-3H-1,2,4-triazol-3-one (I-2) and mixtures thereof; and
   (b) a herbicide selected from the group consisting of imazamethabenz-methyl, sulfosulfuron, tribenuron-methyl, amidosulfuron, metosulam, flurtamone, 2,4-D, bromoxynil, dichlorprop-P, tribenuron(-methyl), diflufenican, glyphosate(-isopropyl-ammonium), metsulfuron-methyl, fluroxypyr, isoproturon, imazamox, diclofop-methyl, carfentrazone-ethyl, clodinafop-propargyl, thifensulfuron-methyl and mixtures thereof.

2. The herbicidal composition of claim 1 wherein,
   (a) said arylsulphonylaminocarbonyltriazolinone is selected from the group consisting of 2-(2-methoxycarbonylphenylsulphonylaminocarbonyl)-4-methyl-5-n-propoxy-2,4-dihydro-3H-1,2,4-trizol-3-one (I-1), a sodium salt of 2-(2-methoxycarbonylphenylsulphonylaminocarbonyl)-4-methyl-5-n-propoxy-2,4-dihydro-3H-1,2,4-trizol-3-one (I-1) and mixtures thereof; and
   (b) said herbicide is selected from the group consisting of imazamethabenz-methyl, sulfosulfuron, tribenuron-methyl, amidosulfuron, metosulam, flurtamone, 2,4-D, diflufenican, glyphosate(-isopropylammonium), metsulfuron-methyl, fluroxypyr, isoproturon, imazamox, carfentrazone-ethyl, clodinafop-propargyl and mixtures thereof.

3. The herbicidal composition of claim 1 wherein,
   (a) said arylsulphonylaminocarbonyltriazolinone is selected from the group consisting of 2-(2-trifluoromethoxy-phenylsulphonylaminocarbonyl)-4-methyl-5-methoxy-2,4-dihydro-3H-1,2,4-triazol-3-one (I-2), a sodium salt of 2-(2-trifluoromethoxy-phenylsulphonylaminocarbonyl)-4-methyl-5-methoxy-2,4-dihydro-3H-1,2,4-triazol-3-one (I-2) and mixtures thereof; and
   (b) said herbicide is selected from the group consisting of imazamethabenz-methyl, sulfosulfuron, 2,4-D, bromoxynil, dichlorprop-P, tribenuron(-methyl), glyphosate(-isopropylammonium), fluroxypyr, imazamox, diclofop-methyl, carfentrazone-ethyl, clodinafop-propargyl, thifensulfuron-methyl and mixtures thereof.

4. A herbicidal composition comprising an effective content of a combination of:
   (a) an arylsulphonylaminocarbonyltriaxolinone selected from the group consisting of 2-(2-methoxycarbonyl-phenylsulphonylaminocarbonyl)-4-methyl-5-n-propoxy-2,4-dihydro-3H-1,2,4-triazol-3-one (I-1), 2-(2-trifluoromethoxy-phenylsulphonylaminocarbonyl)-4-methyl-5-methoxy-2,4-dihydro-3H-1,2,4-triazol-3-one (I-2), a sodium salt of 2-(2-methoxycarbonyl-phenylsulphonylaminocarbonyl)- 4-methyl-5-n-propoxy-2,4-dihydro-3H-1,2,4-triazol-3-one (I-1), and a sodium salt of 2-(2-trifluoromethoxy-phenylsulphonylaminocarbonyl)-4-methyl-5-methoxy-2,4-dihydro-3H-1,2,4-triazol-3-one (I-2); and
   (b) 4-amino-6-tert-butyl-3-methylthio-1,2,4-triazine-5 (4H)-one (metribuzin).

5. The herbicidal composition according to any one of claims 1 to 4, comprising from 0.05 to 500 parts by weight, of said herbicide (b) per part by weight of said arylsulphonylaminocarbonyltriazolinone (a).

6. A method for controlling weeds, comprising the step of applying the herbicidal composition according to any one of claims 1 to 4 on weeds or their habitat.

7. A process for preparing herbicidal compositions, comprising the step of mixing the herbicidal composition according to any one of claims 1 to 4 with extenders and/or surfactants.

* * * * *

UNITED STATES PATENT AND TRADEMARK OFFICE
CERTIFICATE OF CORRECTION

PATENT NO.    : 6,316,386 B1
DATED         : November 13, 2001
INVENTOR(S)   : Dahmen et al.

It is certified that error appears in the above-identified patent and that said Letters Patent is hereby corrected as shown below:

Delete columns 19-222.

Signed and Sealed this

Ninth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,316,386 B1
DATED          : January 20, 2004
INVENTOR(S)    : Dahmen et al.

It is certified that error appears in the above-identified patent and that said Letters Patent is hereby corrected as shown below:

<u>Title page,</u>
Item [75], delete "Leverkusen" and substitute -- Neuss --

Signed and Sealed this

Thirteenth Day of April, 2004

JON W. DUDAS
*Acting Director of the United States Patent and Trademark Office*